United States Patent
Park et al.

(10) Patent No.: US 9,331,286 B2
(45) Date of Patent: May 3, 2016

(54) ORGANIC ELECTROLUMINESCENT COMPOUNDS AND ORGANIC ELECTROLUMINESCENT DEVICE USING THE SAME

(71) Applicant: SFC Co., Ltd., Chungcheongbuk-do (KR)

(72) Inventors: Sang-woo Park, Seoul (KR); Byung-sun Yang, Jeollabuk-do (KR); Se-Jin Lee, Daejeon (KR)

(73) Assignee: SFC CO. LTD., Chungcheongbuk-do (KR)

( * ) Notice: Subject to any disclaimer, the term of this patent is extended or adjusted under 35 U.S.C. 154(b) by 143 days.

(21) Appl. No.: 14/193,564

(22) Filed: Feb. 28, 2014

(65) Prior Publication Data
US 2014/0239279 A1  Aug. 28, 2014

(30) Foreign Application Priority Data
Feb. 28, 2013 (KR) .......... 10-2013-0021790

(51) Int. Cl.
*H01L 51/00* (2006.01)
*C07D 311/82* (2006.01)

(52) U.S. Cl.
CPC ........... *H01L 51/006* (2013.01); *C07D 311/82* (2013.01); *H01L 51/0061* (2013.01); *H01L 51/0058* (2013.01); *H01L 51/0073* (2013.01)

(58) Field of Classification Search
None
See application file for complete search history.

(56) References Cited

U.S. PATENT DOCUMENTS

| 2004/0028944 A1* | 2/2004 | Mori ................. C07C 211/61 428/691 |
| 2005/0264174 A1* | 12/2005 | Liao ................. H01L 1/5278 313/500 |
| 2015/0162542 A1* | 6/2015 | Ryu ................. H01L 51/0059 257/40 |

FOREIGN PATENT DOCUMENTS

WO   WO 2014/030822 A1 * 2/2014 ............ H01L 51/006

* cited by examiner

*Primary Examiner* — J. L. Yang
(74) *Attorney, Agent, or Firm* — Duane Morris LLP; J. Rodman Steele, Jr.; Gregory M. Lefkowitz

(57) ABSTRACT

The present disclosure relates to an organic electroluminescent compound employed as a hole transport material or a hole injection material and an organic electroluminescent device including the same. The organic electroluminescent compound is represented by [Chemical Formula 1] and an organic electroluminescent device employing the organic electroluminescent compound as a hole transport material exhibits very superior luminous efficiency and lifetime characteristics.

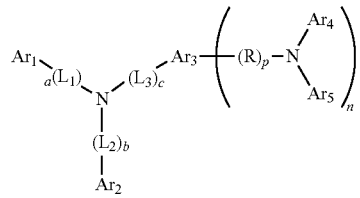

[Chemical Formula 1]

9 Claims, 1 Drawing Sheet

| 80 |
|---|
| 70 |
| 60 |
| 50 |
| 40 |
| 30 |
| 20 |
| 10 |

| 80 |
|---|
| 70 |
| 60 |
| 50 |
| 40 |
| 30 |
| 20 |
| 10 |

ORGANIC ELECTROLUMINESCENT COMPOUNDS AND ORGANIC ELECTROLUMINESCENT DEVICE USING THE SAME

CROSS-REFERENCE TO RELATED APPLICATIONS

This application claims priority under 35 U.S.C. §119 to Korean Patent Application No. 10-2013-0021790 filed on Feb. 28, 2013 in the Korean Intellectual Property Office, the disclosure of which is incorporated herein by reference in its entirety.

TECHNICAL FIELD

The present disclosure relates to an organic electroluminescent compound, more particularly an organic electroluminescent compound employed as a hole transport material, and an organic electroluminescent device having long lifetime and remarkably improved luminous efficiency by employing same.

BACKGROUND

An organic electroluminescent device is advantageous in that the device can be built on a transparent substrate, can operate at low voltages of 10 V or below as compared to a plasma display panel or an inorganic electroluminescent (EL) display, consumes relatively less power, provides excellent color quality and can display green, blue and red colors. Accordingly, it attracts a great deal of interests as a next-generation display device.

For the organic electroluminescent device to fully exert the above-mentioned characteristics, a hole injection material, a hole transport material, an electroluminescent material, an electron transport material, an electron injection material, etc. included in an organic layer of the device should be stable and effective. However, development of such stable and effective materials for the organic layer of the organic electroluminescent device is not satisfactory as yet. Accordingly, development of new materials exhibiting operability at low voltage, high efficiency and long lifetime is consistently needed.

As hole transport materials, copper phthalocyanine (CuPc), MTDATA, 4,4'-bis[N-(1-naphthyl)-N-phenylamino] biphenyl (NPB), N,N'-diphenyl-N,N'-bis(3-methylphenyl)-(1,1'-biphenyl)-4,4'-diamine (TPD), etc. are known. However, since these materials are problematic in efficiency and lifetime when they are employed in devices, many arylamine-based compounds having various substituents are being developed. But, they are also insufficient to satisfy both the efficiency and long lifetime.

SUMMARY

The present disclosure is directed to providing an organic electroluminescent compound having improved efficiency and lifetime characteristics over the existing hole transport materials.

The present disclosure is also directed to providing an organic electroluminescent device exhibiting very superior luminous efficiency and lifetime characteristics by employing the organic electroluminescent compound in a hole transport layer.

In one general aspect, the present disclosure provides an organic electroluminescent compound represented by [Chemical Formula 1]:

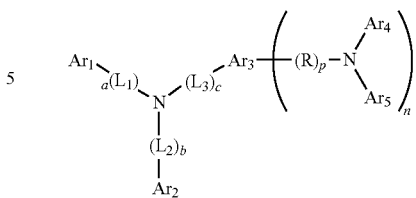

[Chemical Formula 1]

The specific substituents in [Chemical Formula 1] will be described later.

In another general aspect, the present disclosure provides an organic electroluminescent device including: a first electrode; a second electrode; and an organic layer disposed between the first electrode and the second electrode, wherein the organic layer includes at least one organic electroluminescent compound(s) represented by [Chemical Formula 1].

An organic electroluminescent device employing the organic electroluminescent compound according to the present disclosure as a hole transport material exhibits very superior luminous efficiency and lifetime characteristics.

BRIEF DESCRIPTION OF DRAWING

The above and other objects, features and advantages of the present disclosure will become apparent from the following description of certain exemplary embodiments given in conjunction with the accompanying drawing, in which:

FIG. 1 schematically shows an organic electroluminescent device according to an exemplary embodiment of the present disclosure.

DETAILED DESCRIPTION OF EMBODIMENTS

Hereinafter, the present disclosure is described in further detail.

In an aspect, the present disclosure provides an organic electroluminescent compound represented by [Chemical Formula 1]:

[Chemical Formula 1]

wherein
each of $L_1$ through $L_3$, which are identical or different, is independently selected from a substituted or unsubstituted $C_{6-30}$ aryl group and a substituted or unsubstituted $C_{5-30}$ heteroaryl group,
each of a, b and c is independently an integer from 0 to 3, wherein if a, b and c are 2 or greater, the plurality of $L_1$'s through $L_3$'s are identical or different,
each of $Ar_1$ through $Ar_5$, which are identical or different, is independently selected from a group represented by [Chemical Formula L], a substituted or unsubstituted $C_{1-30}$ alkyl group, a substituted or unsubstituted $C_{6-60}$ aryl group and a substituted or unsubstituted $C_{5-60}$ heteroaryl group, wherein at least one of $Ar_1$ through $Ar_3$ is a group represented by [Chemical Formula L], R is selected from a substituted or unsubstituted $C_{6-60}$ aryl group and a substituted or unsubstituted $C_{5-60}$ heteroaryl group, p is an integer from 0 to 3, wherein if p is 2 or greater, the plurality of R's are identical or different,

[Chemical Formula L]

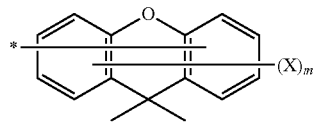

wherein

X is selected from hydrogen, deuterium, a halogen atom, a cyano group, a nitro group, a substituted or unsubstituted $C_{1-30}$ alkyl group, a substituted or unsubstituted $C_{5-60}$ heteroaryl group, a substituted or unsubstituted $C_{3-30}$ cycloalkyl group, a substituted or unsubstituted $C_{6-60}$ aryl group, a substituted or unsubstituted $C_{1-30}$ alkoxy group, a substituted or unsubstituted $C_{6-60}$ aryloxy group, a substituted or unsubstituted $C_{1-30}$ alkylamino group, a substituted or unsubstituted $C_{6-60}$ arylamino group, a substituted or unsubstituted $C_{1-30}$ alkylsilyl group, a substituted or unsubstituted $C_{6-60}$ arylsilyl group and a substituted or unsubstituted $C_{2-30}$ alkenyl group, m is an integer from 0 to 7, wherein if m is 2 or greater, the plurality of X's are identical or different, and n is an integer from 0 to 3, wherein if n is 2 or greater, the plurality of

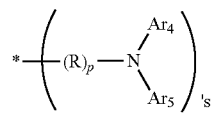

are identical or different.

If $L_1$ through $L_3$, $Ar_1$ through $Ar_5$, R and X are further substituted with substituents, the substituent may be one or more selected from deuterium, a cyano group, a halogen group, a nitro group, a $C_{1-20}$ alkyl group, a $C_{6-30}$ aryl group, a $C_{5-30}$ heteroaryl group, a $C_{1-20}$ alkylamino group, a $C_{6-30}$ arylamino group, a $C_{1-20}$ alkoxy group, a $C_{6-30}$ aryloxy group, a $C_{3-20}$ cycloalkyl group, a $C_{6-30}$ arylthio group, a $C_{1-20}$ alkenyl group, a $C_{1-20}$ alkylsilyl group and a $C_{6-30}$ arylsilyl group, and the substituent may be connected with an adjacent substituent to form a saturated or unsaturated ring.

In the "substituted or unsubstituted $C_{1-30}$ alkyl group", the "substituted or unsubstituted $C_{6-60}$ aryl group", etc., the number of carbon atoms of the $C_{1-30}$ alkyl group, the $C_{6-60}$ aryl group, etc. means the number of carbon atoms of the alkyl or aryl moiety without considering the substituent. For example, a phenyl group having a butyl group substituted at the para-position is a $C_6$ aryl group substituted with a $C_4$ butyl group.

In an exemplary embodiment of the present disclosure, n in [Chemical Formula 1] may be 0 or 1 and, if n in [Chemical Formula 1] is 0, the compound represented by [Chemical Formula 1] may be a compound selected from compounds represented by [Chemical Formula 1-1] through [Chemical Formula 1-3]:

[Chemical Formula 1-1]

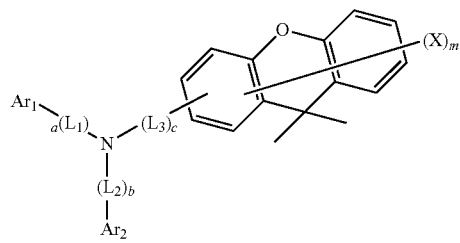

[Chemical Formula 1-2]

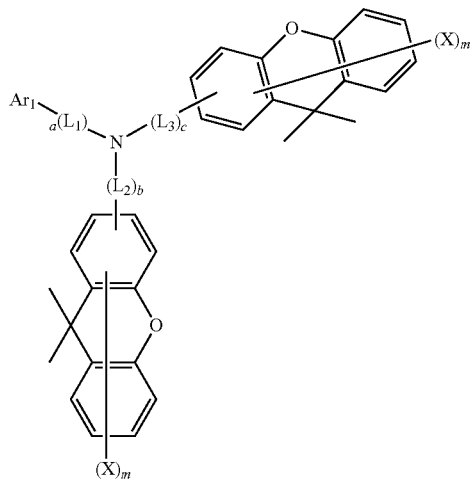

[Chemical Formula 1-3]

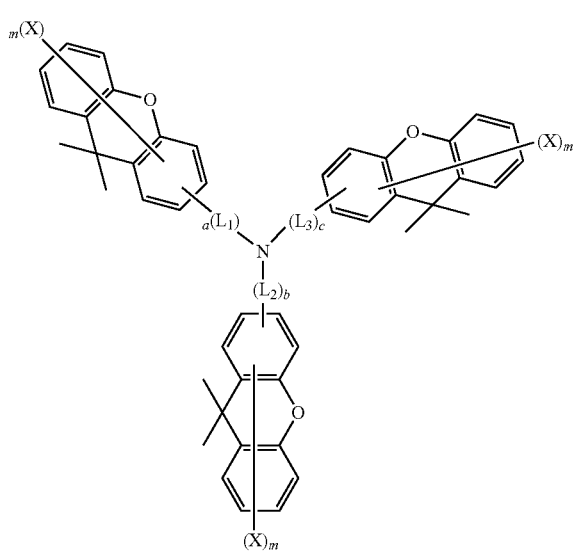

wherein each of $Ar_1$, $Ar_2$, $L_1$ through $L_3$, X, a through c and m is the same as defined in [Chemical Formula 1].

The aryl group in the compound of the present disclosure is an organic radical derived from an aromatic hydrocarbon by the removal of one hydrogen atom and includes a 5- to 7-membered, specifically 5- or 6-membered, single or fused ring. If the aryl group has a substituent, it may be fused with a neighboring substituent to further form a ring.

Specific examples of the aryl group include phenyl, naphthyl, biphenyl, terphenyl, anthryl, indenyl, fluorenyl, phenanthryl, triphenylenyl, pyrenyl, perylenyl, chrysenyl, naphthacenyl, fluoranthenyl, etc., but are not limited thereto.

One or more hydrogen atom(s) of the aryl group may be substituted with a deuterium atom, a halogen atom, a hydroxy group, a nitro group, a cyano group, a silyl group, an amino group (—$NH_2$, —NH(R), —N(R')(R''), R' and R'' are independently $C_{1-10}$ alkyl groups, in this case the amino group is called an "alkylamino group"), an amidino group, a hydrazine group, a hydrazone group, a carboxyl group, a sulfonate group, a phosphate group, a $C_{1-24}$ alkyl group, a halogenated $C_{1-24}$ alkyl group, a $C_{1-24}$ alkenyl group, a $C_{1-24}$ alkynyl group, a $C_{1-24}$ heteroalkyl group, a $C_{6-24}$ aryl group, a $C_{6-24}$ arylalkyl group, a $C_{2-24}$ heteroaryl group or a $C_{2-24}$ heteroarylalkyl group.

The heteroaryl group as a substituent in the compound of the present disclosure refers to a $C_{2-24}$ heteroaromatic organic radical which may contain 1-4 heteroatom(s) selected from N, O, P or S in each ring of the aryl group described above. The rings may be fused to form a ring. Also, one or more hydrogen atom(s) of the heteroaryl group may be substituted with a substituent as described with regard to the aryl group.

Specific examples of the heteroaryl group include pyridinyl, pyrimidinyl, triazinyl, indolinyl, quinolinyl, quinazolinyl, pyrrolidinyl, thiophenyl, furanyl, piperidinyl, morpholinyl, piperazinyl, carbazolyl, azacarbazolyl, oxazolyl, oxadiazolyl, benzoxazolyl, thiazolyl, thiadiazolyl, benzothiazolyl, triazolyl, imidazolyl, benzimidazolyl, etc., but are not limited thereto.

Specific examples of the alkyl group used as a substituent in the present disclosure include methyl, ethyl, propyl, isobutyl, sec-butyl, tert-butyl, pentyl, isoamyl, hexyl, heptyl, octyl, stearyl, trichloromethyl, trifluoromethyl, etc. One or more hydrogen atom(s) of the alkyl group may be substituted with a substituent as described with regard to the aryl group.

Specific examples of the cycloalkyl group as a substituent in the compound of the present disclosure include cyclopropyl, cyclobutyl, cyclopentyl, cyclohexyl, cycloheptyl, cyclooctyl, adamantyl, etc. One or more hydrogen atom(s) of the cycloalkyl group may be substituted with a substituent as described with regard to the aryl group.

Specific examples of the alkoxy group as a substituent in the compound of the present disclosure include methoxy, ethoxy, propoxy, isobutyloxy, sec-butyloxy, pentyloxy, isoamyloxy, hexyloxy, etc. One or more hydrogen atom(s) of the alkoxy group may be substituted with a substituent as described with regard to the aryl group.

Specific examples of the halogen group as a substituent in the compound of the present disclosure include fluorine (F), chlorine (Cl), bromine (Br), iodine (I), etc.

Specific examples of the silyl group as a substituent in the compound of the present disclosure include trimethylsilyl, triethylsilyl, triphenylsilyl, trimethoxysilyl, dimethoxyphenylsilyl, diphenylmethylsilyl, diphenylvinylsilyl, methylcyclobutylsilyl, dimethylfurylsilyl, etc. One or more hydrogen atom(s) of the silyl group may be substituted with a substituent as described with regard to the aryl group.

In an exemplary embodiment of the present disclosure, the compound represented by [Chemical Formula 1] may be selected from a group consisting of compounds represented by [Chemical Formula 2] through [Chemical Formula 120]:

[Chemical Formula 2]

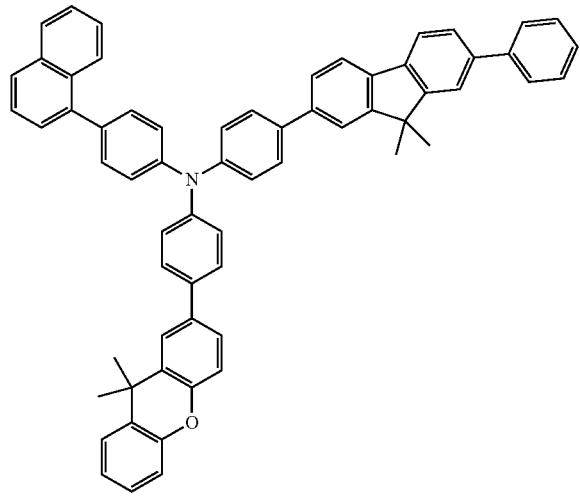

[Chemcial Formula 3]

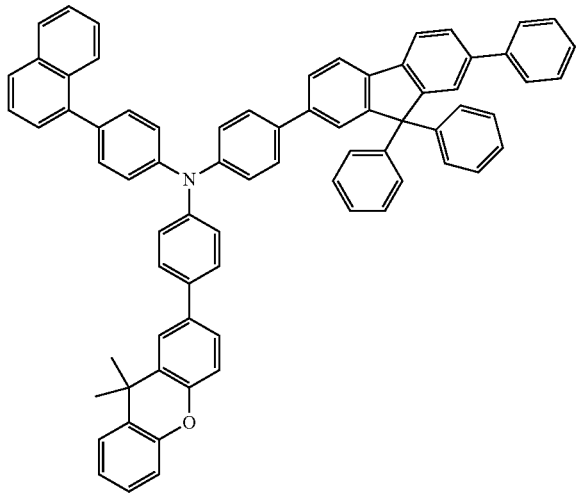

-continued
[Chemical Formula 4]
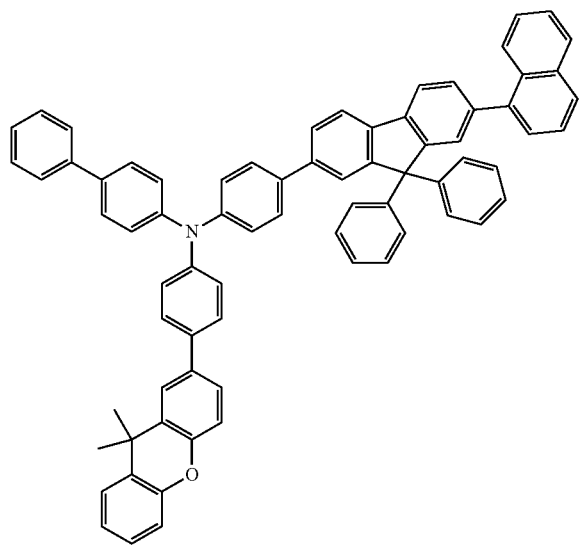
[Chemical Formula 5]
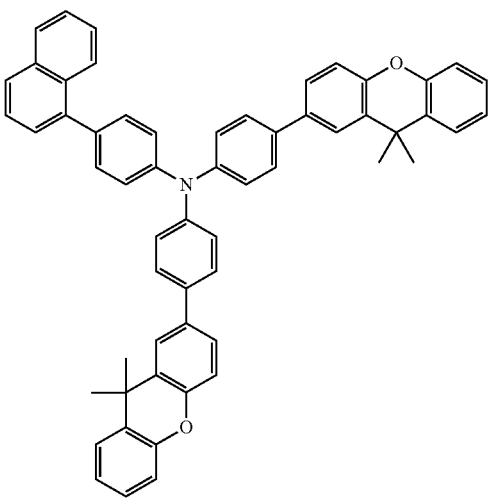
[Chemical Formula 6]
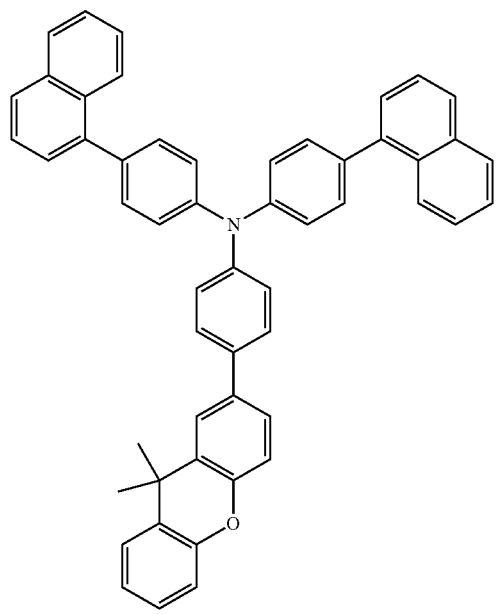
[Chemical Formula 7]
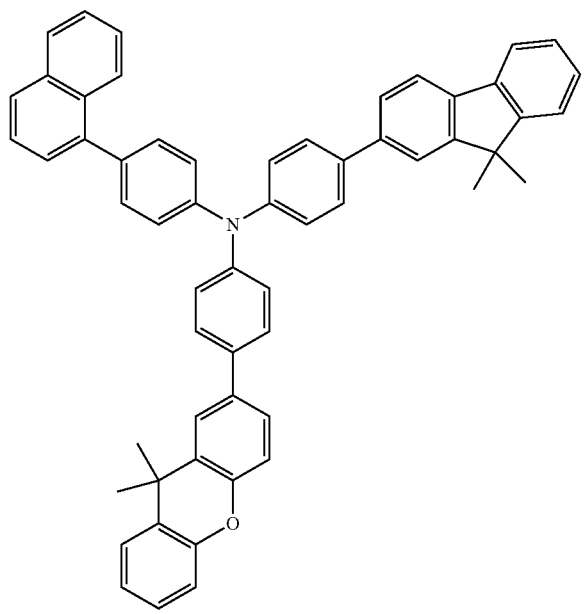

-continued
[Chemical Formula 8]
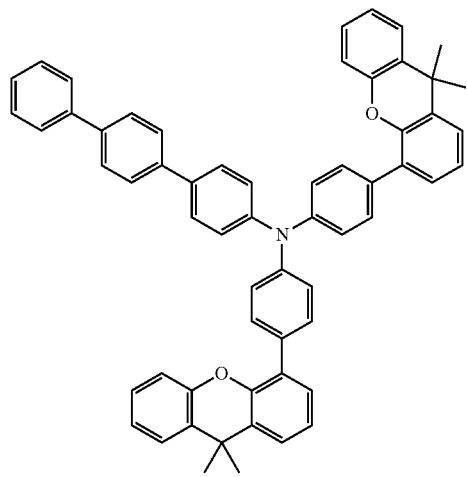
[Chemical Formula 9]
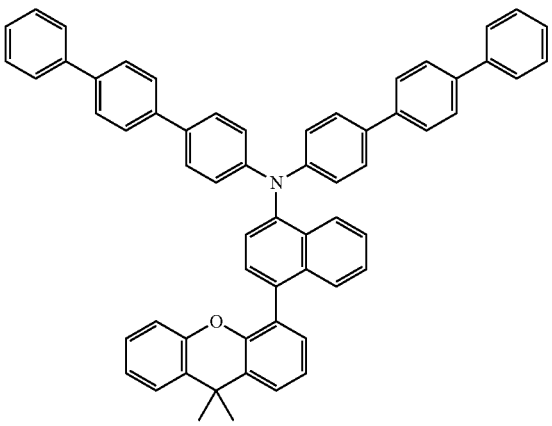
[Chemical Formula 10]
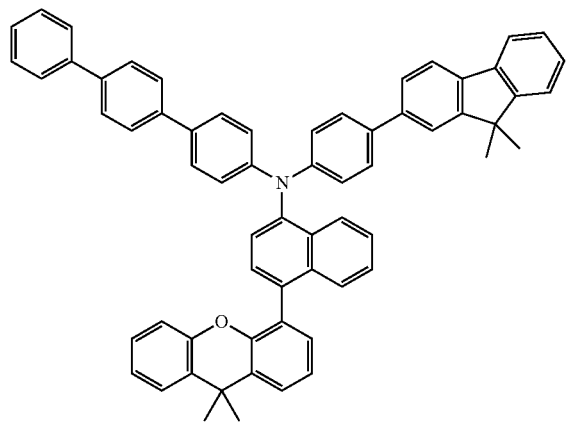
[Chemical Formula 11]
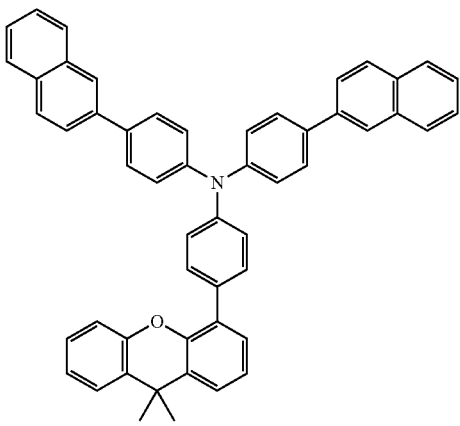
[Chemical Formula 12]
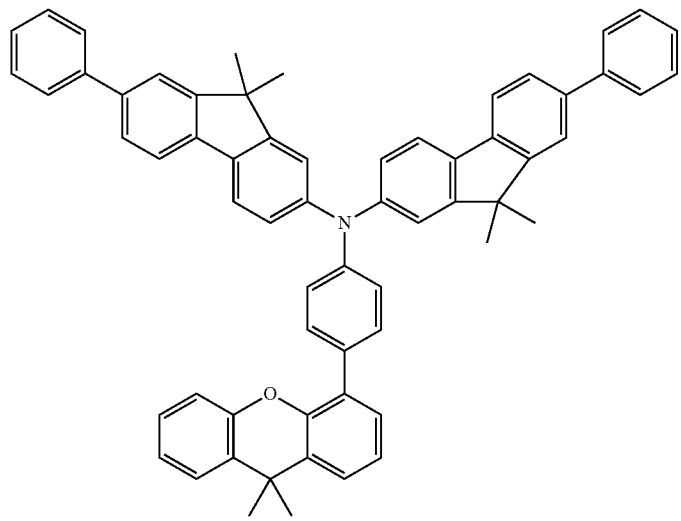

[Chemical Formula 13]
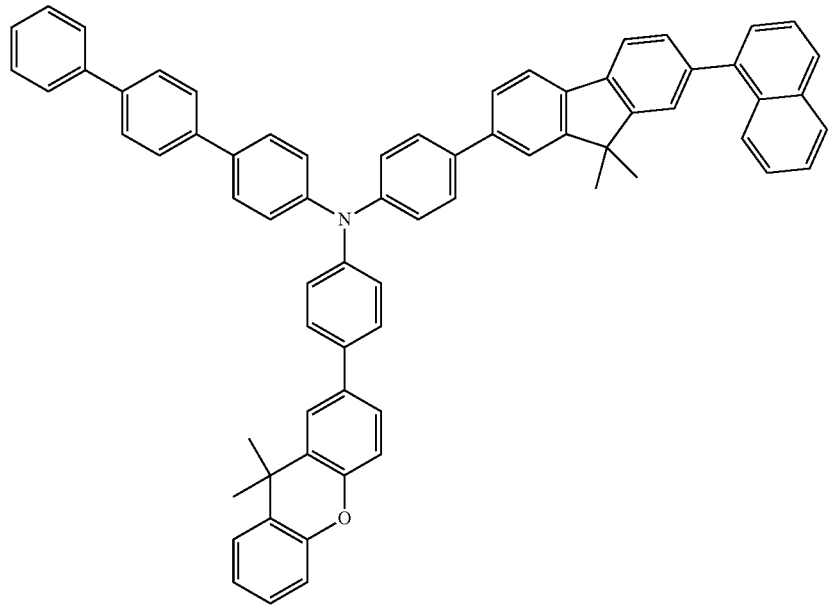
[Chemical Formula 14]
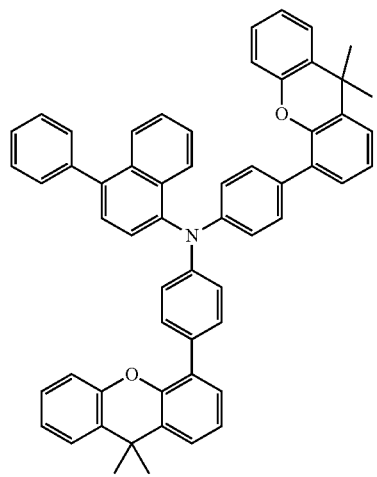
[Chemical Formula 15]
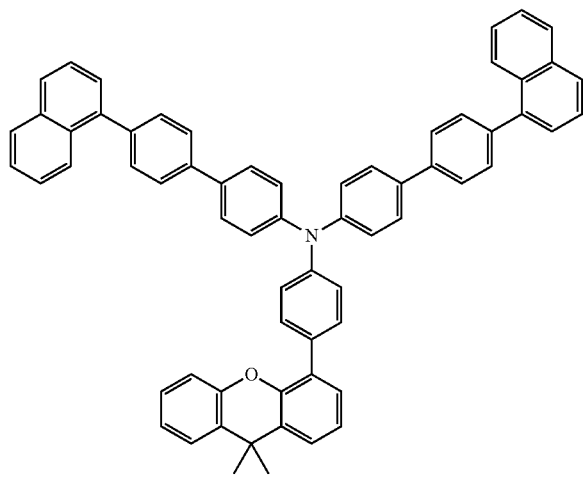
[Chemical Formula 16]
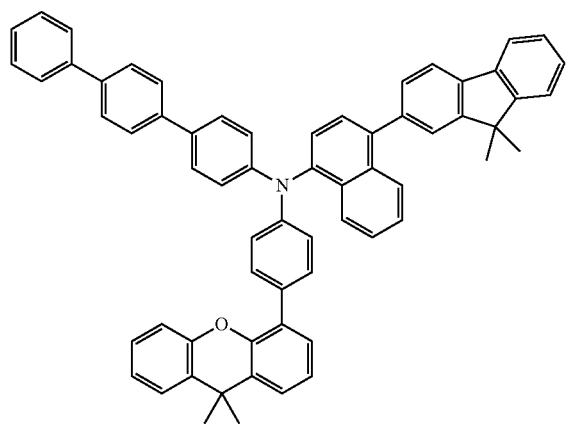
[Chemical Formula 17]
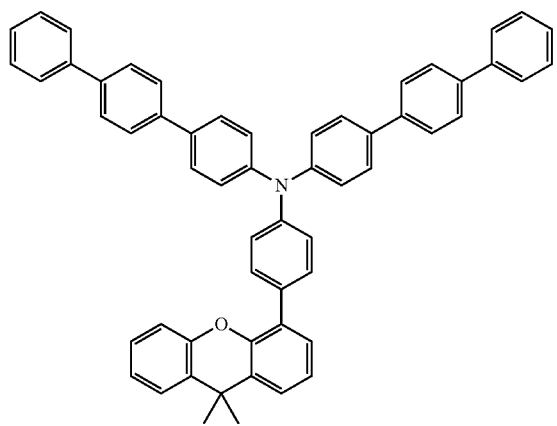

[Chemical Formula 18]
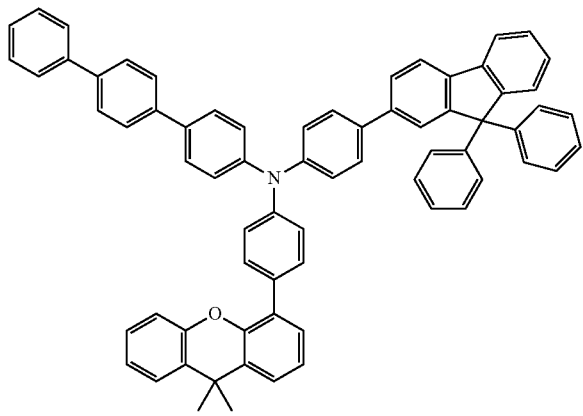
[Chemical Formula 19]
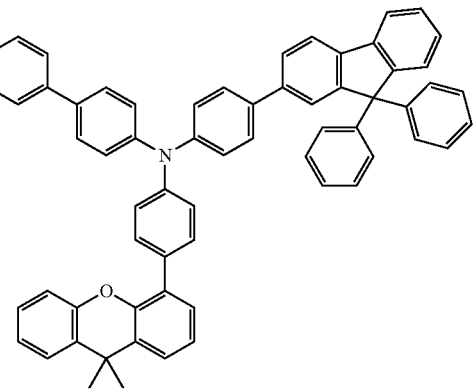
[Chemical Formula 20]
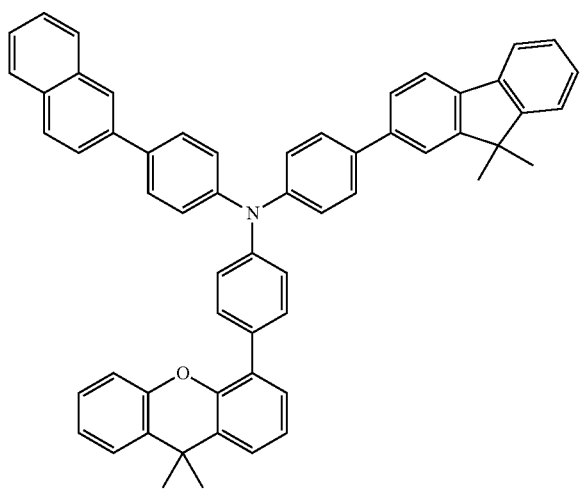
[Chemical Formula 21]
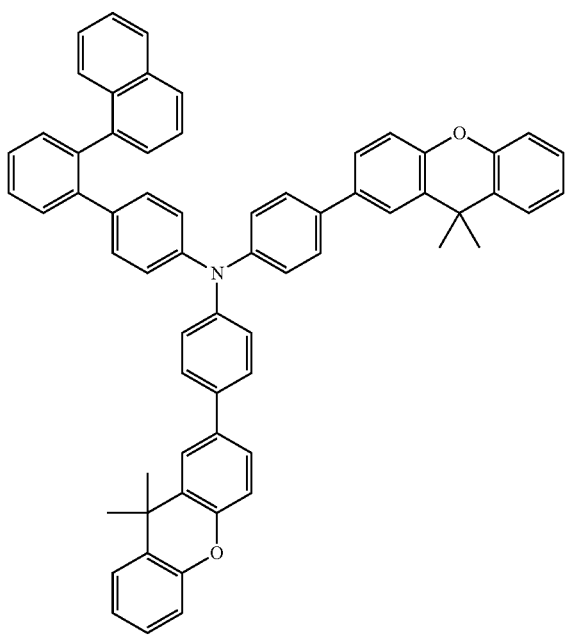

-continued
[Chemical Formula 22]
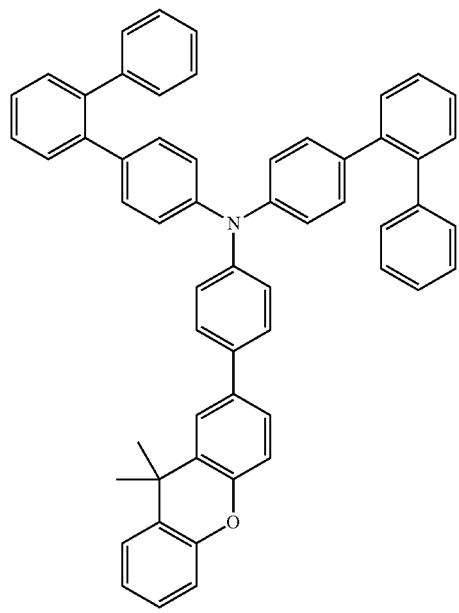
[Chemical Formula 23]
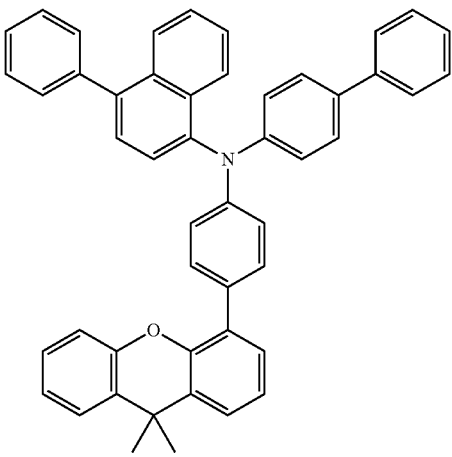
[Chemical Formula 24]
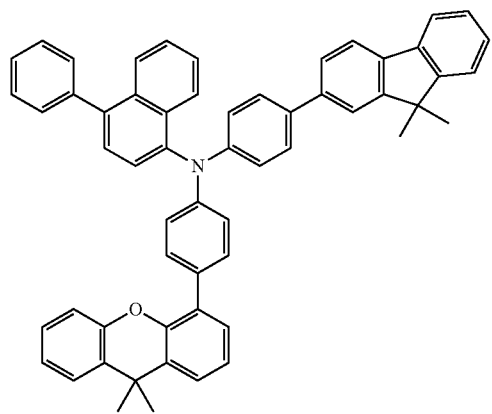
[Chemical Formula 25]
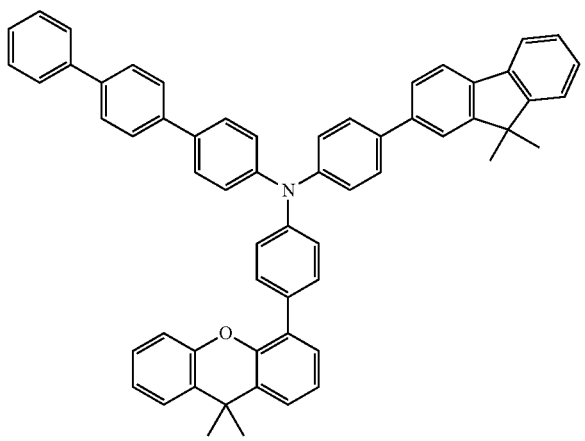
[Chemical Formula 26]
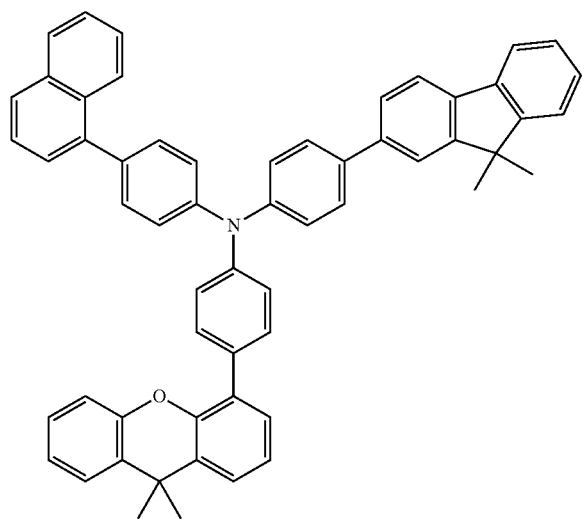

[Chemical Formula 27]
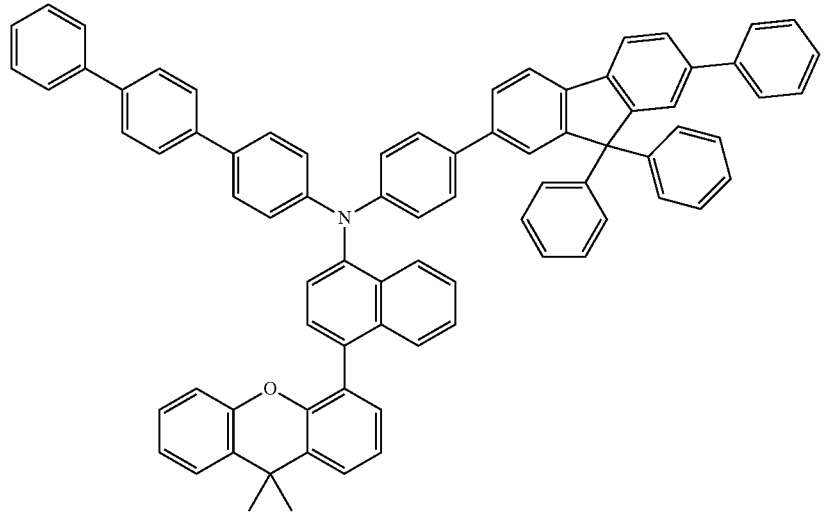
[Chemical Formula 28]
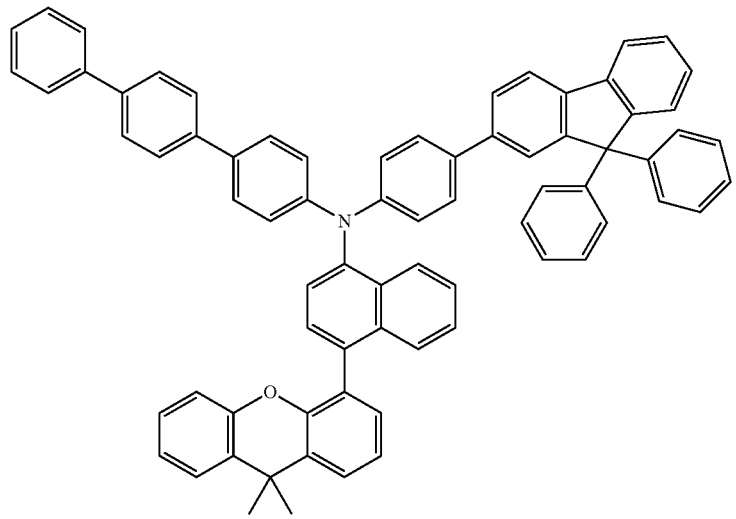
[Chemical Formula 29]
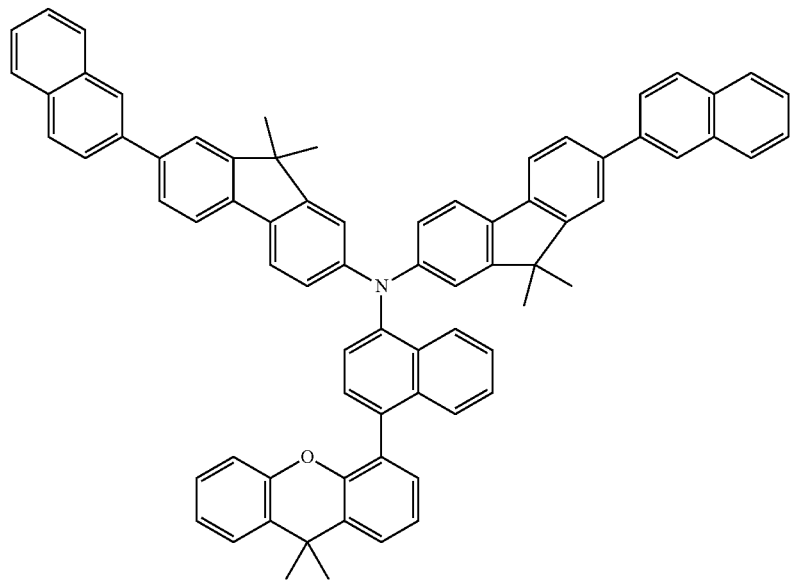

[Chemical Formula 30]
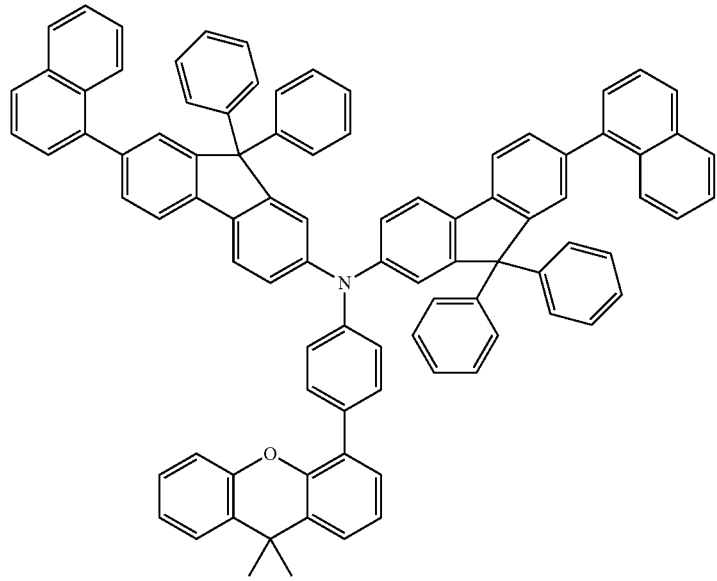
[Chemical Formula 31]
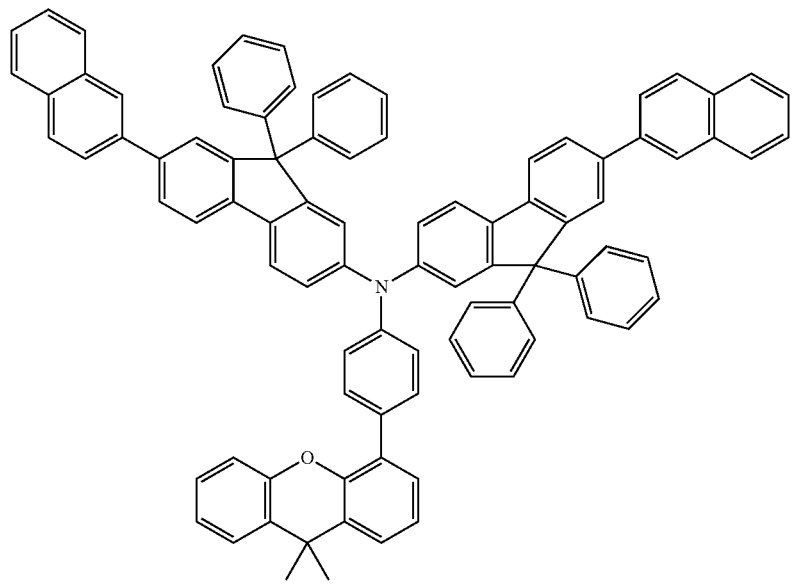
[Chemical Formula 32]
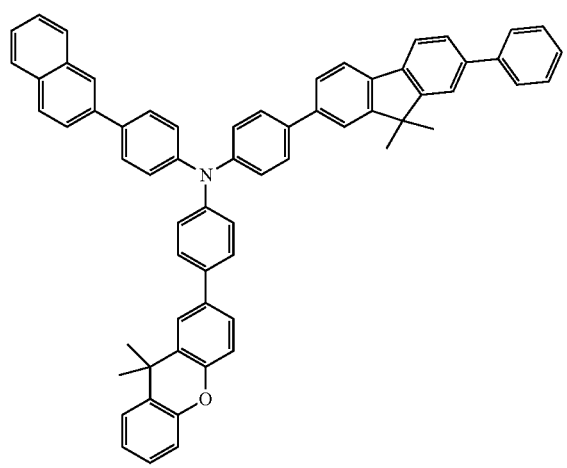
[Chemical Formula 33]
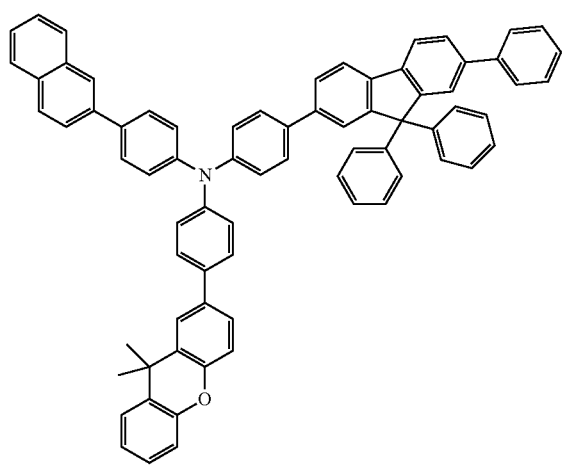

[Chemical Formula 34]
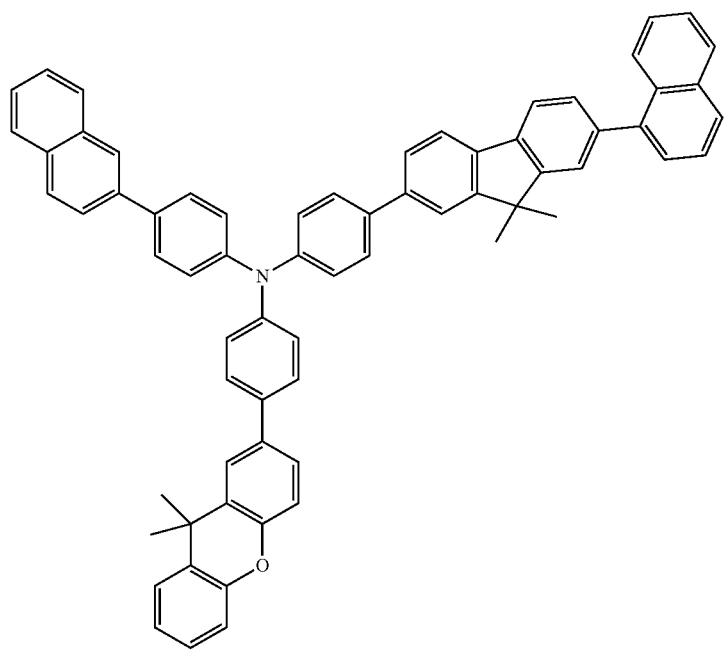
[Chemical Formula 35]
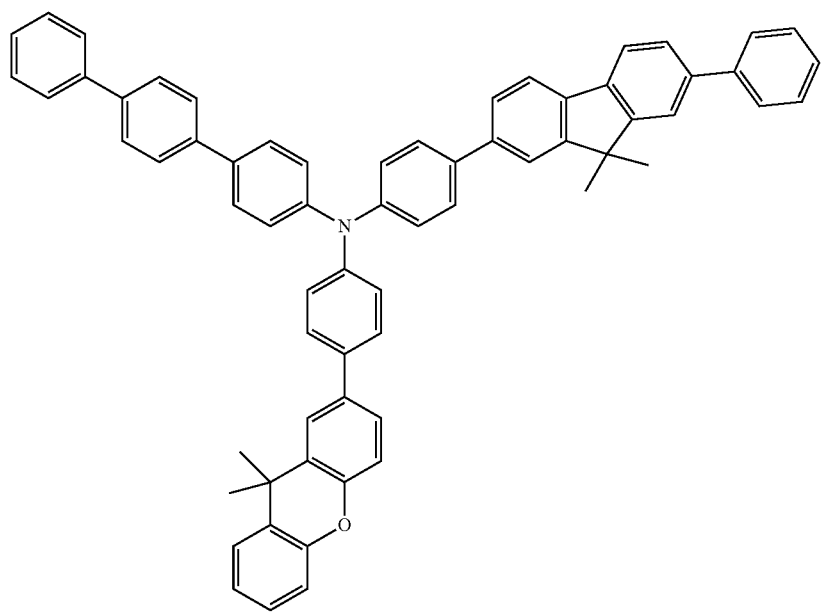

-continued

[Chemical Formula 36]

[Chemical Formula 37]

[Chemical Formula 38]

[Chemical Formula 39]

[Chemical Formula 40]

[Chemical Formula 41]
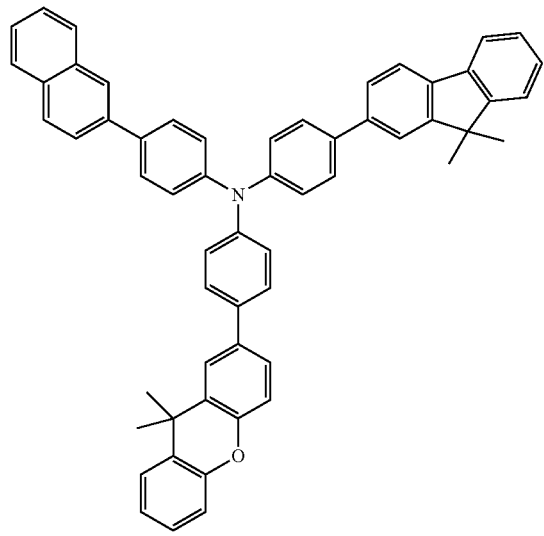
[Chemical Formula 42]
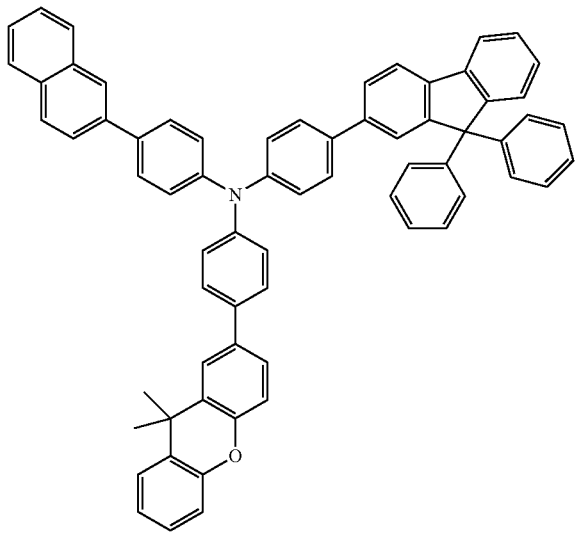
[Chemical Formula 43]
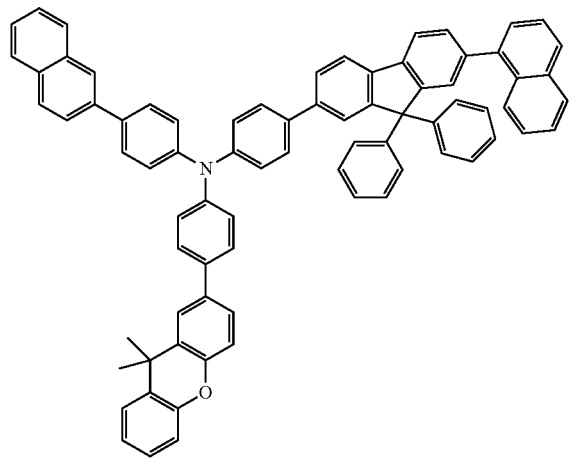
[Chemical Formula 44]
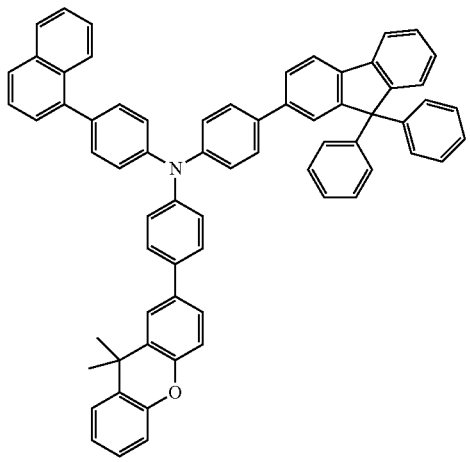
[Chemical Formula 45]
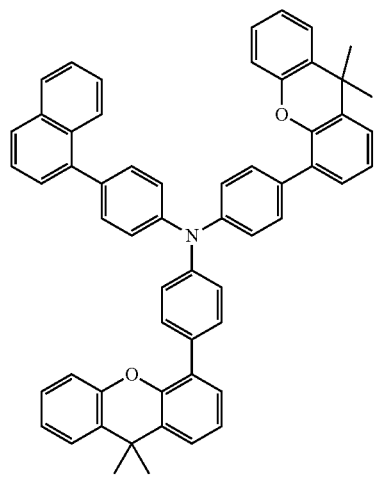
[Chemical Formula 46]
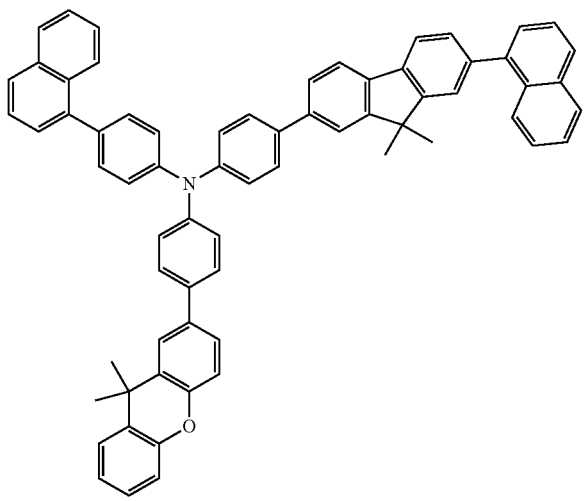

-continued
[Chemical Formula 47]
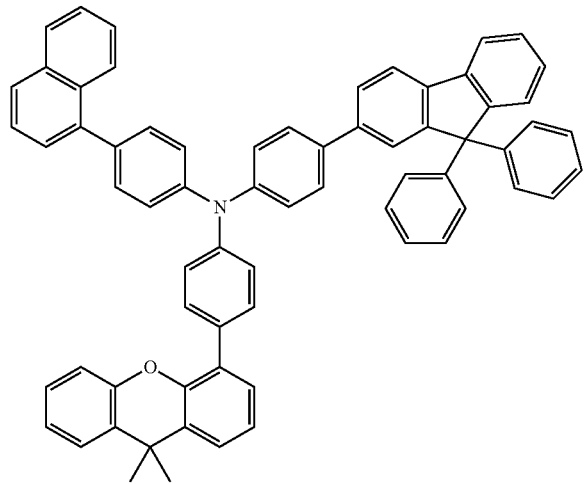
[Chemical Formula 48]
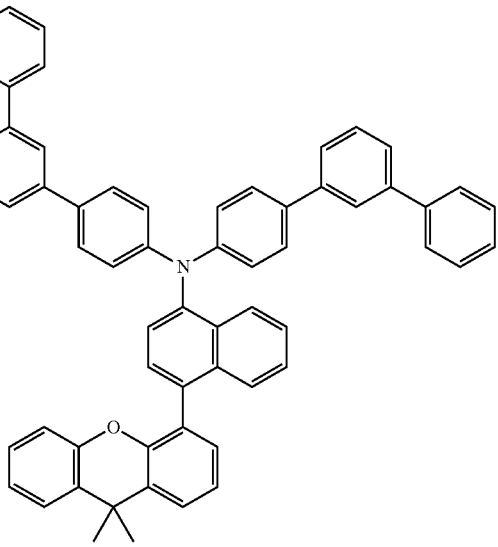
[Chemical Formula 49]
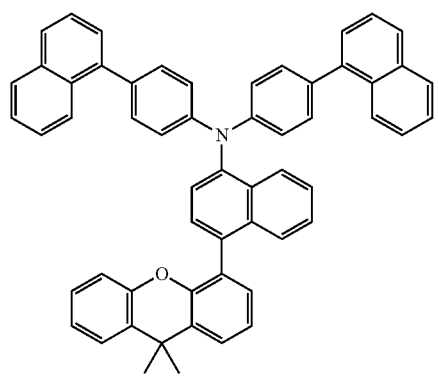
[Chemical Formula 50]
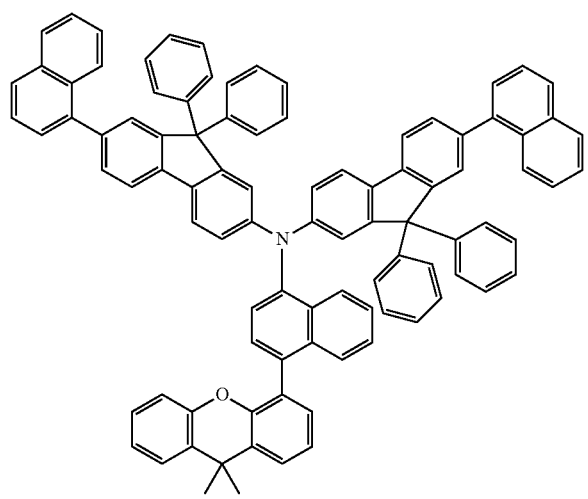

[Chemical Formula 51]
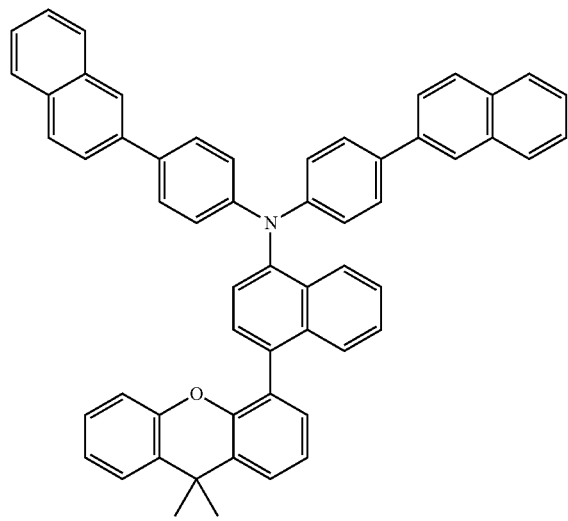
[Chemical Formula 52]
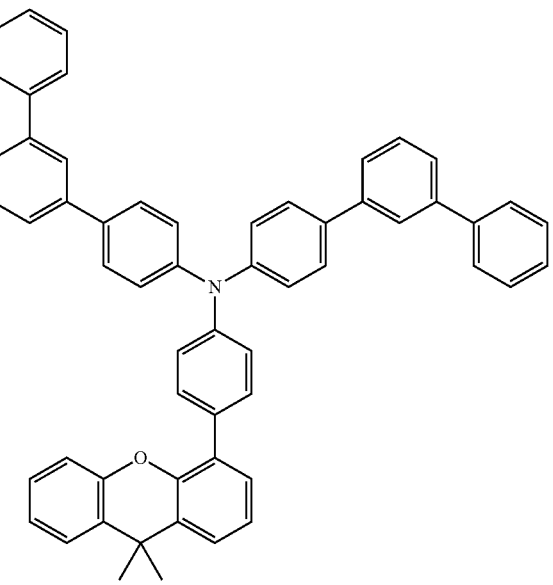
[Chemical Formula 53]
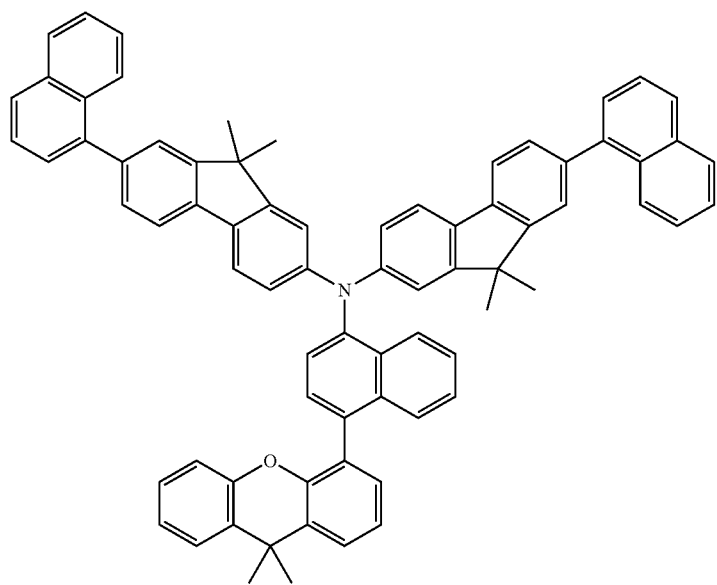

[Chemical Formula 54]
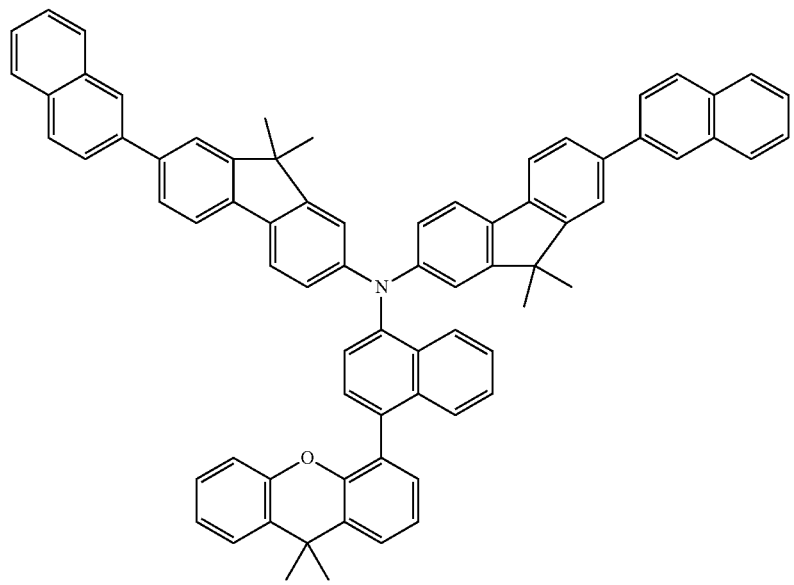
[Chemical Formula 55]
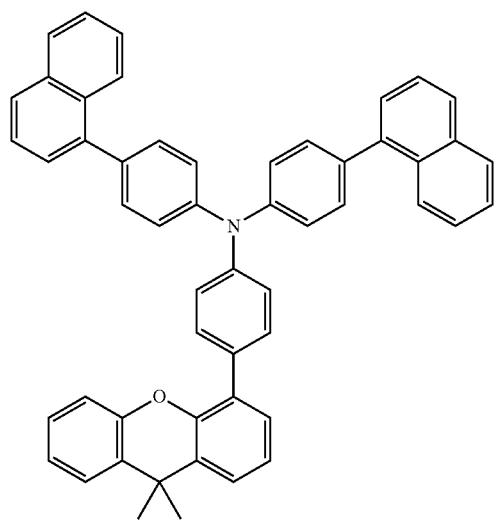
[Chemical Formula 56]
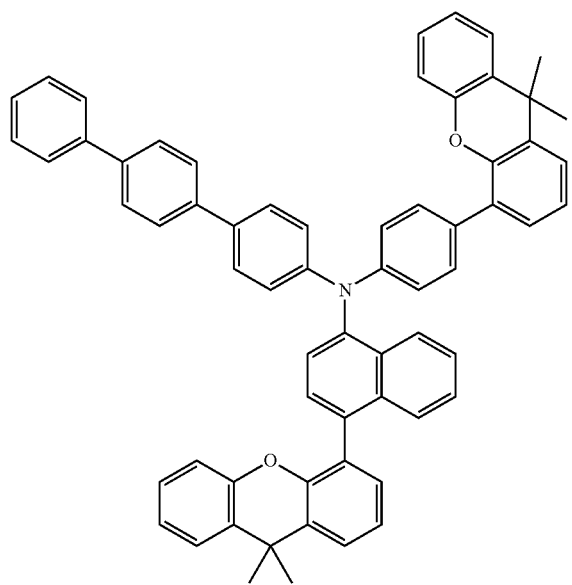

[Chemical Formula 57]
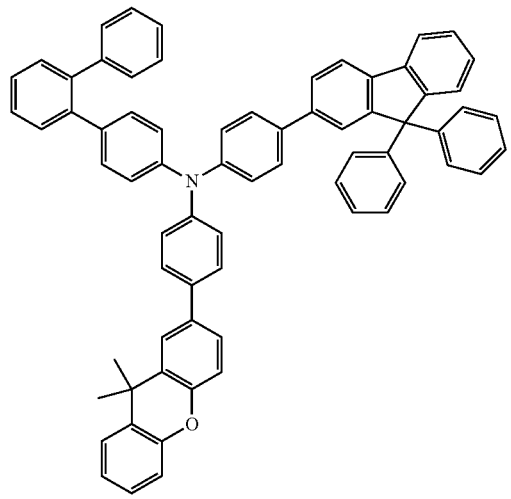
[Chemical Formula 58]
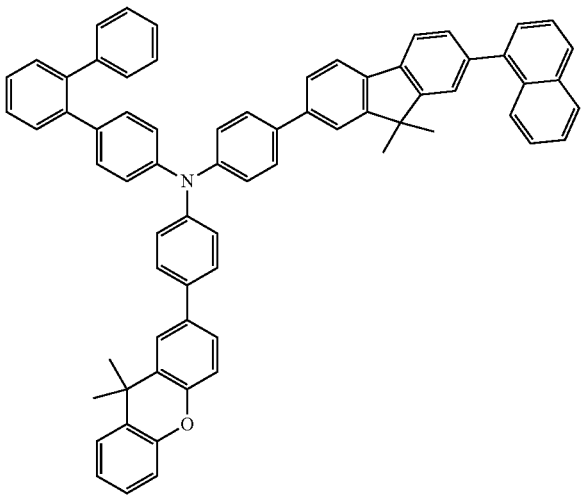
[Chemical Formula 59]
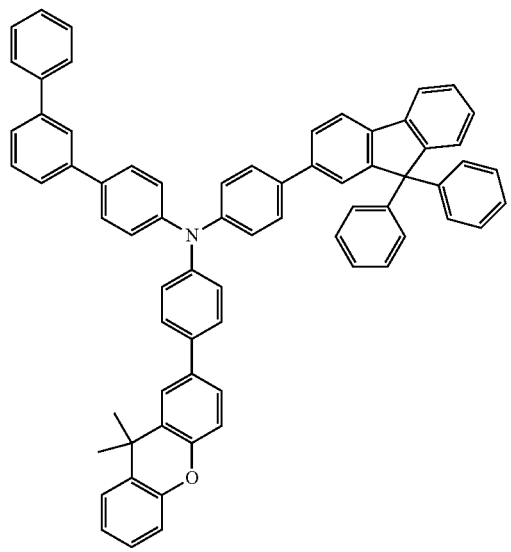
[Chemical Formula 60]
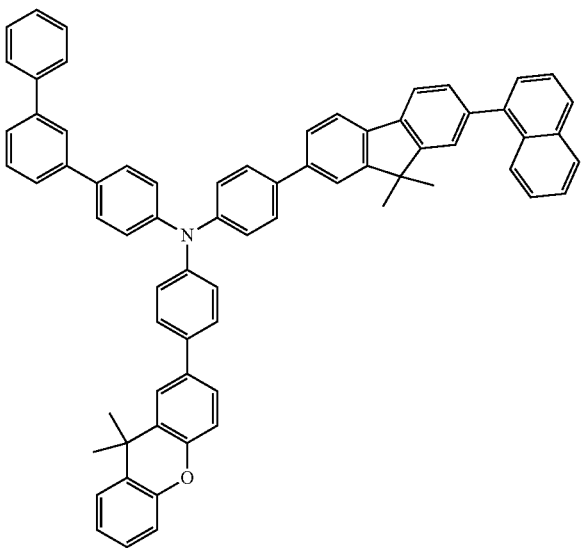
[Chemical Formula 61]
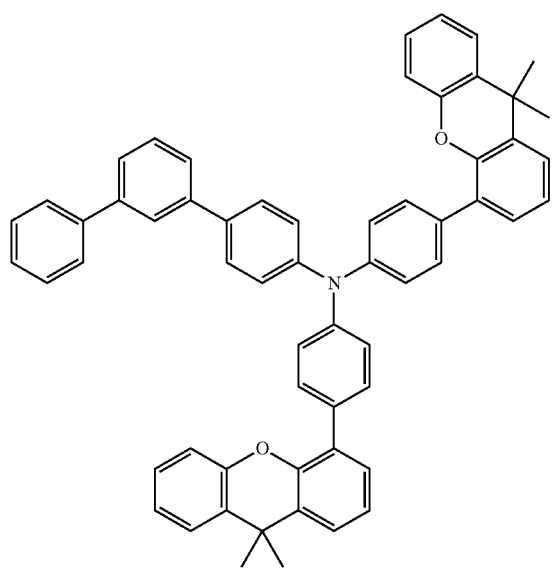
[Chemical Formula 62]
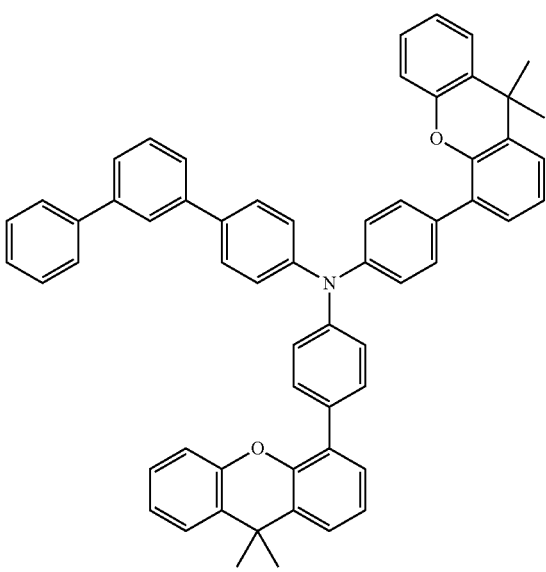

[Chemical Formula 63]
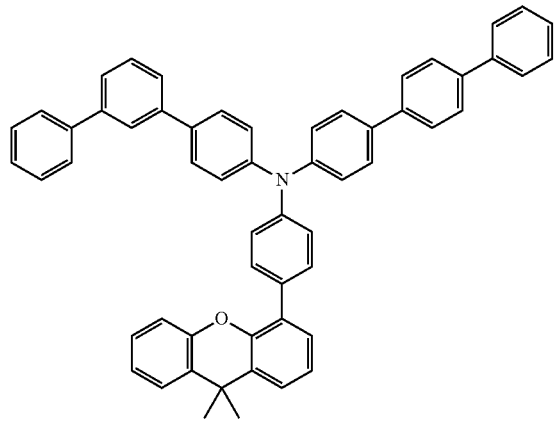
[Chemical Formula 64]
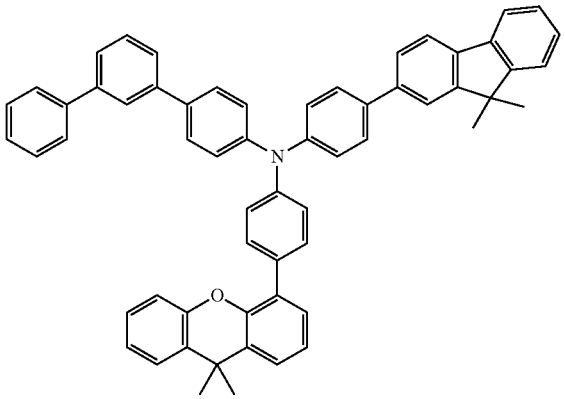
[Chemical Formula 65]
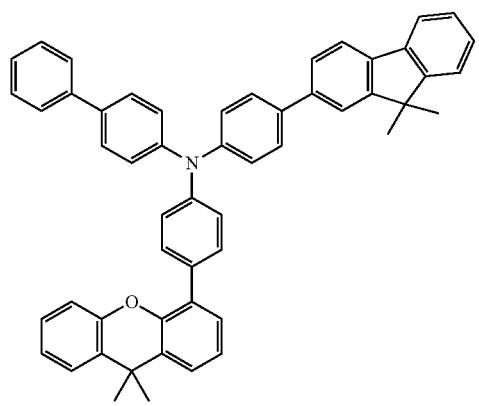
[Chemical Formula 66]
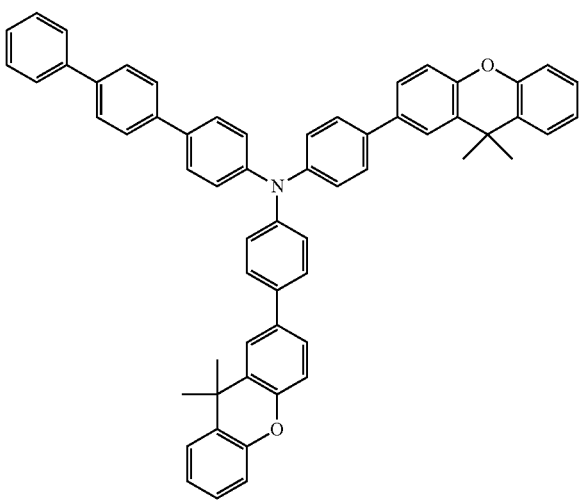
[Chemical Formula 67]
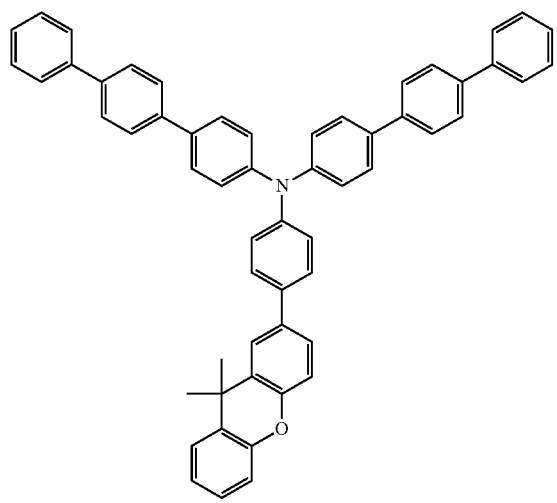
[Chemical Formula 68]
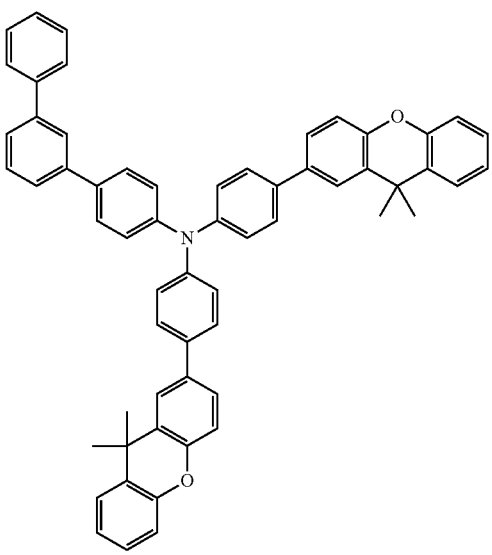

-continued
[Chemical Formula 69]
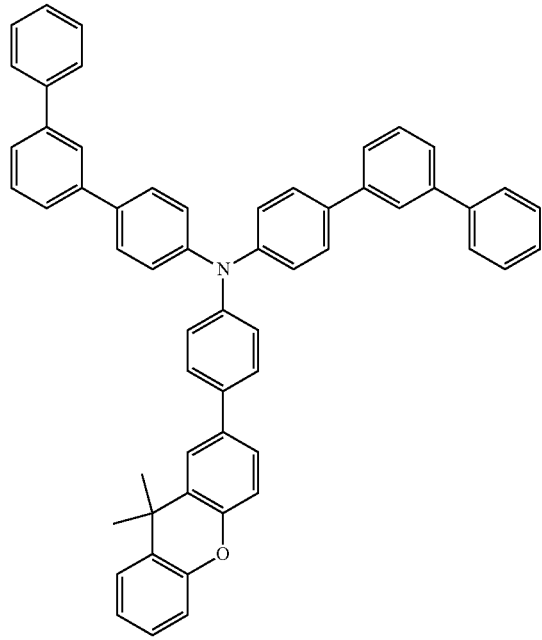
[Chemical Formula 70]
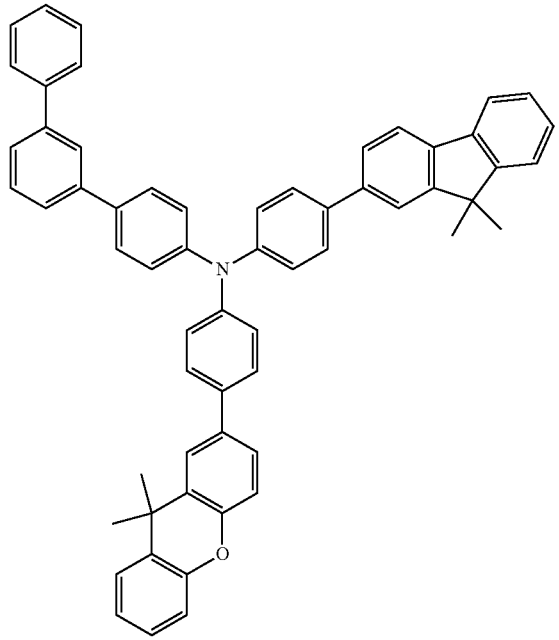
[Chemical Formula 71]
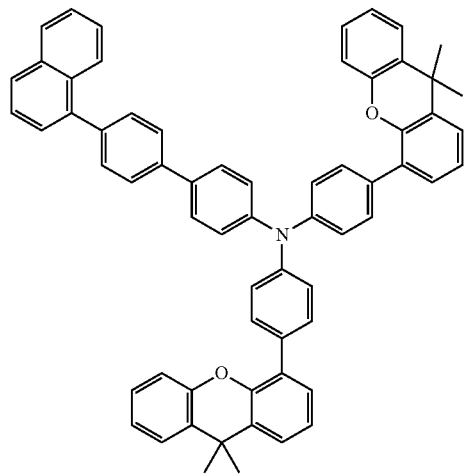
[Chemical Formula 72]
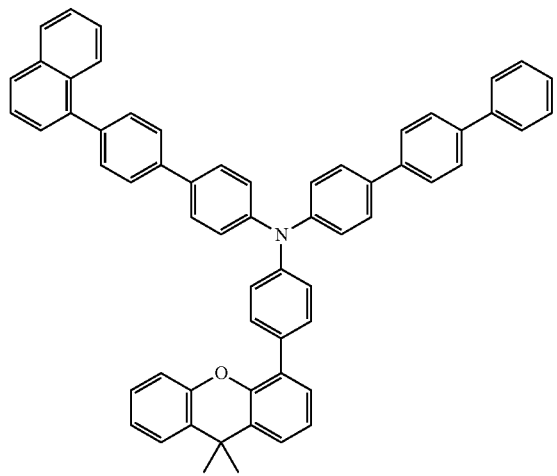
[Chemical Formula 73]
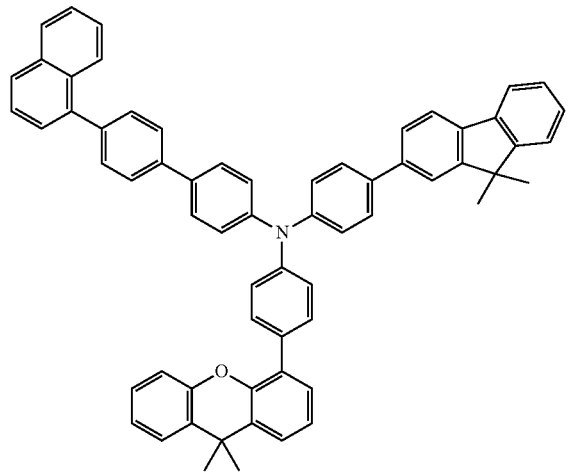
[Chemical Formula 74]
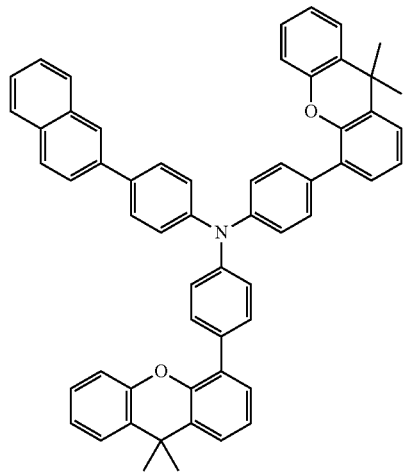

[Chemical Formula 75]
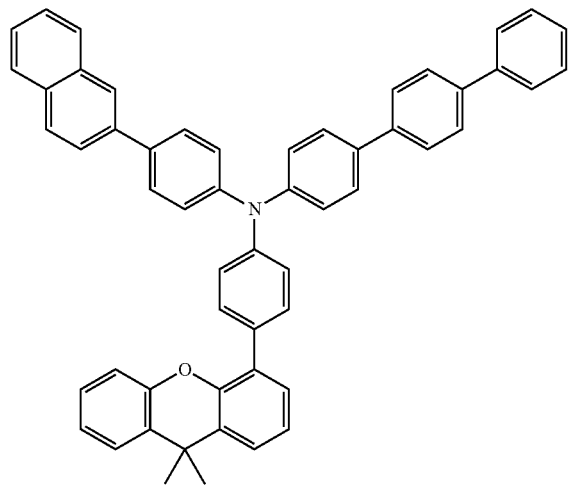
[Chemical Formula 76]
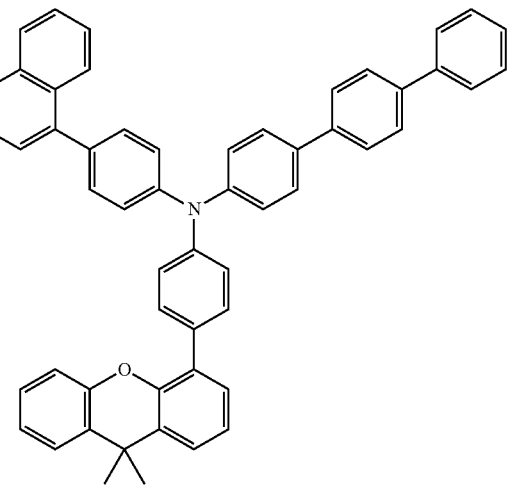
[Chemical Formula 77]
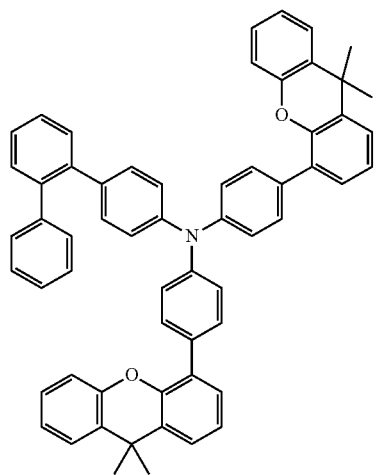
[Chemical Formula 78]
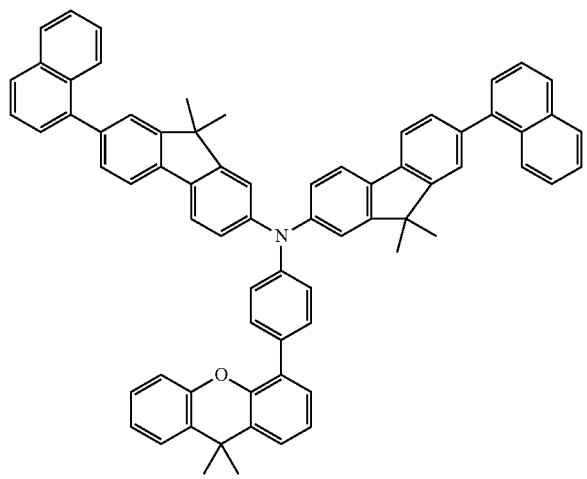
[Chemical Formula 79]
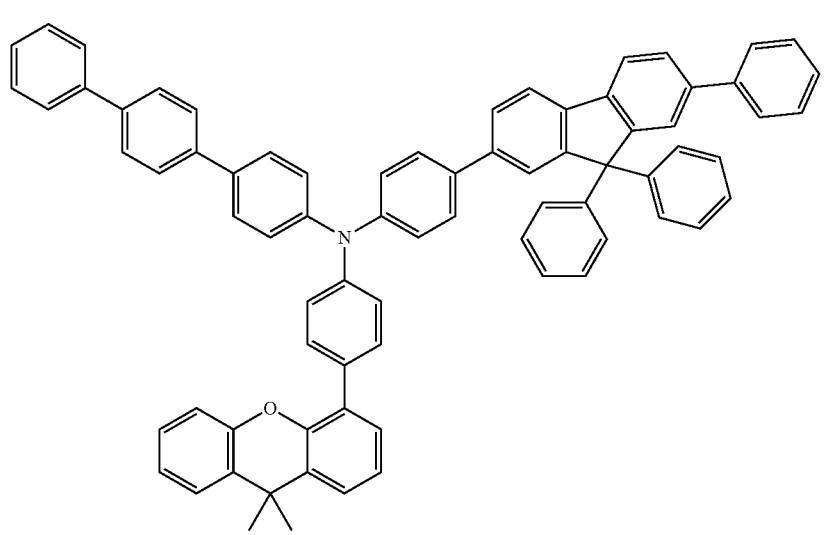

-continued
[Chemical Formula 80]
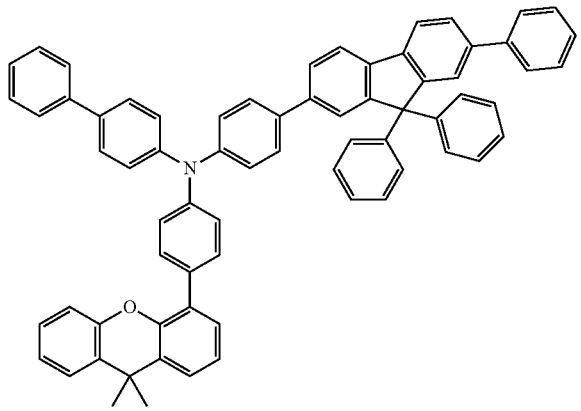
[Chemical Formula 81]
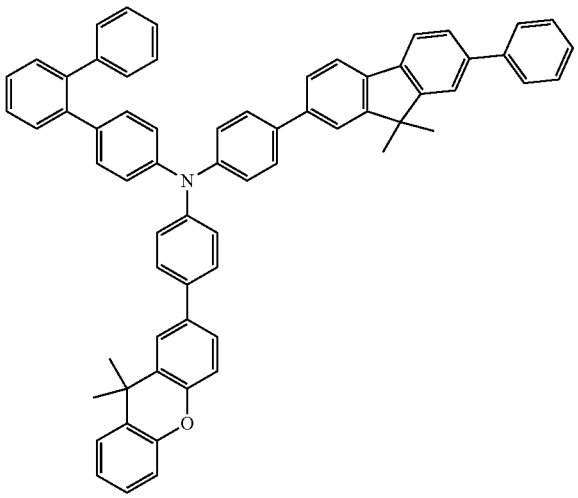
[Chemical Formula 82]
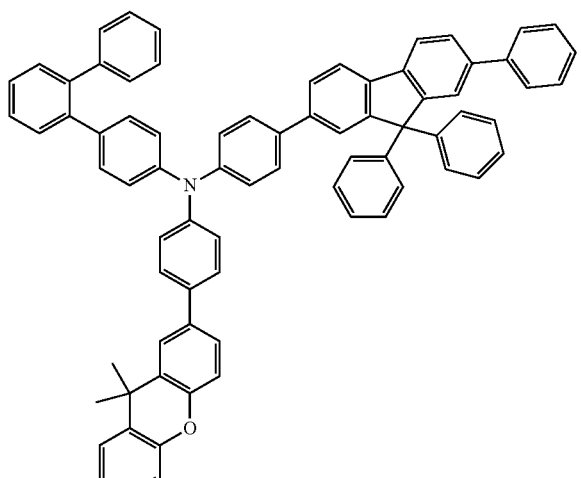
[Chemical Formula 83]
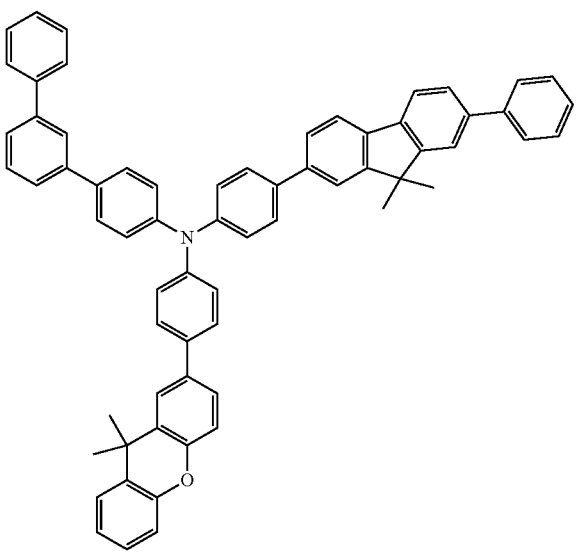
[Chemical Formula 84]
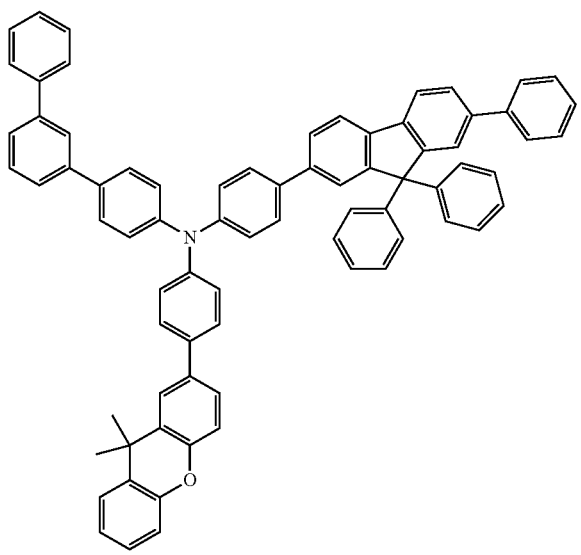
[Chemical Formula 85]
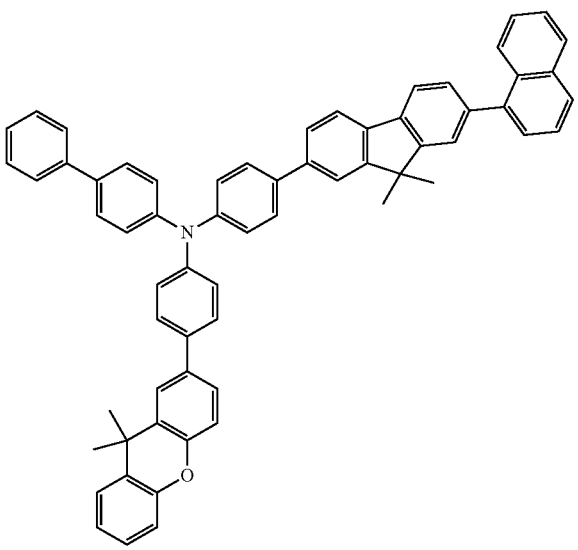

-continued
[Chemical Formula 86]
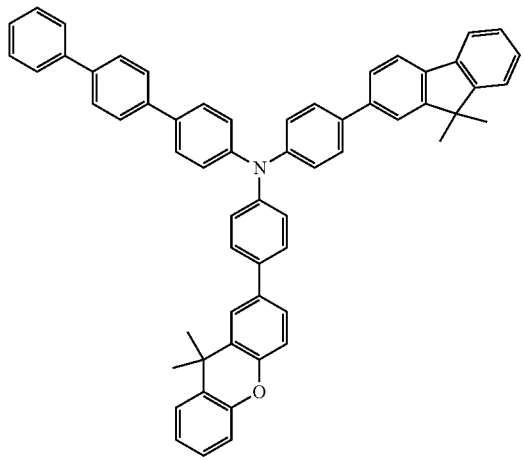
[Chemical Formula 87]
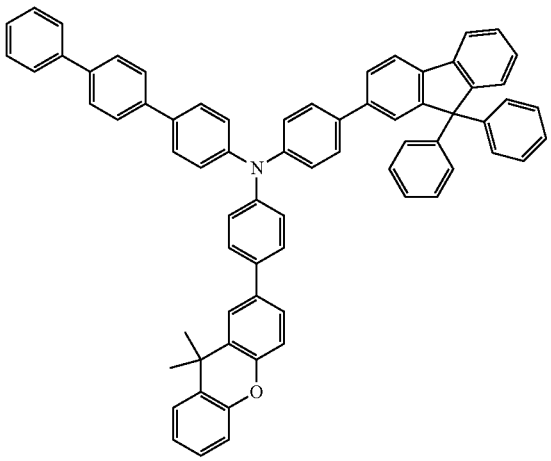
[Chemical Formula 88]
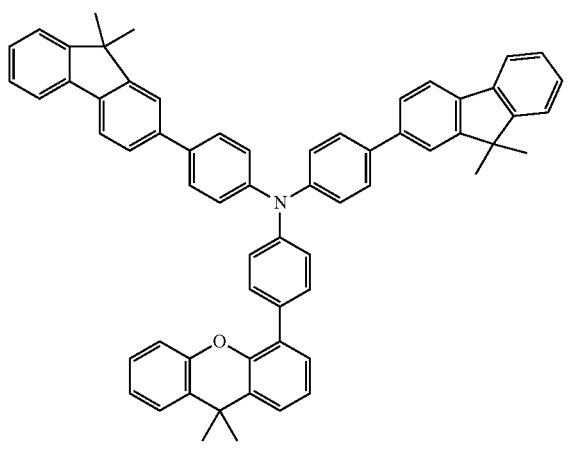
[Chemical Formula 89]
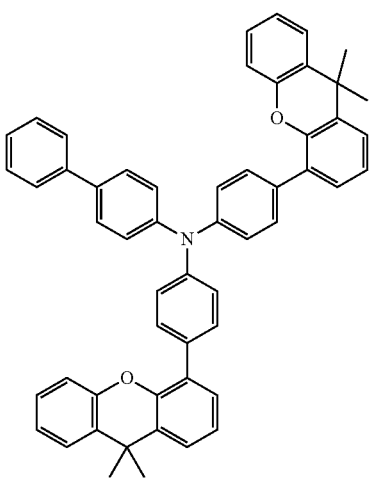
[Chemical Formula 90]
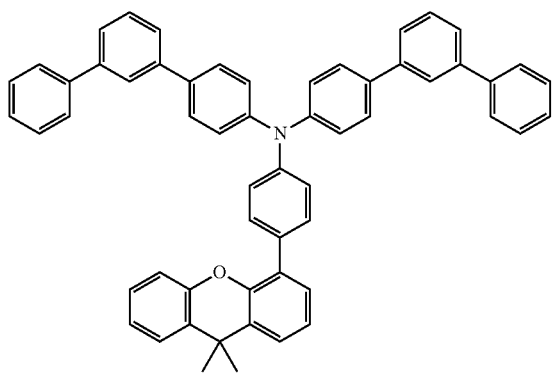
[Chemical Formula 91]
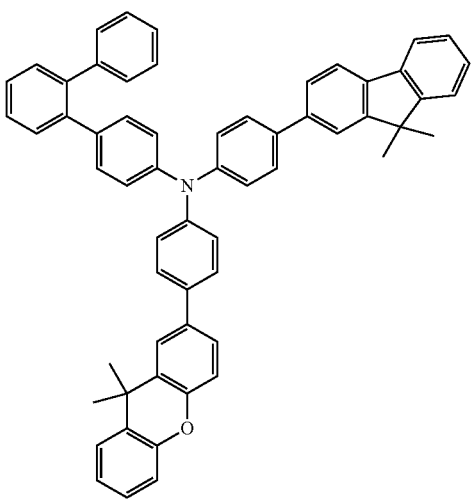

[Chemical Formula 92]
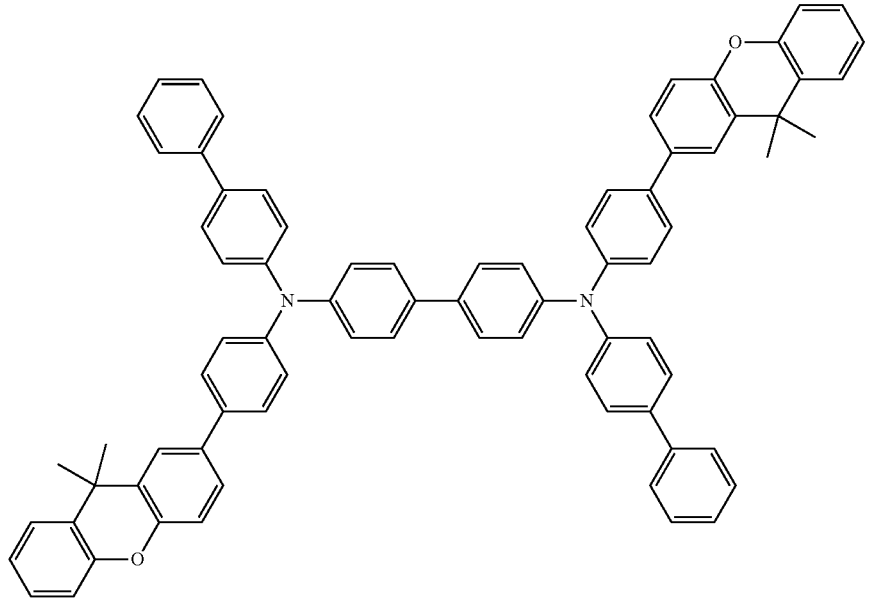
[Chemical Formula 93]
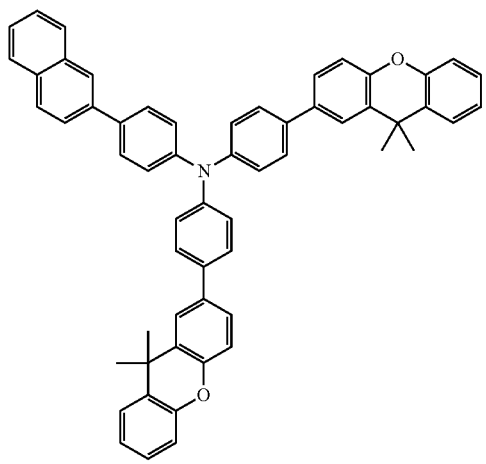
[Chemical Formula 94]
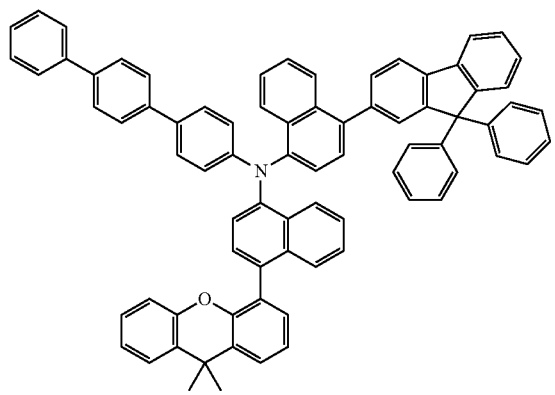
[Chemical Formula 95]
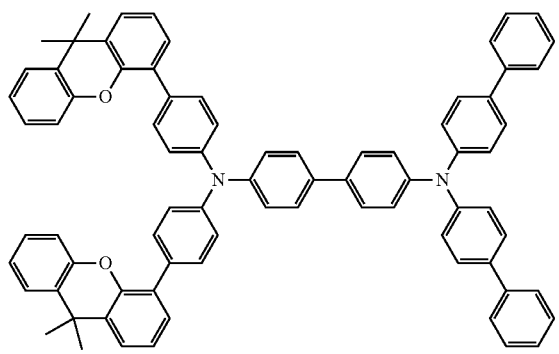
[Chemical Formula 96]
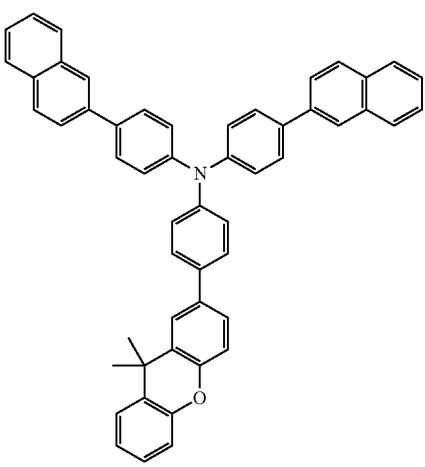

-continued
[Chemical Formula 97]
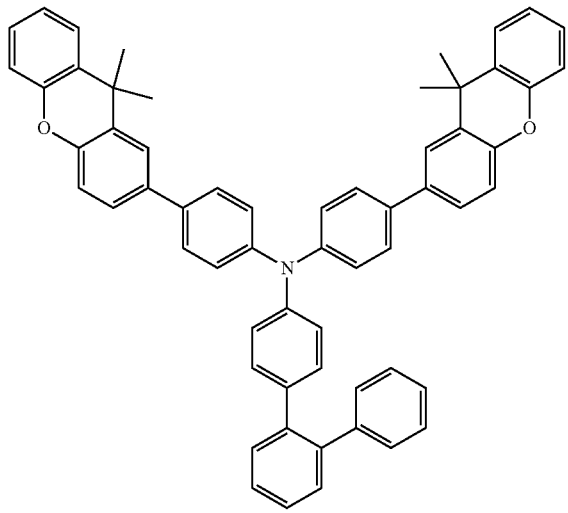
[Chemical Formula 98]
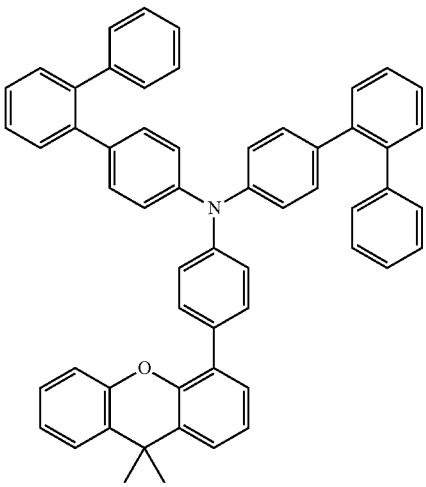
[Chemical Formula 99]
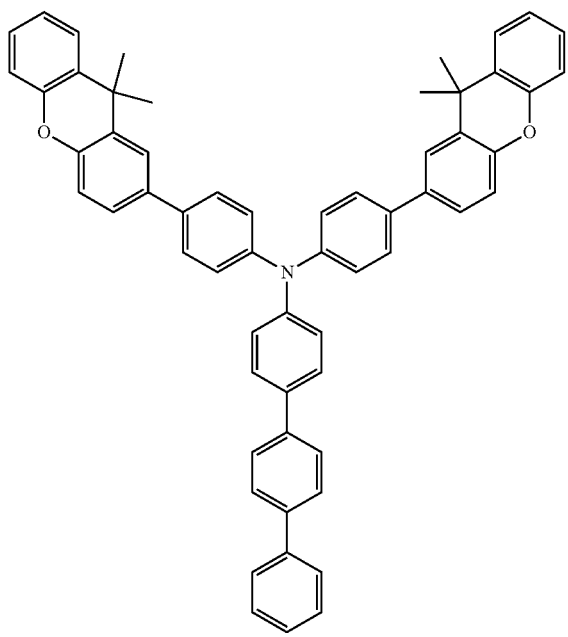
[Chemical Formula 100]
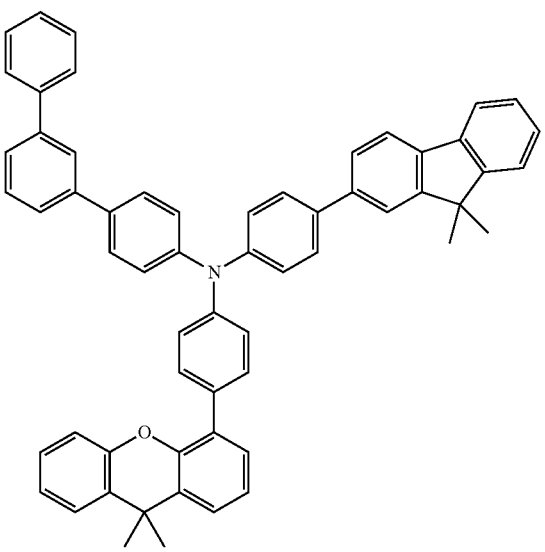
[Chemical Formula 101]
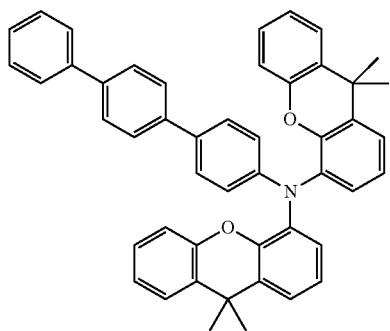
[Chemical Formula 102]
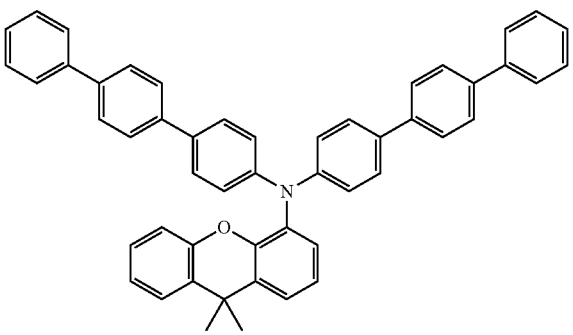

[Chemical Formula 103]
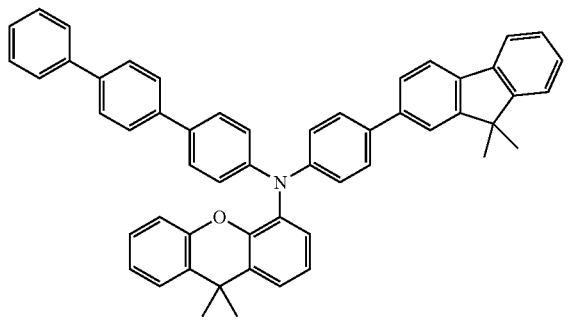
[Chemical Formula 104]
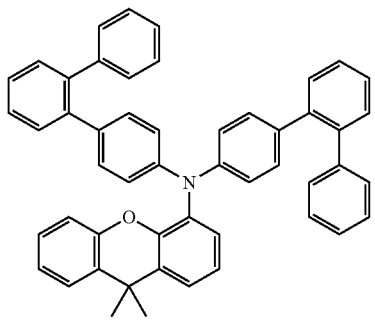
[Chemical Formula 105]
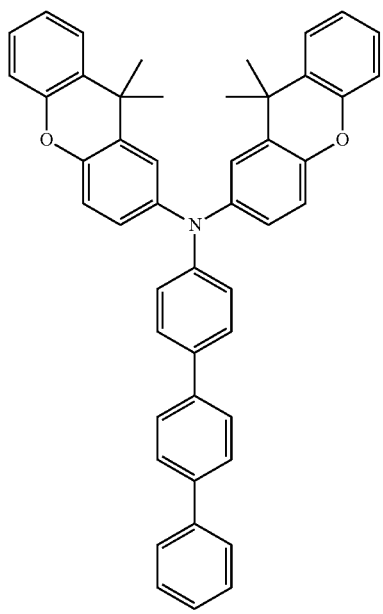
[Chemical Formula 106]
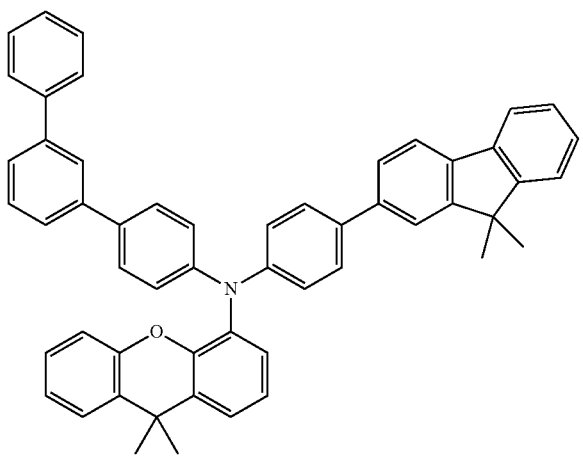
[Chemical Formula 107]
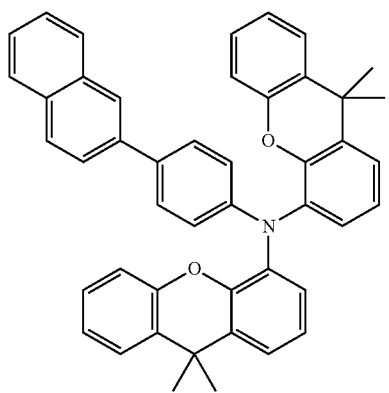
[Chemical Formula 108]
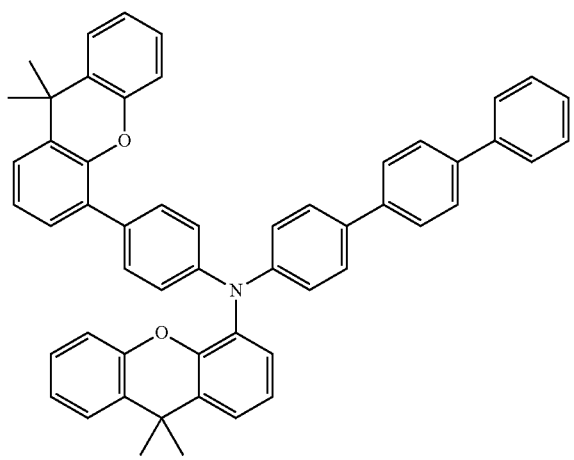

[Chemical Formula 109]
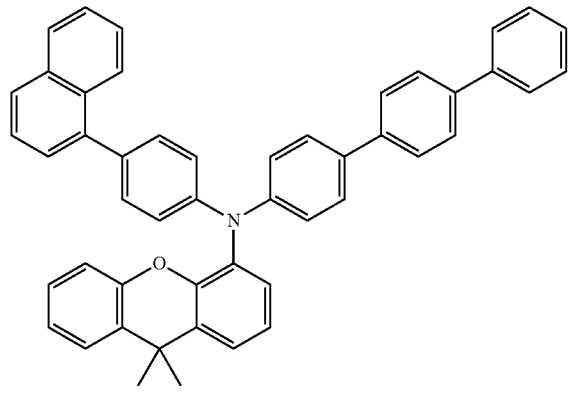
[Chemical Formula 110]
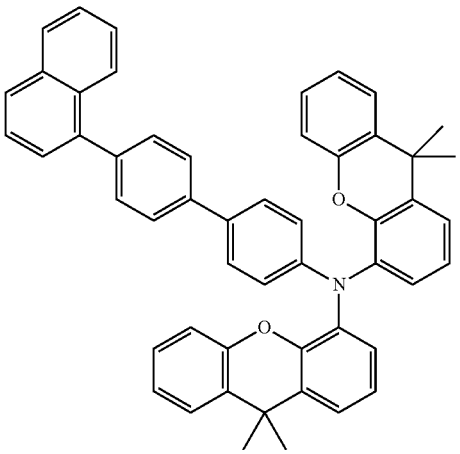
[Chemical Formula 111]
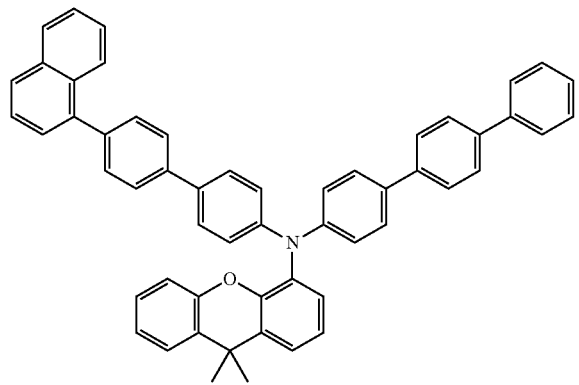
[Chemical Formula 112]
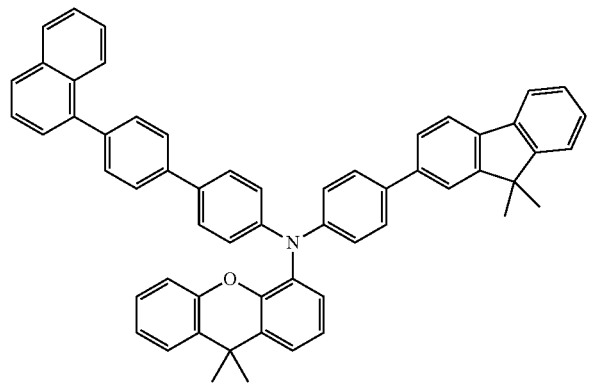
[Chemical Formula 113]
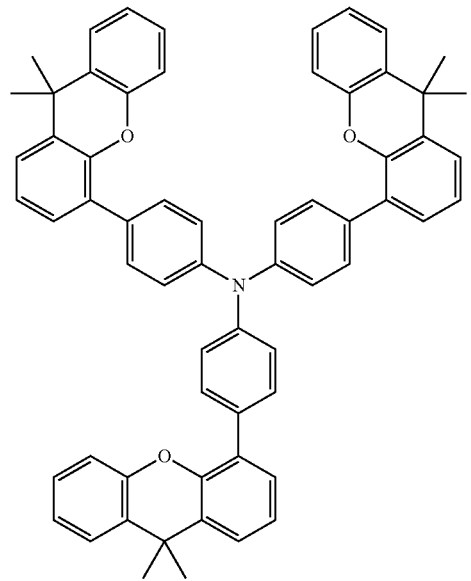
[Chemical Formula 114]
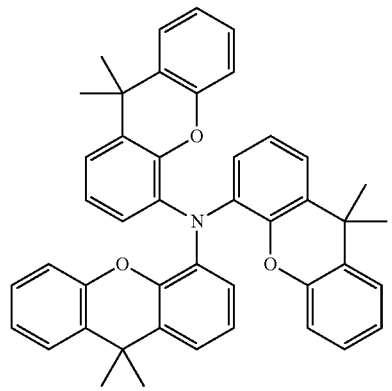

-continued
[Chemical Formula 115]
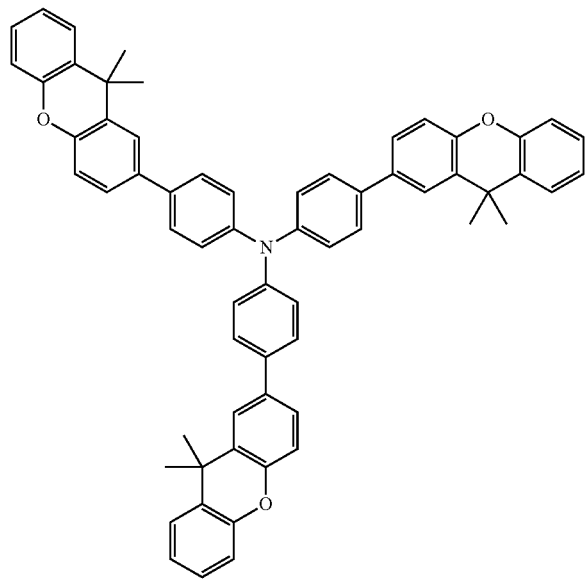
[Chemical Formula 116]
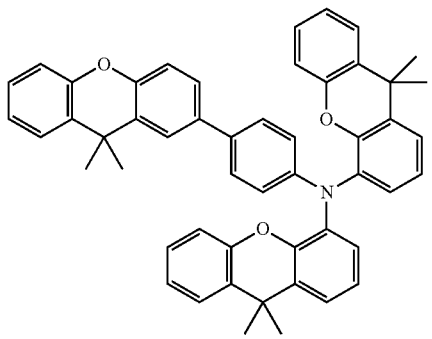
[Chemical Formula 117]
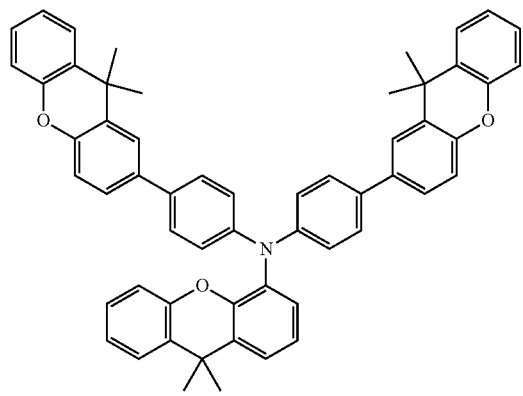
[Chemical Formula 118]
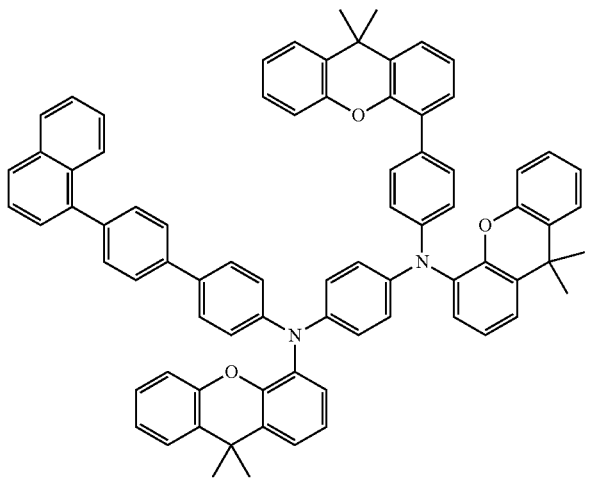
[Chemical Formula 119]
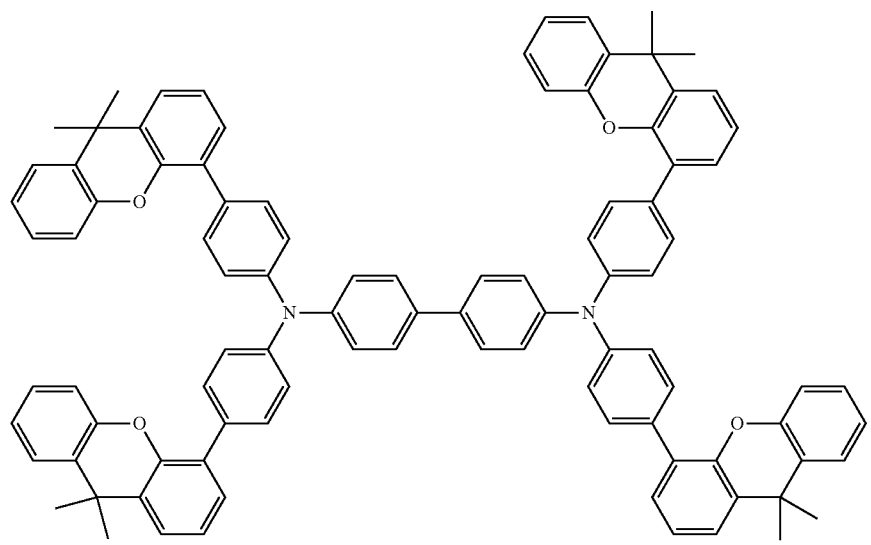

[Chemical Formula 120]

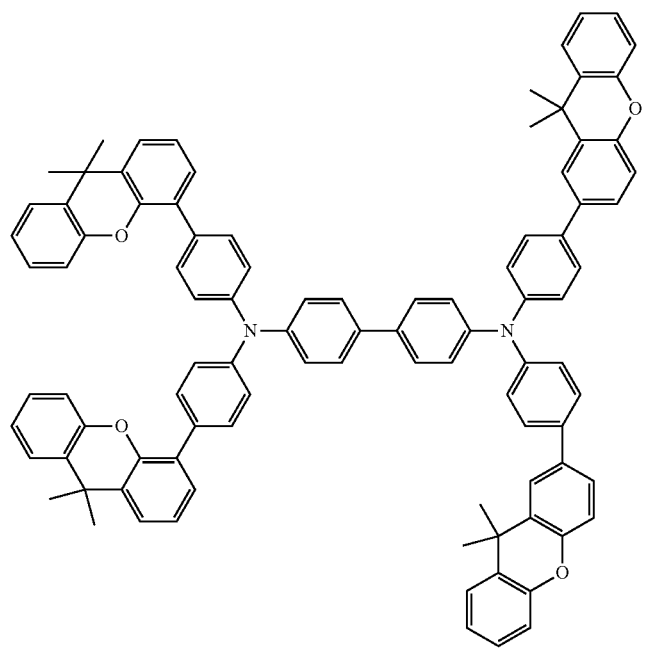

In another aspect, the present disclosure provides an organic electroluminescent device including at least one of the various compounds represented by [Chemical Formula 1]. The organic electroluminescent device includes: a first electrode; a second electrode; and an organic layer disposed between the first electrode and the second electrode, wherein the organic layer includes at least one organic electroluminescent compound(s) represented by [Chemical Formula 1].

The organic layer may be a single layer or a plurality of layers including an electroluminescent layer and may further include a hole injection layer, a hole transport layer, an electroluminescent layer, an electron blocking layer, a hole blocking layer, an electron transport layer and an electron injection layer. In an exemplary embodiment, the hole transport layer include at least one of the organic electroluminescent compound(s) represented by [Chemical Formula 1].

In an exemplary embodiment of the present disclosure, the electroluminescent layer may include at least one dopant compound(s) in addition to the compound(s) represented by [Chemical Formula 1].

In an exemplary embodiment of the present disclosure, the electroluminescent layer may include at least one host compound(s) in addition to the compound(s) represented by [Chemical Formula 1].

The organic electroluminescent device according to the present disclosure may include at least one organic electroluminescent layer(s) including a red-, green- or blue-emitting compound. Through this, a white-emitting organic electroluminescent device may be achieved. The organic electroluminescent layer may include a host compound and a dopant compound.

The electron transport layer used in the organic electroluminescent device according to the present disclosure serves to sufficiently transport electrons from a cathode to the organic electroluminescent layer and prevent the transport of holes that have not recombined in the organic electroluminescent layer, thereby increasing the chance of recombination.

The material of the electron transport layer may be any one commonly used in the art without particular limitation. For example, oxadiazole derivatives such as PBD, BMD, BND, $Alq_3$, etc. may be used.

On the electron transport layer, an electron injection layer (EIL) may be further formed to facilitate injection of electrons from the cathode, thereby improving power efficiency. The material of the electron injection layer may also be any one commonly used in the art without particular limitation. For example, LiF, NaCl, CsF, $Li_2O$, BaO, etc. may be used.

FIG. 1 is a cross-sectional view of an organic electroluminescent device of the present disclosure. The organic electroluminescent device according to the present disclosure includes an anode 20, a hole transport layer 40, an organic electroluminescent layer 50, an electron transport layer 60 and a cathode 80 and, if necessary, may further include a hole injection layer 30 and an electron injection layer 70. Also, one or more intermediate layer(s) may be further formed and a hole blocking layer or an electron blocking layer may be further formed.

The organic electroluminescent (EL) device of the present disclosure and a method for manufacturing same will be described in detail referring to FIG. 1. First, an anode 20 is formed by coating an anode electrode material on a substrate 10. The substrate 10 may be a substrate commonly used in an organic EL device. Specifically, an organic substrate or a transparent plastic substrate superior in terms of transparency, surface roughness, easiness of handling, waterproofing property, etc. may be used. And, the anode electrode material may be indium tin oxide (ITO), indium zinc oxide (IZO), tin oxide ($SnO_2$), zinc oxide (ZnO), etc. having superior transparency and conductivity.

A hole injection layer 30 is formed on the anode 20 and then a hole transport layer 40 is formed on the hole injection layer 30. The hole injection layer or the hole transport layer is formed from the organic electroluminescent compound according to the present disclosure through vacuum thermal evaporation or spin coating.

Then, an organic electroluminescent layer 50 is formed on the hole transport layer 40 and, optionally, a hole blocking layer (not shown) may be formed on the organic electroluminescent layer 50 by vacuum deposition or spin coating. The hole blocking layer includes a material having a very low highest occupied molecular orbital (HOMO) level to prevent the problem of decreased lifetime and efficiency of the device resulting from passage of holes to the cathode through the organic electroluminescent layer. The hole blocking material is not particularly limited as long as it is capable of transporting electrons and having a higher ionization potential than the electroluminescent compound. Typically, BAlq, BCP, TPBI, etc. may be used.

After depositing an electron transport layer 60 on the hole blocking layer by vacuum deposition or spin coating, an electron injection layer 70 s formed. Then, a cathode 80 is formed on the electron injection layer 70 from a metal for forming a cathode through vacuum thermal evaporation, thereby completing the organic EL device. The metal for forming a cathode may be lithium (Li), magnesium (Mg), aluminum (Al), aluminum-lithium (Al—Li), calcium (Ca), magnesium-indium (Mg—In), magnesium-silver (Mg—Ag), etc. To obtain a transparent electroluminescent device, a transparent cathode using ITO or IZO may be used.

In another exemplary embodiment of the present disclosure, at least one layer(s) selected from the hole injection layer, the hole transport layer, the electron blocking layer, the electroluminescent layer, the hole blocking layer, the electron transport layer and the electron injection layer may be formed by single molecule deposition or solution process, and the organic electroluminescent device according to the present disclosure may be used as a display device or a monochromatic or white illumination device.

Hereinafter, the present disclosure will be described in more detail through examples. However, the following examples are for illustrative purposes only and not intended to limit the scope of this disclosure.

Synthesis Example 1

Synthesis of Compound of Chemical Formula 8

Synthesis Example 1-1

Synthesis of Compound <1-a>

Compound <1-a> was synthesized according to Scheme 1.

[Scheme 1]

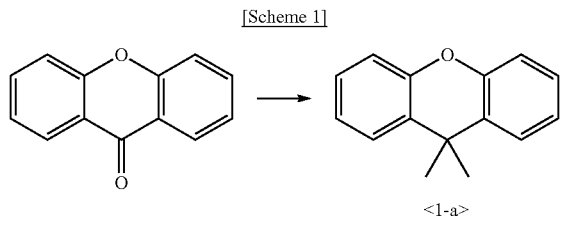

<1-a>

Xanthone (100 g, 0.51 mol) and toluene (600 mL) were added to a 2-L flask and stirred. At 0° C., trimethylaluminum (612 mL, 1.22 mol) was slowly added dropwise and the mixture was stirred at 0° C. for about 1 hour. After stirring at room temperature for 4 hours, 6 N HCl aqueous solution (500 mL) was slowly added dropwise at −40° C. After stirring for about 30 minutes, the mixture was extracted with ethyl acetate. The product was separated by column chromatography to obtain compound <1-a> (110 g, yield: 98%).

Synthesis Example 1-2

Synthesis of Compound <1-b>

Compound <1-b> was synthesized according to Scheme 2.

[Scheme 2]

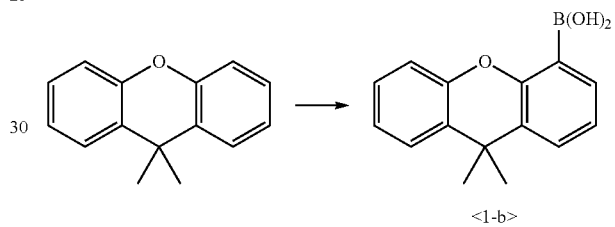

<1-b>

Compound <1-a> (52 g, 247 mmol) was dissolved in tetrahydrofuran (520 mL) in a 1-L flask and 1.6 M butyllithium (155 mL, 247 mmol) was slowly added dropwise at −78° C. The mixture was stirred for 1 hour while maintaining the temperature. After slowly adding trimethyl borate (30.8 g, 297 mmol) dropwise, the mixture was stirred for about 1 hour at room temperature. Upon completion of reaction, 2 N HCl aqueous solution (200 mL) was added dropwise and the mixture was stirred for 30 minutes. After extraction followed by recrystallization with methylene chloride and hexane, compound <1-b> (20 g, yield: 49%) was obtained.

Synthesis Example 1-3

Synthesis of Compound <1-c>

Compound <1-c> was synthesized according to Scheme 3.

[Scheme 3]

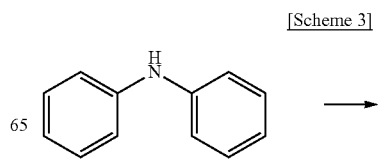

-continued

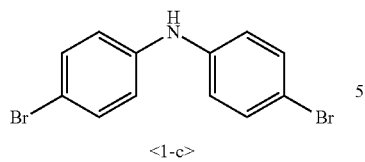
<1-c>

Diphenylamine (40 g, 236 mmol) was dissolved in dimethylformamide (400 mL) in a 1-L flask and stirred at 0° C. After slowly adding N-bromosuccinimide (82 g, 461 mmol), the mixture was stirred at room temperature for 4 hours. Upon completion of reaction, distilled water was added and the resulting brown crystal was filtered and recrystallized with toluene and methanol to obtain compound <1-c> (40 g, yield: 60%).

Synthesis Example 1-4

Synthesis of Compound <1-d>

Compound <1-d> was synthesized according to Scheme 4.

[Scheme 4]

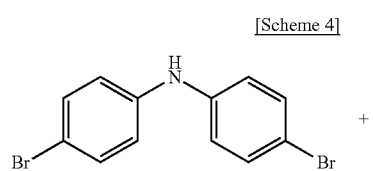

<1-d>

Compound <1-c> (12 g, 37 mmol), compound <1-b> (20.5 g, 81 mmol), potassium carbonate (15.2 g, 11 mmol), tetrakis(triphenylphosphine)palladium (1.7 g, 1 mmol), distilled water (40 mL), toluene (100 mL) and 1,4-dioxane (100 mL) were added to a 500-mL flask and stirred for 24 hours under reflux. Upon completion of reaction, the mixture was concentrated under reduced pressure and recrystallized with toluene and methanol to obtain compound <1-d> (7.9 g, yield: 65%).

Synthesis Example 1-5

Synthesis of Compound of <Chemical Formula 8>

A compound of <Chemical Formula 8> was synthesized according to Scheme 5.

[Scheme 5]

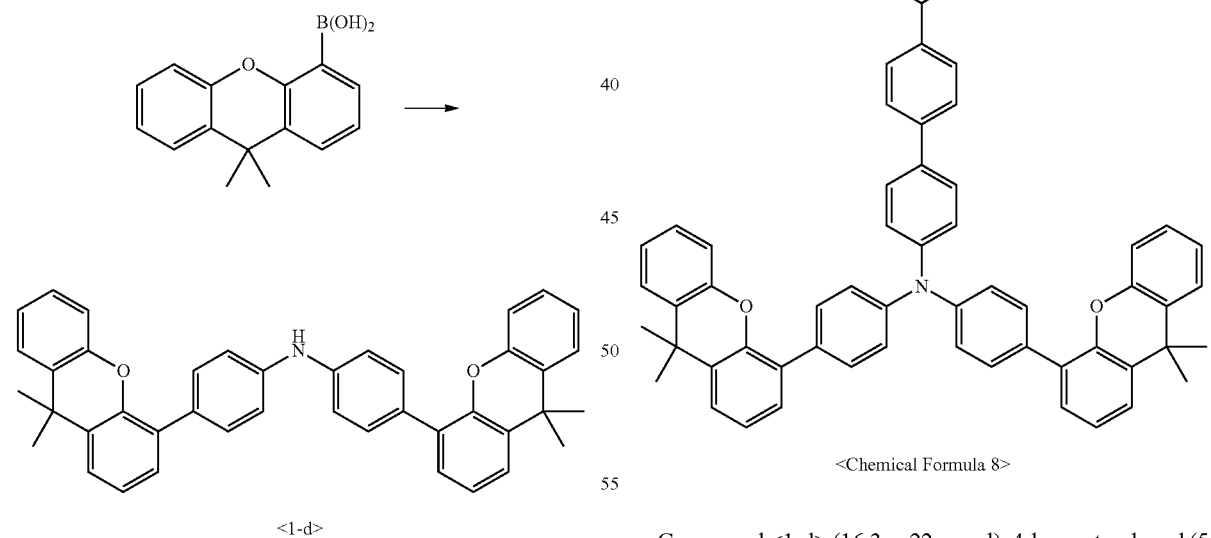

<Chemical Formula 8>

Compound <1-d> (16.3 g, 22 mmol), 4-bromoterphenyl (5 g, 26 mmol), palladium acetate (0.2 g, 0.3 mmol), sodium tert-butoxide (1.9 g, 43 mmol), tri-tert-butylphosphine (0.1 g, 0.3 mmol) and toluene (130 mL) were added to a 300-mL flask and stirred for 3 hours under reflux. Upon completion of reaction, the product was separated by column chromatography and recrystallized with methylene chloride and methanol to obtain a compound of <Chemical Formula 8> (3.0 g, yield: 35 %).

MS [M]$^+$ 813.36.

Synthesis Example 2

Synthesis of Compound of Chemical Formula 17

Synthesis Example 2-1

Synthesis of Compound <2-a>

Compound <2-a> was synthesized according to Scheme 6.

[Scheme 6]

1-Bromo-4-iodobenzene (25 g, 88 mmol), compound <1-b> (26.9 g, 106 mmol), potassium carbonate (24.4 g, 177 mmol), tetrakis(triphenylphosphine)palladium (2 g, 2 mmol), distilled water (50 mL), toluene 130 (mL) and 1,4-dioxane (130 mL) were added to a 2-L flask and stirred for 24 hours under reflux. Upon completion of reaction, the mixture was extracted and separated by column chromatography to obtain compound <2-a> (15 g, yield: 67%).

Synthesis Example 2-2

Synthesis of Compound <2-b>

Compound <2-b> was synthesized according to Scheme 7.

[Scheme 7]

Compound <2-b> (10 g, yield: 73%) was synthesized in the same manner as in Synthesis Example 1-4, except for using biphenylboronic acid instead of compound <1-b>.

Synthesis Example 2-3

Synthesis of Compound of <Chemical Formula 17>

A compound of <Chemical Formula 17> was synthesized according to Scheme 8.

[Scheme 8]

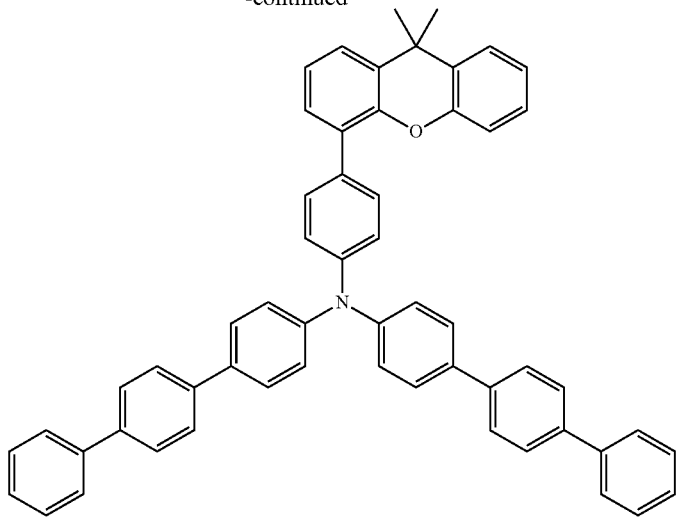

<Chemical Formula 17>

A compound of <Chemical Formula 17> (2.5 g, yield: 27%) was synthesized in the same manner as in Synthesis Example 1-5, except for using compound <2-a> and compound <2-b> instead of compound <1-d> and 4-bromoterphenyl.

MS [M]$^+$ 757.33

Synthesis Example 3

Synthesis of Compound of Chemical Formula 25

Synthesis Example 3-1

Synthesis of Compound <3-a>

Compound <3-a> was synthesized according to Scheme 9.

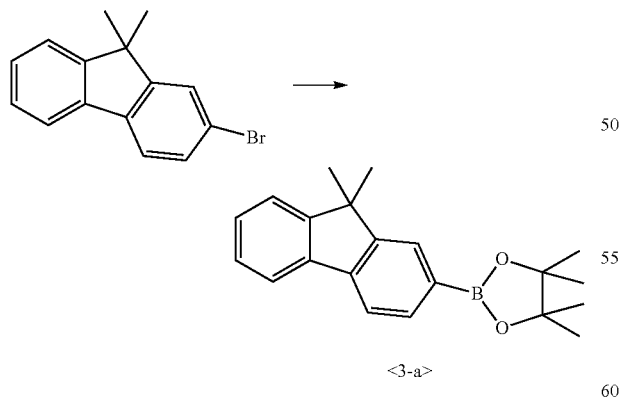

[Scheme 9]

<3-a>

2-Bromo-9,9-dimethylfluorene (40 g, 146 mmol), bis(pinacolato)diboron (55.8 g, 220 mmol), [1,1'-bis(diphenylphosphino)ferrocene]palladium(II) dichloride (3.6 g, 4 mmol), potassium acetate (43.1 g, 439 mmol) and toluene (400 mL) were added to a 1-L flask and stirred for 24 hours under reflux. After concentration under reduced pressure followed by separation by column chromatography, compound <3-a> (27 g, yield: 73%) was obtained.

Synthesis Example 3-2

Synthesis of Compound <3-b>

Compound <3-b> was synthesized according to Scheme 10.

[Scheme 10]

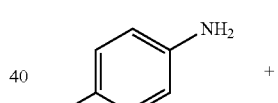

<3-b>

Compound <3-b> (6 g, yield: 39%) was synthesized in the same manner as in Synthesis Example 2-1, except for using 4-bromoaniline and compound <3-a> instead of 1-bromo-4-iodobenzene and compound <1-b>.

Synthesis Example 3-3

Synthesis of Compound <3-c>

Compound <3-c> was synthesized according to Scheme 11.

[Scheme 11]

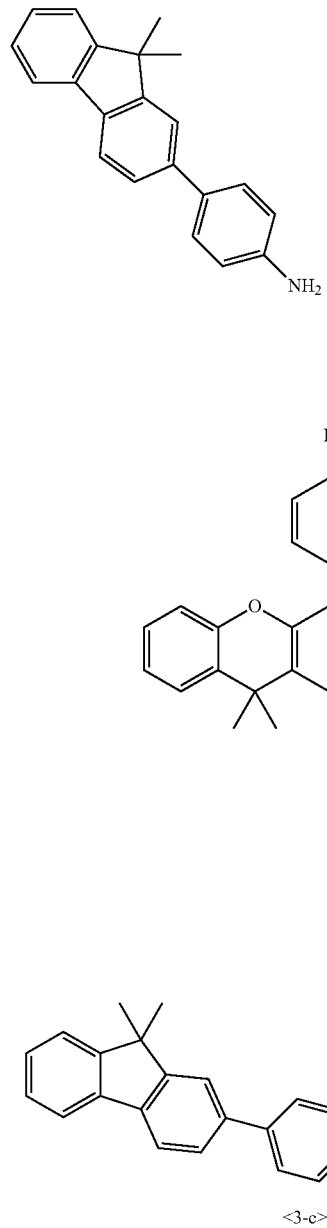

<3-c>

Compound <3-b> (4.5 g, 16 mmol), compound <2-a> (5.8 g, 16 mmol), palladium acetate (0.1 g, 1 mmol), sodium tert-butoxide (3 g, 32 mmol), bis(diphenylphosphino)-1,1'-binaphthyl (0.2 g, 1 mmol) and toluene (45 mL) were added to a 100-mL flask and stirred for 24 hours under reflux. After concentration under reduced pressure followed by separation by column chromatography, compound <3-c> (5.2 g, yield: 92%) was obtained.

Synthesis Example 3-4

Synthesis of Compound <Chemical Formula 25>

A compound of <Chemical Formula 25> was synthesized according to Scheme 12.

[Scheme 12]

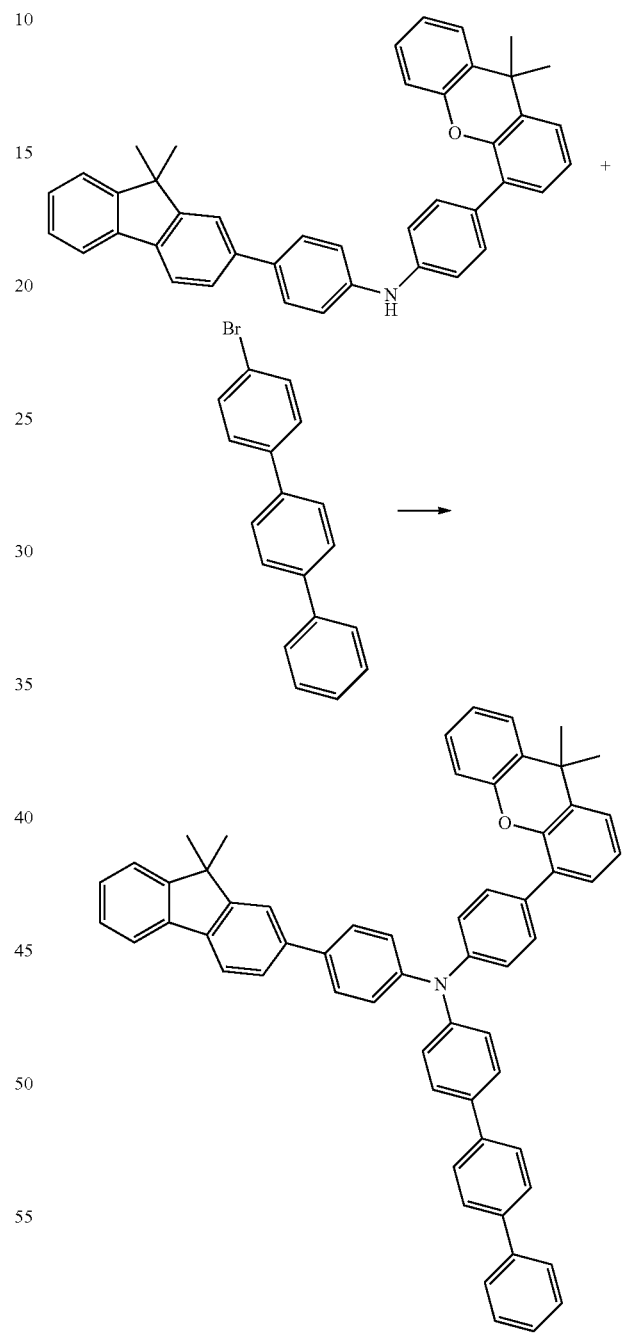

<Chemical Formula 25>

A compound of <Chemical Formula 25> (2.5 g, yield: 27%) was synthesized in the same manner as in Synthesis Example 1-5, except for using compound <3-c> instead of compound <1-d>.

MS [M]$^+$ 797.37.

Synthesis Example 4

Synthesis of Compound of <Chemical Formula 26>

Synthesis Example 4-1

Synthesis of Compound <4-a>

Compound <4-a> was synthesized according to Scheme 13.

[Scheme 13]

Compound <4-a> (45 g, yield: 73%) was synthesized in the same manner as in Synthesis Example 2-1, except for using 1-naphthylboronic acid instead of compound <1-b>.

Synthesis Example 4-2

Synthesis of Compound of <Chemical Formula 26>

A compound of <Chemical Formula 26> was synthesized according to Scheme 14.

[Scheme 14]

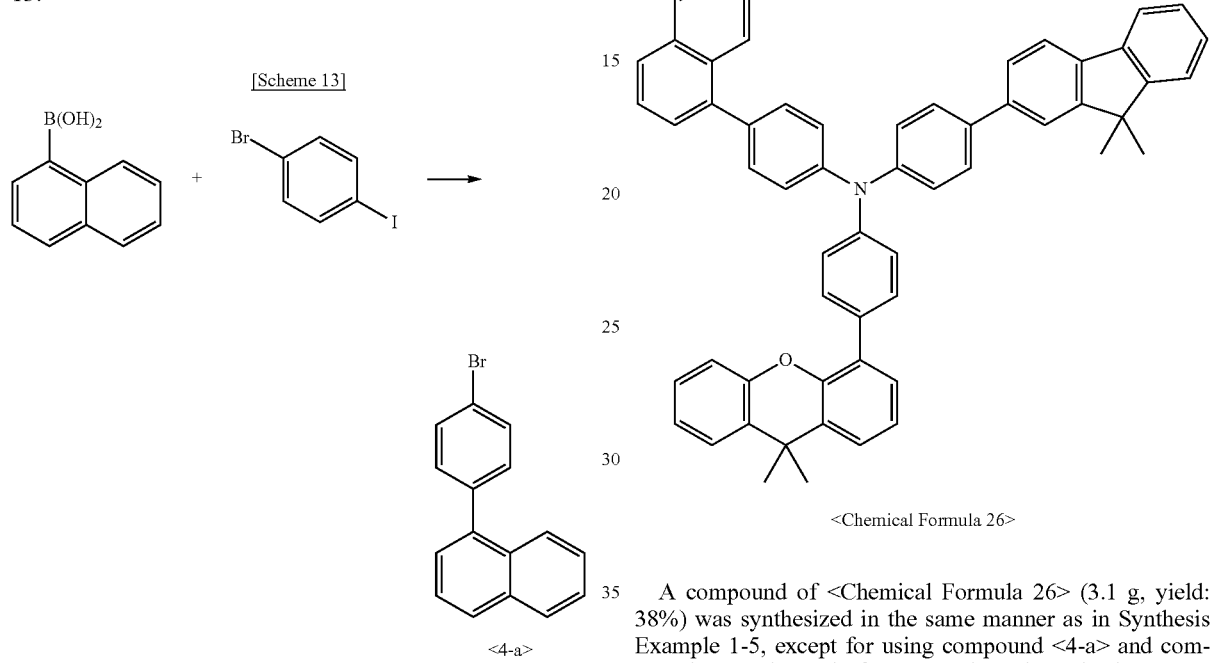

<Chemical Formula 26>

A compound of <Chemical Formula 26> (3.1 g, yield: 38%) was synthesized in the same manner as in Synthesis Example 1-5, except for using compound <4-a> and compound <3-c> instead of compound <1-d> and 4-bromoterphenyl.

MS [M]$^+$ 771.35.

Synthesis Example 5

Synthesis of Compound of <Chemical Formula 55>

Synthesis Example 5-1

Synthesis of Compound <5-a>

Compound <5-a> was synthesized according to Scheme 15.

[Scheme 15]

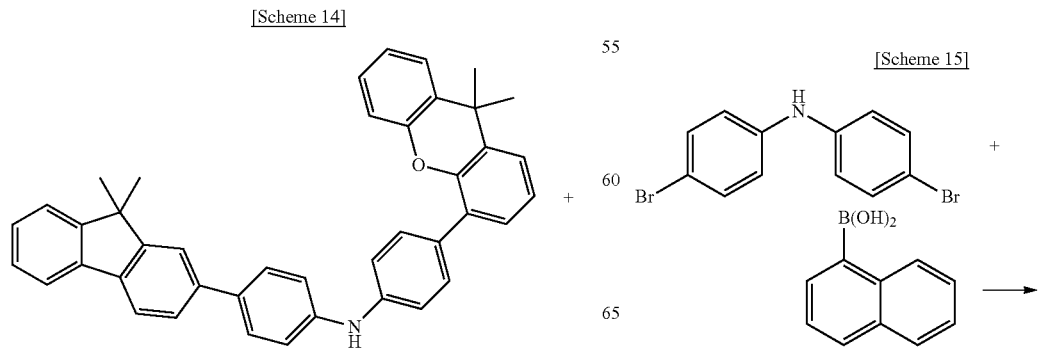

-continued

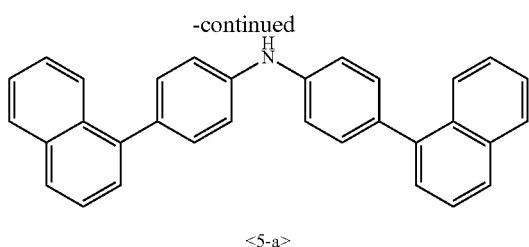

<5-a>

Compound <5-a> (14 g, yield: 62%) was synthesized in the same manner as in Synthesis Example 1-4, except for using 1-naphthylboronic acid instead of biphenylboronic acid.

Synthesis Example 5-2

Synthesis of Compound of <Chemical Formula 55>

A compound of <Chemical Formula 55> was synthesized according to Scheme 16.

[Scheme 16]

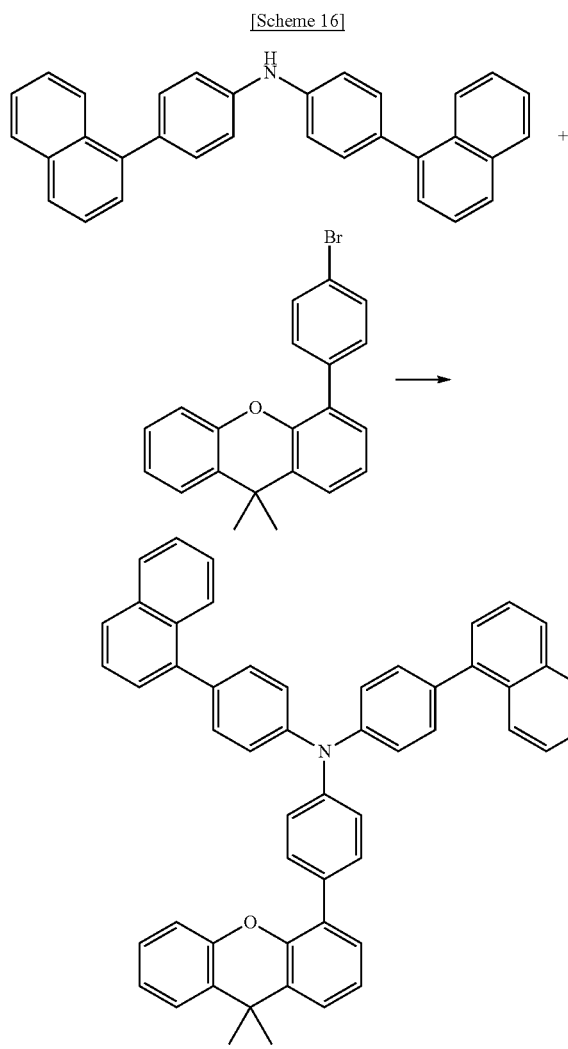

<Chemical Formula 55>

A compound of <Chemical Formula 55> (3.2 g, yield: 38%) was synthesized in the same manner as in Synthesis Example 1-5, except for using compound <5-a> and compound <2-a> instead of compound <1-d> and 4-bromoterphenyl.

MS [M]+ 705.3.

Synthesis Example 6

Synthesis of Compound of <Chemical Formula 67>

Synthesis Example 6-1

Synthesis of Compound <6-a>

Compound <6-a> was synthesized according to Scheme 17.

[Scheme 17]

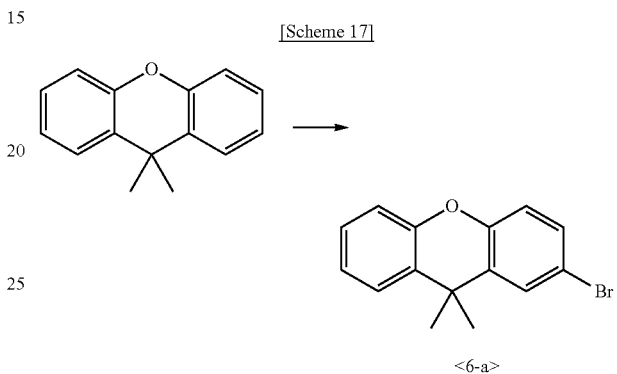

<6-a>

Compound <1-a> (55 g, 252 mmol) was dissolved in acetic acid (550 mL) in a 1-L flask. After adding bromine (15 g, 252 mmol) dissolved in acetic acid (50 mL) dropwise at 0° C., the mixture was stirred at room temperature for about 3 hours. Upon completion of reaction, after adding sodium thiosulfate aqueous solution (100 mL), the formed solid was filtered and separated by column chromatography to obtain compound <6-a> (42 g, yield: 75%).

Synthesis Example 6-2

Synthesis of Compound <6-b>

Compound <6-b> was synthesized according to Scheme 18.

[Scheme 18]

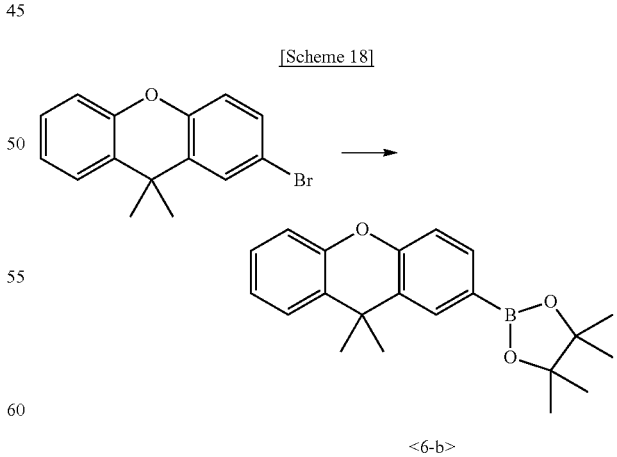

<6-b>

Compound <6-b> (10.5 g, yield: 69%) was synthesized in the same manner as in Synthesis Example 3-1, except for using compound <6-a> instead of 2-bromo-9,9-dimethylfluorene.

Synthesis Example 6-3

Synthesis of Compound <6-c>

Compound <6-c> was synthesized according to Scheme 19.

[Scheme 19]

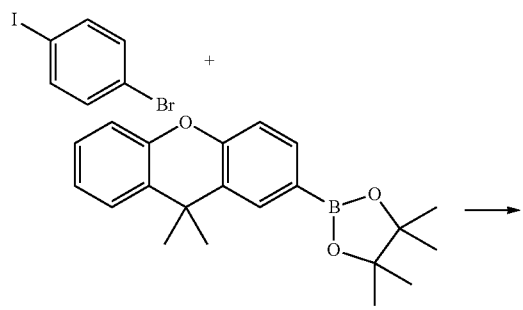

+

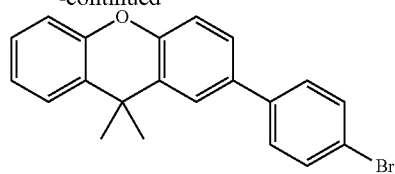

→

<6-c>

Compound <6-c> (21 g, yield: 63%) was synthesized in the same manner as in Synthesis Example 2-1, except for using compound <6-b> instead of compound <1-b>.

Synthesis Example 6-4

Synthesis of Compound of <Chemical Formula 67>

A compound of <Chemical Formula 67> was synthesized according to Scheme 20.

[Scheme 20]

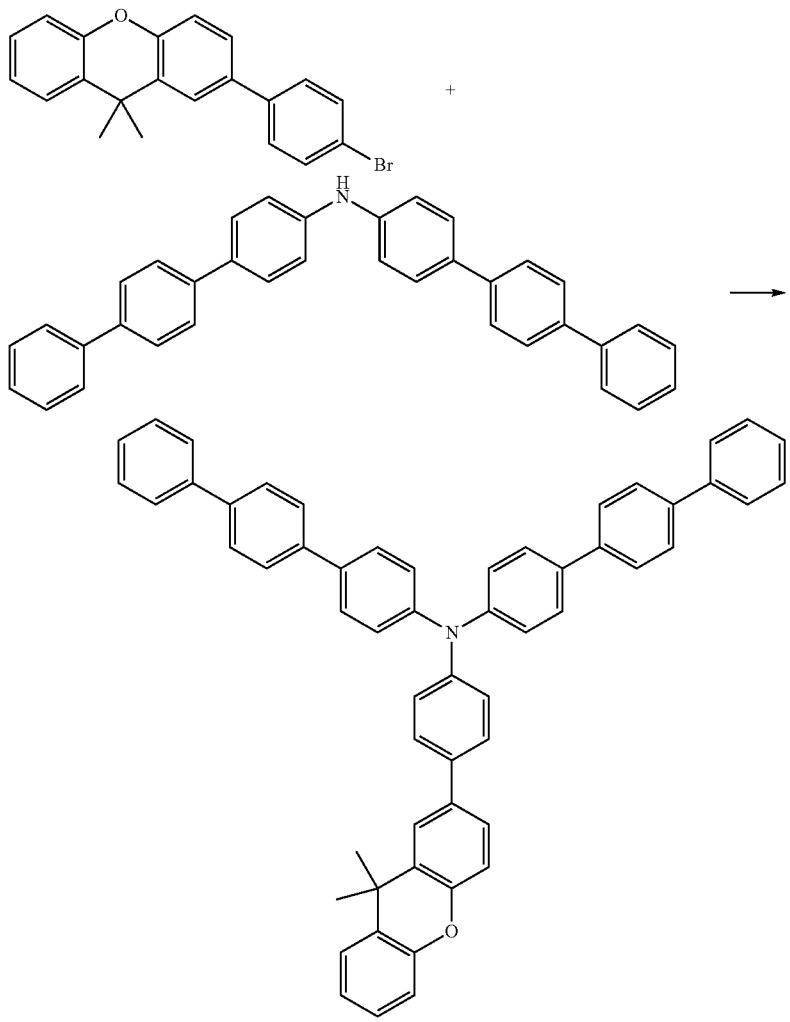

<Chemical Formula 67>

A compound of <Chemical Formula 67> (3.4 g, yield: 31%) was synthesized in the same manner as in Synthesis Example 1-5, except for using compound <6-c> and compound <2-b> instead of compound <1-d> and 4-bromoterphenyl.

MS [M]+ 757.33.

Synthesis Example 7

Synthesis of Compound of <Chemical Formula 74>

Synthesis Example 7-1

Synthesis of Compound <7-a>

Compound <7-a> was synthesized according to Scheme 21.

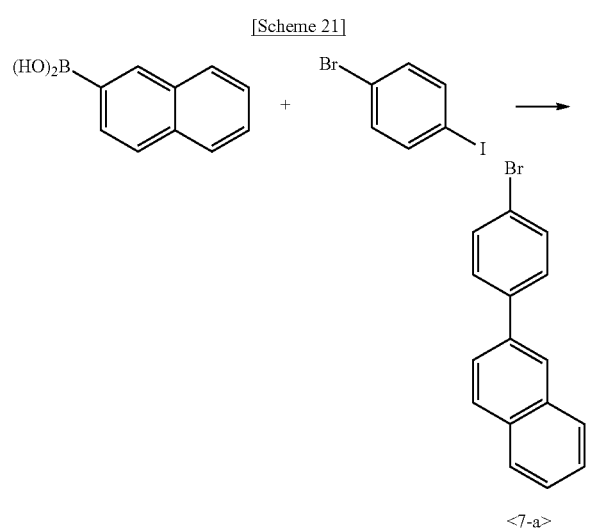

[Scheme 21]

<7-a>

Compound <7-a> (45 g, yield: 73%) was synthesized in the same manner as in Synthesis Example 2-1, except for using 2-naphthylboronic acid instead of compound <1-b>.

Synthesis Example 7-2

Synthesis of Compound of <Chemical Formula 74>

A compound of <Chemical Formula 74> was synthesized according to Scheme 22.

[Scheme 22]

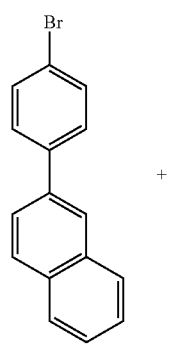

+

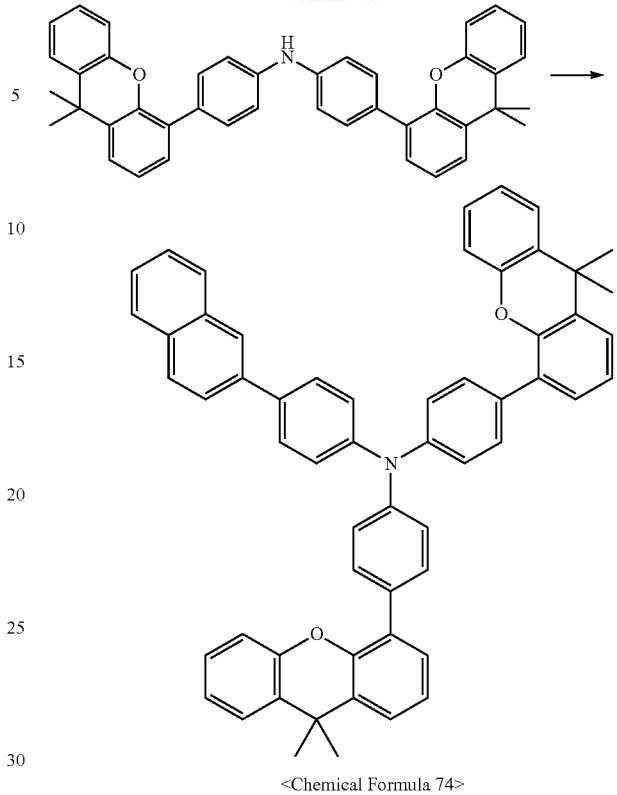

<Chemical Formula 74>

A compound of <Chemical Formula 74> (2.4 g, yield: 32%) was synthesized in the same manner as in Synthesis Example 1-5, except for using compound <7-a> instead of 4-bromoterphenyl.

MS [M]+ 787.35.

Synthesis Example 8

Synthesis of Compound of <Chemical Formula 86>

Synthesis Example 8-1

Synthesis of Compound <8-a>

Compound <8-a> was synthesized according to Scheme 23.

[Scheme 23]

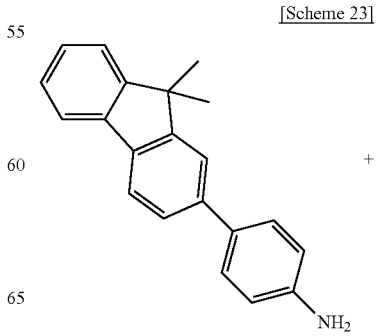

+

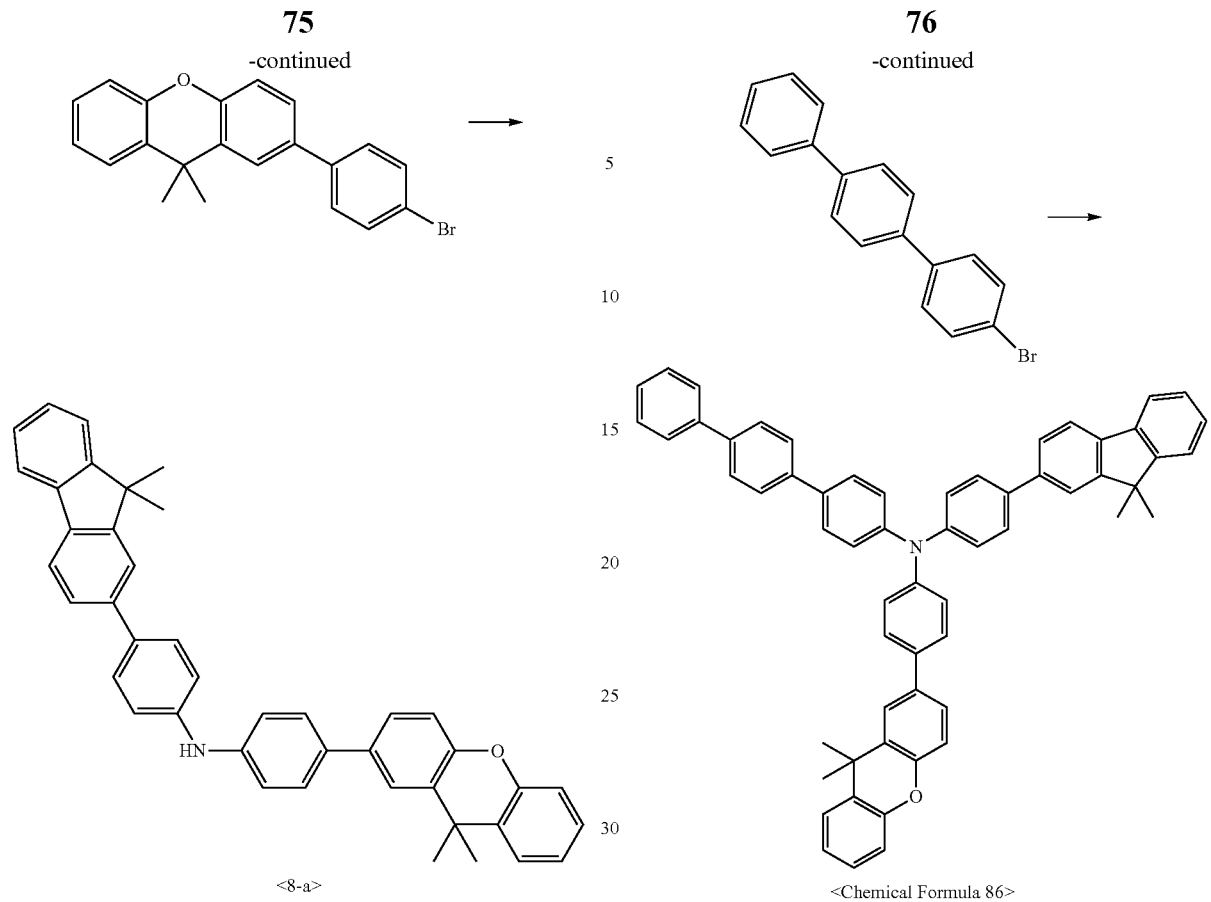

Compound <8-a> (4.8 g, yield: 90%) was synthesized in the same manner as in Synthesis Example 3-3, except for using compound <6-c> instead of compound <2-a>.

Synthesis Example 8-2

Synthesis of Compound of <Chemical Formula 86>

A compound of <Chemical Formula 86> was synthesized according to Scheme 24.

[Scheme 24]

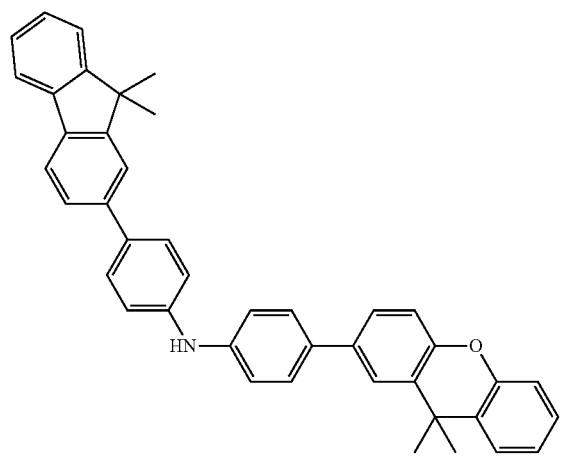

A compound of <Chemical Formula 86> (2.2 g, yield: 25%) was synthesized in the same manner as in Synthesis Example 1-5, except for using compound <8-a> instead of compound <1-d>.

MS [M]$^+$ 797.37.

Synthesis Example 9

Synthesis of Compound of <Chemical Formula 88>

Synthesis Example 9-1

Synthesis of Compound <9-a>

Compound <9-a> was synthesized according to Scheme 25.

[Scheme 25]

-continued

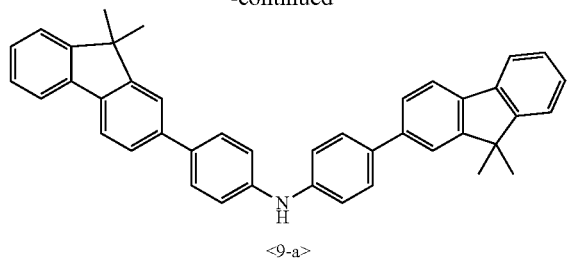
<9-a>

Compound <9-a> (14 g, yield: 62%) was synthesized in the same manner as in Synthesis Example 1-4, except for using compound <3-a> instead of biphenylboronic acid.

Synthesis Example 9-2

Synthesis of Compound of <Chemical Formula 88>

A compound of <Chemical Formula 88> was synthesized according to Scheme 26.

[Scheme 26]

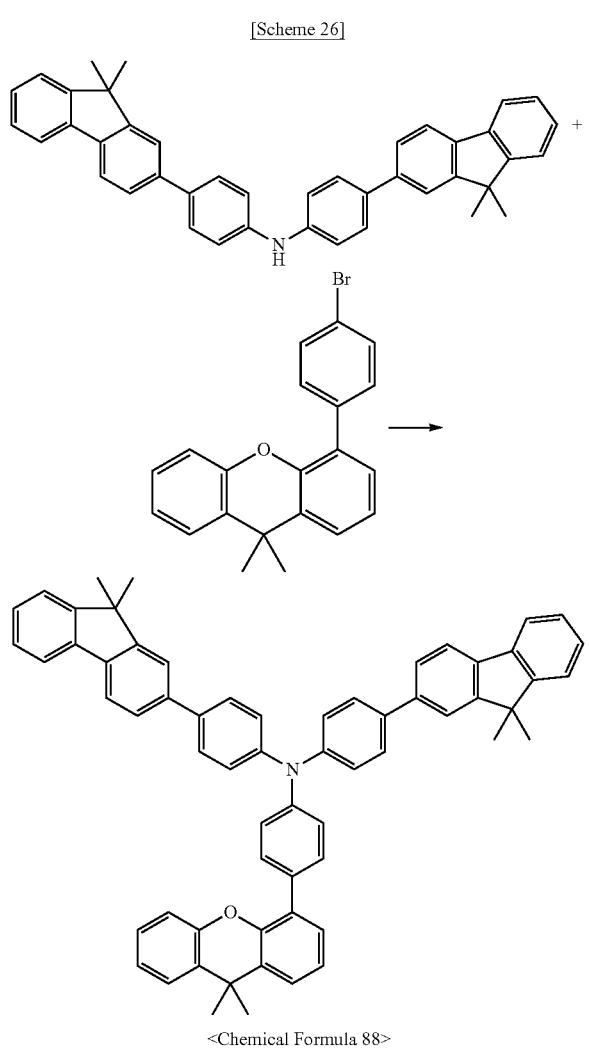

<Chemical Formula 88>

A compound of <Chemical Formula 88> (3.2 g, yield: 38%) was synthesized in the same manner as in Synthesis Example 1-5, except for using compound <9-a> and compound <2-a> instead of compound <1-d> and 4-bromoterphenyl.

MS [M]$^+$ 705.3.

Synthesis Example 10

Synthesis of Compound of <Chemical Formula 90>

Synthesis Example 10-1

Synthesis of Compound <10-a>

Compound <10-a> was synthesized according to Scheme 27.

[Scheme 27]

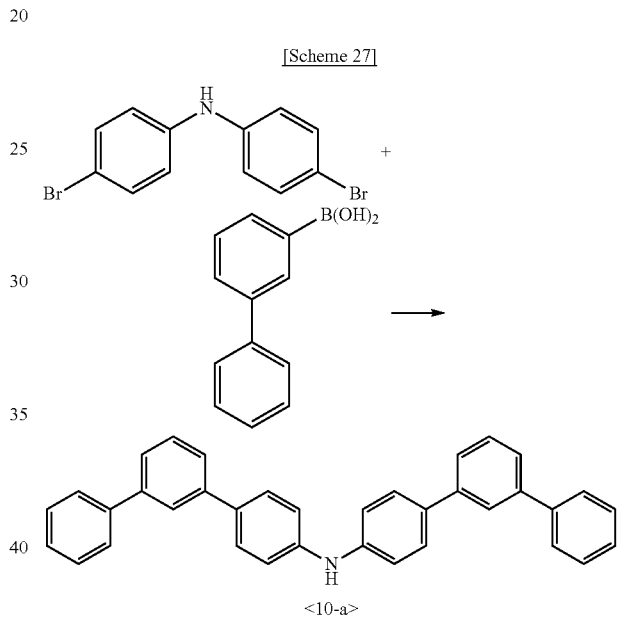
<10-a>

Compound <10-a> (15 g, yield: 64%) was synthesized in the same manner as in Synthesis Example 1-4, except for using 3-biphenylboronic acid instead of biphenylboronic acid.

Synthesis Example 10-2

Synthesis of Compound of <Chemical Formula 90>

A compound of <Chemical Formula 90> was synthesized according to Scheme 28.

[Scheme 28]

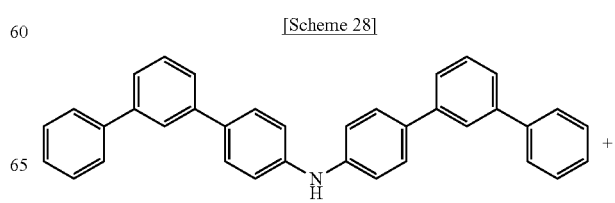

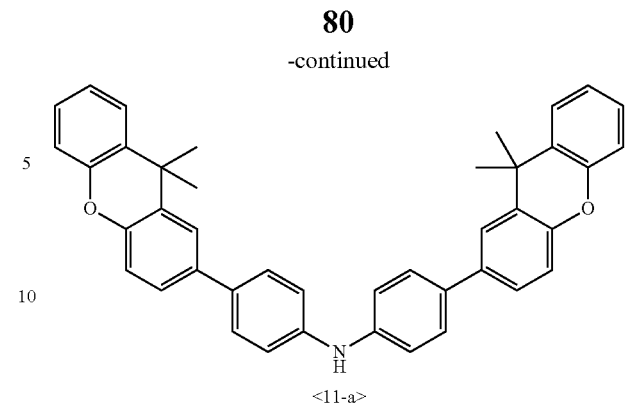

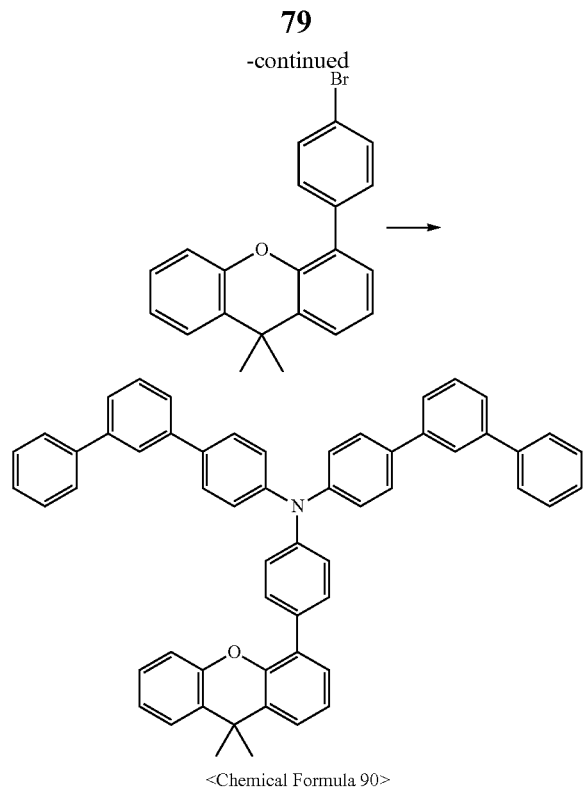

<Chemical Formula 90>

A compound of <Chemical Formula 90> (2.5 g, yield: 28%) was synthesized in the same manner as in Synthesis Example 1-5, except for using compound <10-a> and compound <2-a> instead of compound <1-d> and 4-bromoterphenyl.

MS [M]$^+$ 705.3.

Synthesis Example 11

Synthesis of Compound of <Chemical Formula 93>

Synthesis Example 11-1

Synthesis of Compound <11-a>

Compound <11-a> was synthesized according to Scheme 29.

[Scheme 29]

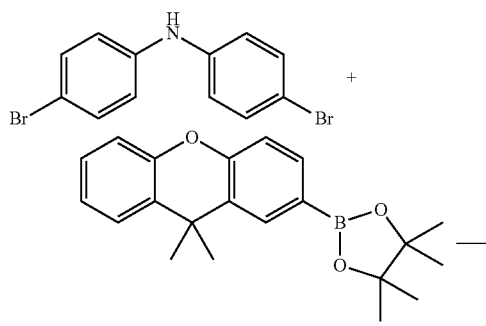

<11-a>

Compound <11-a> (21 g, yield: 52%) was synthesized in the same manner as in Synthesis Example 1-4, except for using compound <6-b> instead of biphenylboronic acid.

Synthesis Example 11-2

Synthesis of Compound of <Chemical Formula 93>

A compound of <Chemical Formula 93> was synthesized according to Scheme 30.

[Scheme 30]

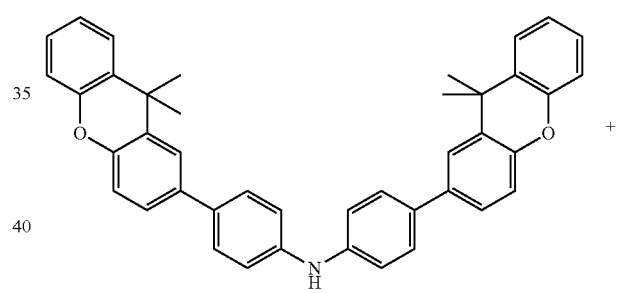

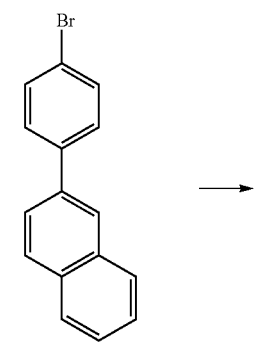

-continued

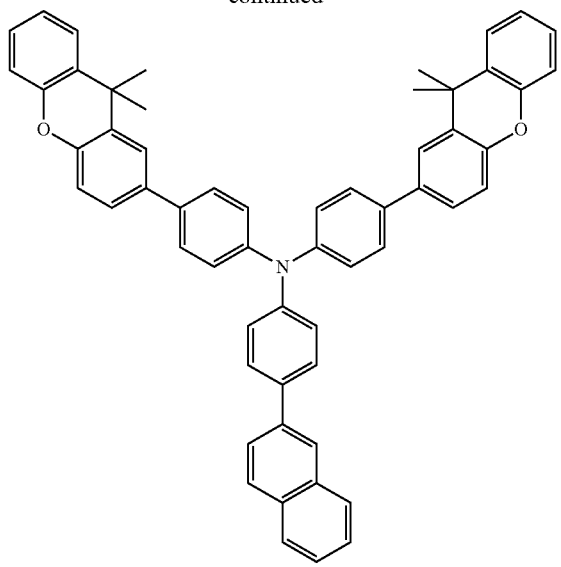

<Chemical Formula 93>

A compound of <Chemical Formula 93> (4.1 g, yield: 48%) was synthesized in the same manner as in Synthesis Example 1-5, except for using compound <11-a> and compound <7-a> instead of compound <1-d> and 4-bromoterphenyl.

MS [M]$^+$ 705.3.

Synthesis Example 12

Synthesis of Compound of <Chemical Formula 96>

Synthesis Example 12-1

Synthesis of Compound <12-a>

Compound <12-a> was synthesized according to Scheme 31.

[Scheme 31]

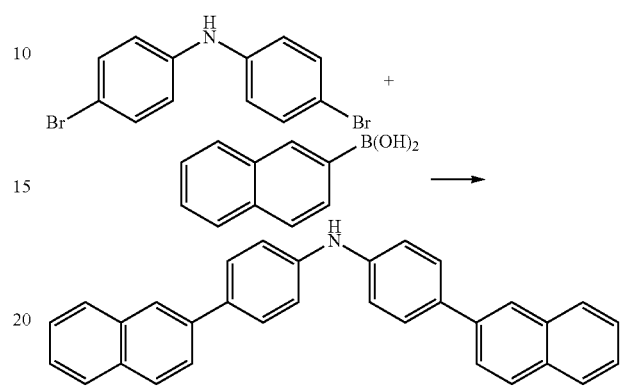

<12-a>

Compound <12-a> (12 g, yield: 61%) was synthesized in the same manner as in Synthesis Example 1-4, except for using 2-naphthylboronic acid instead of biphenylboronic acid.

Synthesis Example 12-2

Synthesis of Compound of <Chemical Formula 96>

A compound of <Chemical Formula 96> was synthesized according to Scheme 32.

[Scheme 32]

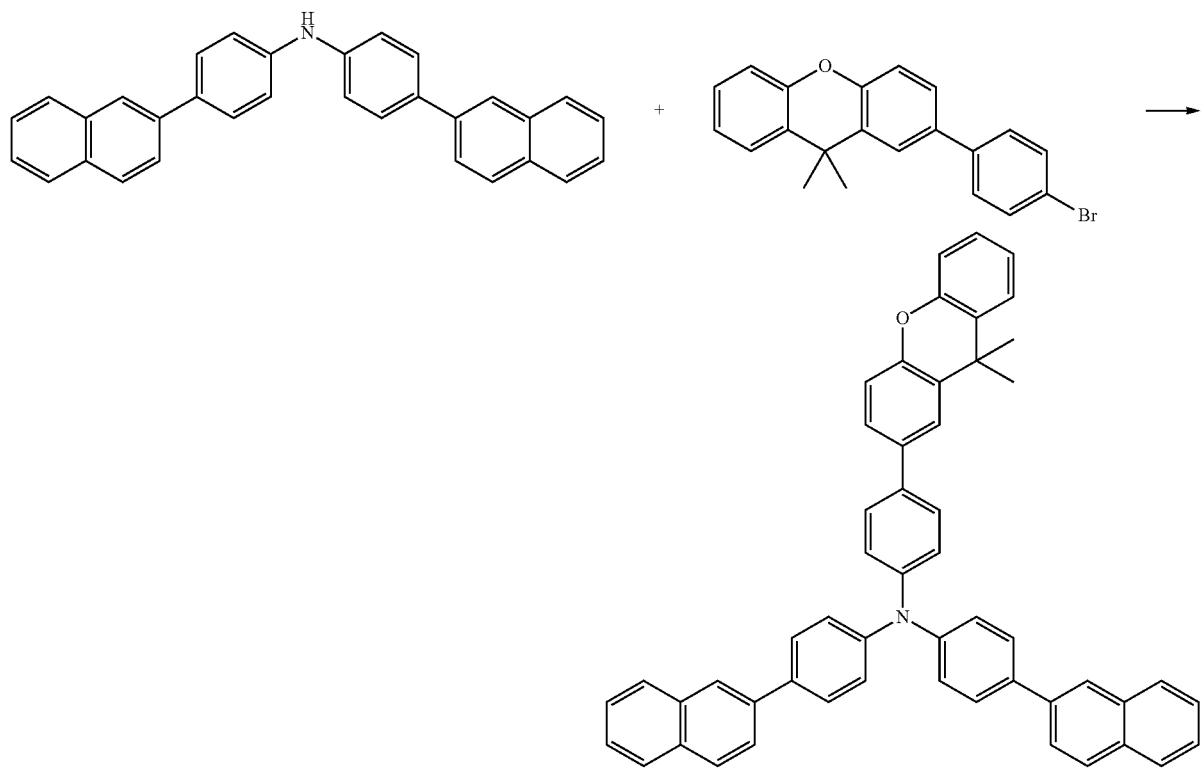

<Chemical Formula 96>

A compound of <Chemical Formula 96> (1.5 g, yield: 27%) was synthesized in the same manner as in Synthesis Example 1-5, except for using compound <12-a> and compound <6-c> instead of compound <1-d> and 4-bromoterphenyl.

MS [M]⁺ 705.3.

Synthesis Example 13

Synthesis of Compound of <Chemical Formula 97>

Synthesis Example 13-1

Synthesis of Compound <13-a>

Compound <13-a> was synthesized according to Scheme 33.

[Scheme 33]

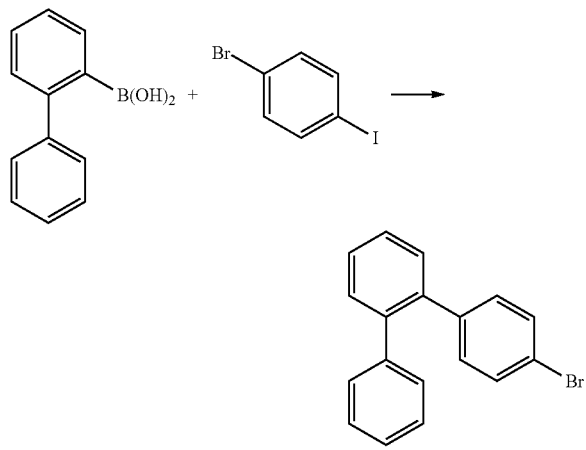

<13-a>

Compound <13-a> (45 g, yield: 73%) was synthesized in the same manner as in Synthesis Example 2-1, except for using 2-biphenylboronic acid instead of compound <1-b>.

Synthesis Example 13-2

Synthesis of Compound of <Chemical Formula 97>

A compound of <Chemical Formula 97> was synthesized according to Scheme 34.

[Scheme 34]

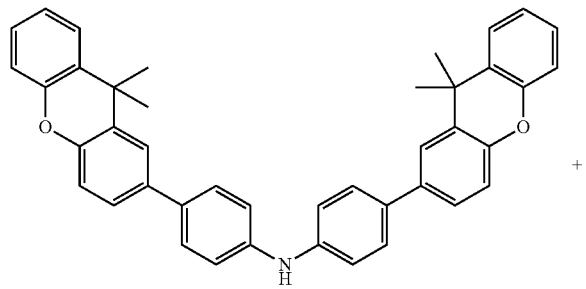

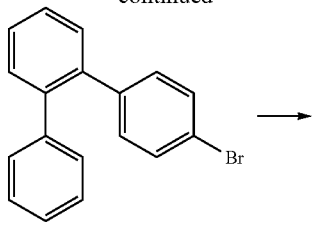

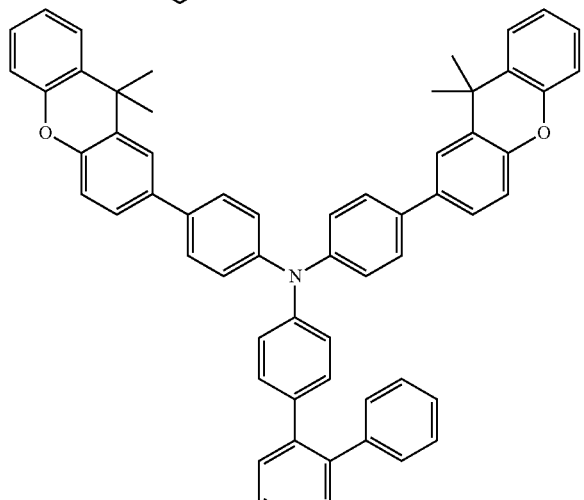

<Chemical Formula 97>

A compound of <Chemical Formula 97> (3.7 g, yield: 32%) was synthesized in the same manner as in Synthesis Example 1-5, except for using compound <11-a> and compound <13-a> instead of compound <1-d> and 4-bromoterphenyl.

MS [M]⁺ 813.36.

Synthesis Example 14

Synthesis of Compound of <Chemical Formula 98>

Synthesis Example 14-1

Synthesis of Compound <14-a>

Compound <14-a> was synthesized according to Scheme 35.

[Scheme 35]

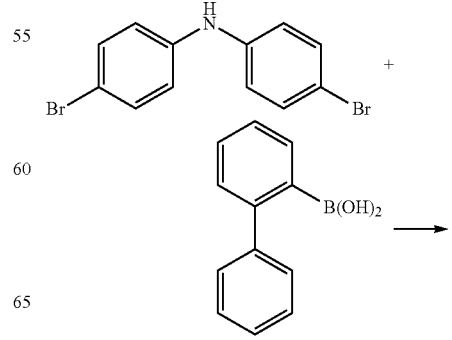

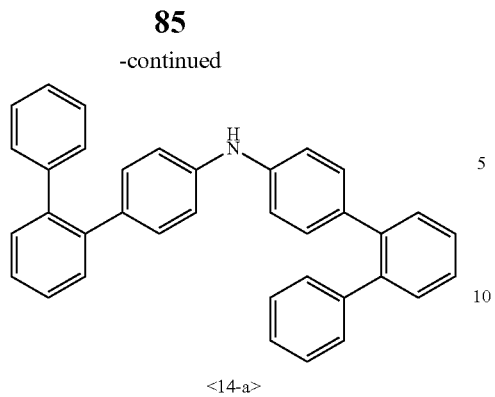

<14-a>

Compound <14-a> (9 g, yield: 52%) was synthesized in the same manner as in Synthesis Example 1-4, except for using 2-biphenylboronic acid instead of biphenylboronic acid.

Synthesis Example 14-2

Synthesis of Compound of <Chemical Formula 98>

A compound of <Chemical Formula 98> was synthesized according to Scheme 36.

[Scheme 36]

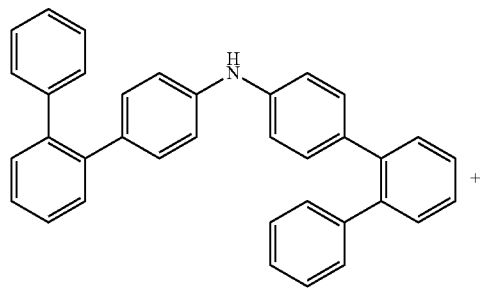

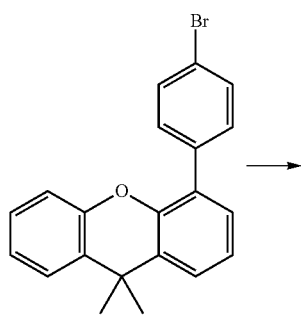

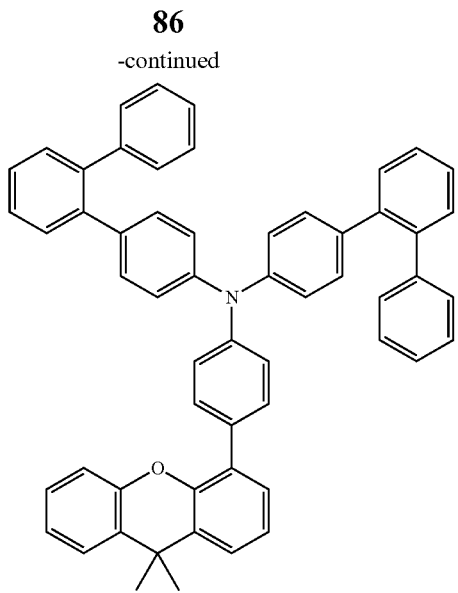

<Chemical Formula 98>

A compound of <Chemical Formula 98> (4 g, yield: 28%) was synthesized in the same manner as in Synthesis Example 1-5, except for using compound <14-a> and compound <2-a> instead of compound <1-d> and 4-bromoterphenyl.

MS [M]$^+$ 757.33.

Synthesis Example 15

Synthesis of Compound of <Chemical Formula 99>

Synthesis Example 15-1

Synthesis of Compound of <Chemical Formula 99>

A compound of <Chemical Formula 99> was synthesized according to Scheme 37.

[Scheme 37]

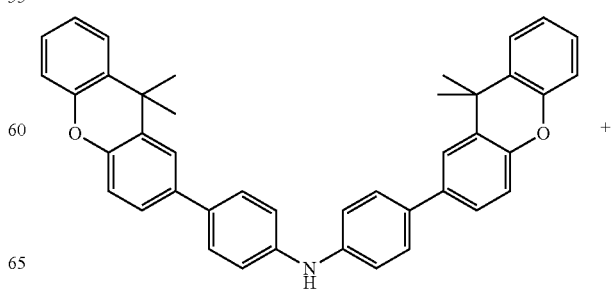

-continued

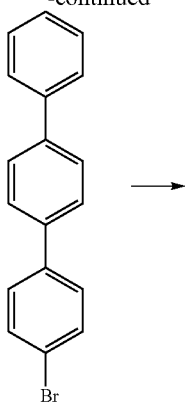

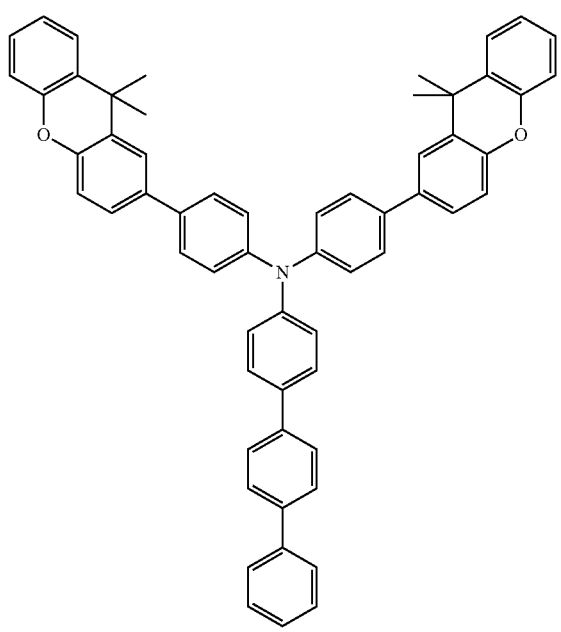

<Chemical Formula 99>

A compound of <Chemical Formula 99> (2.5 g, yield: 33%) was synthesized in the same manner as in Synthesis Example 1-5, except for using compound <11-a> instead of compound <1-d>.

MS [M]⁺ 813.36.

Synthesis Example 16

Synthesis of Compound of <Chemical Formula 100>

Synthesis Example 16-1

Synthesis of Compound <16-a>

Compound <16-a> was synthesized according to Scheme 38.

[Scheme 38]

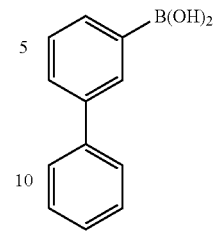 + 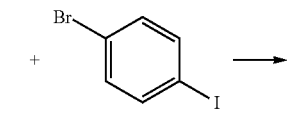 →

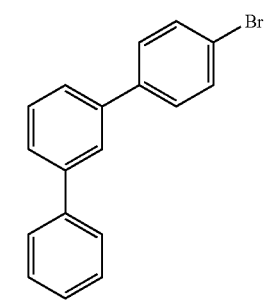

<16-a>

Compound <16-a> (15 g, yield: 63%) was synthesized in the same manner as in Synthesis Example 2-1, except for using 3-biphenylboronic acid instead of compound <1-b>.

Synthesis Example 16-2

Synthesis of Compound of <Chemical Formula 100>

A compound of <Chemical Formula 100> was synthesized according to Scheme 39.

[Scheme 39]

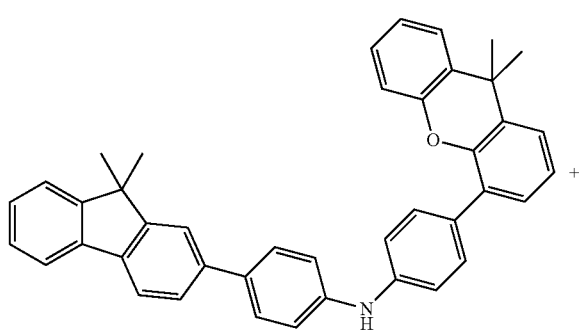

+

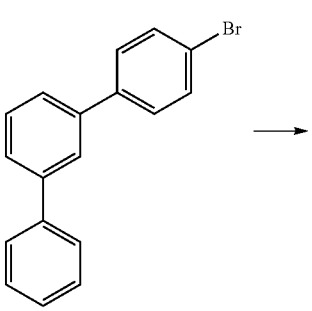

→

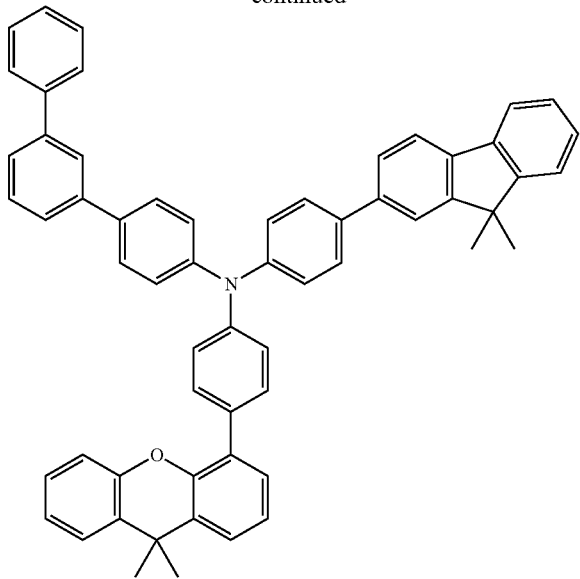

<Chemical Formula 100>

A compound of <Chemical Formula 100> (3.3 g, yield: 33%) was synthesized in the same manner as in Synthesis Example 1-5, except for using compound <3-c> and compound <16-a> instead of compound <1-d> and 4-bromoterphenyl.

MS [M]$^+$ 797.37.

Synthesis Example 17

Synthesis of Compound of <Chemical Formula 105>

Synthesis Example 17-1

Synthesis of Compound <17-a>

Compound <17-a> was synthesized according to Scheme 40.

[Scheme 40]

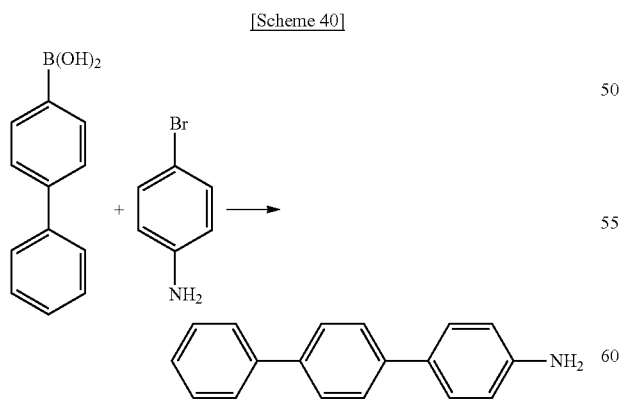

Compound <17-a> (6.1 g, yield: 78%) was synthesized in the same manner as in Synthesis Example 2-1, except for using 4-bromoaniline and 4-biphenylboronic acid instead of 1-bromo-4-iodobenzene and compound <1-b>.

Synthesis Example 17-2

Synthesis of Compound of <Chemical Formula 105>

A compound of <Chemical Formula 105> was synthesized according to Scheme 41.

[Scheme 41]

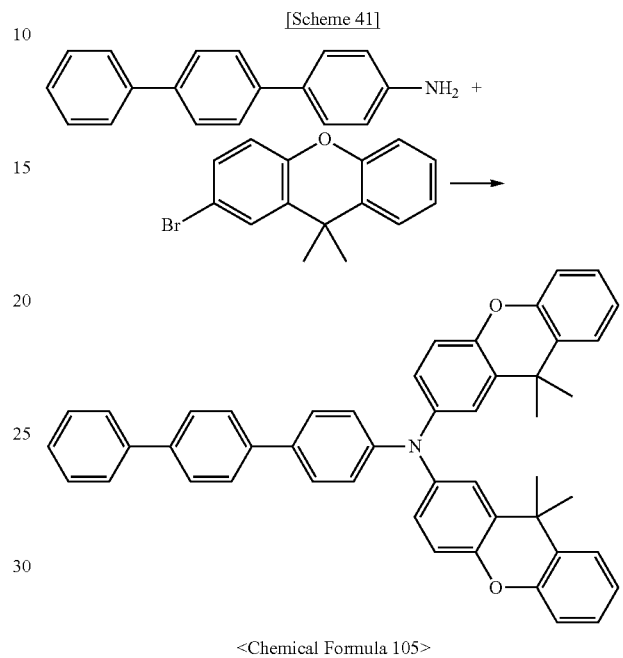

<Chemical Formula 105>

Compound <17-a> (4.5 g, 18 mmol), compound <6-a> (12.7 g, 44 mmol), tris(benzylideneacetone)palladium (0.7 g, 1 mmol), sodium tert-butoxide (5.3 g, 55 mmol), bis(diphenylphosphino)-1,1'-binaphthyl (0.5 g, 1 mmol) and toluene (45 mL) were added to a 100-mL flask and stirred for 24 hours under reflux. Upon completion of reaction, the mixture was filtered and separated by column chromatography to obtain a compound of <Chemical Formula 105> (3.4 g, yield: 32%).

MS [M]$^+$ 661.30.

Example 1

ITO glass was patterned to have an emitting area of 2 mm×2 mm and then cleaned. The ITO glass was mounted in a vacuum chamber and a base pressure was set to 1×10$^{-7}$ torr. Then, CuPc (800 Å) and the compound of [Chemical Formula 8] (300 Å) were sequentially deposited on the ITO. Subsequently, a mixture of host BH1 and dopant BD1 (3%) was deposited (250 Å) and then 3,3-(3,8-di(biphenyl-4-yl)pyrene-1,6-diyl)dipyridine (350 Å), LiF (5 Å) and Al (500 Å) were sequentially deposited to prepare an organic electroluminescent device. The emission characteristics of the organic electroluminescent device were measured at 0.4 mA.

Examples 2-17

Organic electroluminescent devices were prepared in the same manner as in Example 1 using the compounds described in [Table 1] instead of the compound of [Chemical Formula 8] and the emission characteristics of the organic electroluminescent device were measured at 0.4 mA.

<BH1>

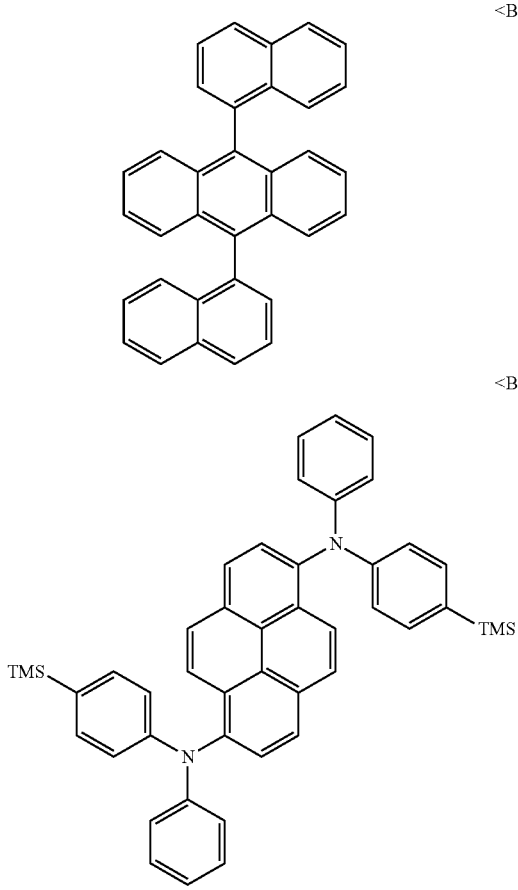

<BD1>

Comparative Example

For comparison, an organic light-emitting diode device was prepared in the same manner as in Example 1 using NPD which is commonly used as a hole transport material. The structure of NPD is as follows.

<NPD>

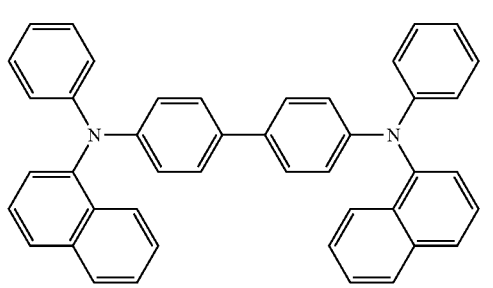

TABLE 1

| | Hole transport material | V | cd/m² | $CIE_x$ | $CIE_y$ | $T_{80}$ (hrs) at 3000 cd/m² |
|---|---|---|---|---|---|---|
| Comparative Example 1 | NPD | 4.4 | 620 | 0.134 | 0.127 | 75 |
| Example 1 | Chemical Formula 8 | 4.1 | 884 | 0.135 | 0.128 | 171 |

TABLE 1-continued

| | Hole transport material | V | cd/m² | $CIE_x$ | $CIE_y$ | $T_{80}$ (hrs) at 3000 cd/m² |
|---|---|---|---|---|---|---|
| Example 2 | Chemical Formula 17 | 4.2 | 857 | 0.135 | 0.125 | 195 |
| Example 3 | Chemical Formula 25 | 4.3 | 898 | 0.134 | 0.120 | 162 |
| Example 4 | Chemical Formula 26 | 4.2 | 842 | 0.136 | 0.125 | 142 |
| Example 5 | Chemical Formula 55 | 4.1 | 902 | 0.138 | 0.126 | 165 |
| Example 6 | Chemical Formula 67 | 4.5 | 752 | 0.131 | 0.125 | 175 |
| Example 7 | Chemical Formula 74 | 4.2 | 887 | 0.138 | 0.122 | 150 |
| Example 8 | Chemical Formula 86 | 4.2 | 869 | 0.128 | 0.125 | 155 |
| Example 9 | Chemical Formula 88 | 4.1 | 828 | 0.129 | 0.129 | 140 |
| Example 10 | Chemical Formula 90 | 4.3 | 787 | 0.135 | 0.123 | 141 |
| Example 11 | Chemical Formula 93 | 4.4 | 855 | 0.139 | 0.127 | 123 |
| Example 12 | Chemical Formula 96 | 4.1 | 833 | 0.136 | 0.122 | 135 |
| Example 13 | Chemical Formula 97 | 4.2 | 897 | 0.137 | 0.125 | 145 |
| Example 14 | Chemical Formula 98 | 4.5 | 862 | 0.139 | 0.124 | 152 |
| Example 15 | Chemical Formula 99 | 4.3 | 784 | 0.138 | 0.128 | 163 |
| Example 16 | Chemical Formula 100 | 4.1 | 765 | 0.143 | 0.123 | 123 |
| Example 17 | Chemical Formula 105 | 4.2 | 842 | 0.142 | 0.125 | 136 |

$T_{80}$ indicates the time at which the luminance is decreased to 80% of the initial luminance. As seen from [Table 1], the organic light-emitting diodes including the organic compounds according to the present disclosure in the hole transport layer exhibited long lifetime and superior luminous efficiency as compared to the organic light-emitting diode including NPD owing to improved hole transport ability.

While the present disclosure has been described with respect to the specific embodiments, it will be apparent to those skilled in the art that various changes and modifications may be made without departing from the spirit and scope of the disclosure as defined in the following claims.

What is claimed is:

1. An organic electroluminescent compound represented by [Chemical Formula 1]:

[Chemical Formula 1]

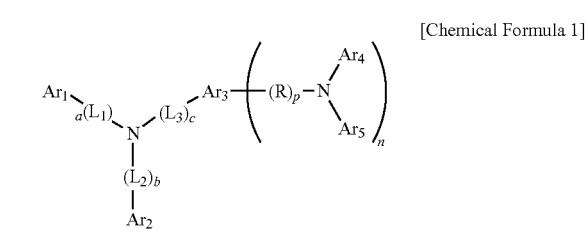

wherein
each of $L_1$ through $L_3$, which are identical or different, is independently selected from a substituted or unsubstituted $C_{6-30}$ aryl group and a substituted or unsubstituted $C_{5-30}$ heteroaryl group,
each of a, b and c is independently an integer from 0 to 3, wherein if a, b and c are 2 or greater, the plurality of $L_1$'s through $L_3$'s are identical or different, each of $Ar_1$ through $Ar_5$, which are identical or different, is independently selected from a group represented by [Chemical Formula L], a substituted or unsubstituted $C_{1-30}$ alkyl group, a substituted or unsubstituted $C_{6-60}$ aryl group and a substituted or unsubstituted $C_{5-60}$ heteroaryl group, wherein at least one of $Ar_1$ through $Ar_3$ is a group represented by [Chemical Formula L], R is selected from a substituted or unsubstituted $C_{6-60}$ aryl group and a substituted or unsubstituted $C_{5-60}$ heteroaryl group, p is an integer from 0 to 3, wherein if p is 2 or greater, the plurality of R's are identical or different,

[Chemical Formula L]

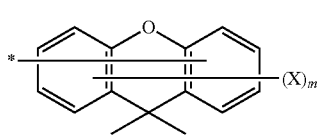

wherein

X is selected from hydrogen, deuterium, a halogen atom, a cyano group, a nitro group, a substituted or unsubstituted $C_{1-30}$ alkyl group, a substituted or unsubstituted $C_{5-60}$ heteroaryl group, a substituted or unsubstituted $C_{3-30}$ cycloalkyl group, a substituted or unsubstituted $C_{6-60}$ aryl group, a substituted or unsubstituted $C_{1-30}$ alkoxy group, a substituted or unsubstituted $C_{6-60}$ aryloxy group, a substituted or unsubstituted $C_{1-30}$ alkylamino group, a substituted or unsubstituted $C_{6-60}$ arylamino group, a substituted or unsubstituted $C_{1-30}$ alkylsilyl group, a substituted or unsubstituted $C_{6-60}$ arylsilyl group and a substituted or unsubstituted $C_{2-30}$ alkenyl group, m is an integer from 0 to 7, wherein if m is 2 or greater, the plurality of X's are identical or different, and n is an integer from 0 to 3, wherein if n is 2 or greater, the plurality of

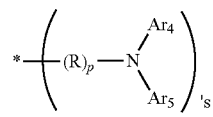

are identical or different.

2. The organic electroluminescent compound according to claim 1, wherein, if $L_1$ through $L_3$, $Ar_1$ through $Ar_5$, R and X are further substituted with substituents, the substituent is one or more selected from deuterium, a cyano group, a halogen atom, a nitro group, a $C_{1-20}$ alkyl group, a $C_{6-30}$ aryl group, a $C_{5-30}$ heteroaryl group, a $C_{1-20}$ alkylamino group, a $C_{6-30}$ arylamino group, a $C_{1-20}$ alkoxy group, a $C_{6-30}$ aryloxy group, a $C_{3-20}$ cycloalkyl group, a $C_{6-30}$ arylthio group, a $C_{1-20}$ alkenyl group, a $C_{1-20}$ alkylsilyl group and a $C_{6-30}$ arylsilyl group, and the substituent may be connected with an adjacent substituent to form a saturated or unsaturated ring.

3. The organic electroluminescent compound according to claim 1, wherein the compound represented by [Chemical Formula 1] is a compound selected from compounds represented by [Chemical Formula 1-1] through [Chemical Formula 1-3]:

[Chemical Formula 1-1]

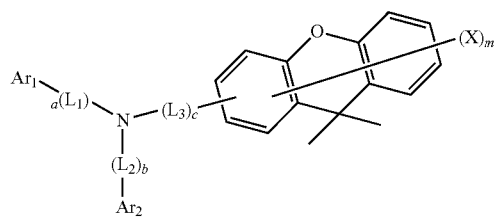

[Chemical Formula 1-2]

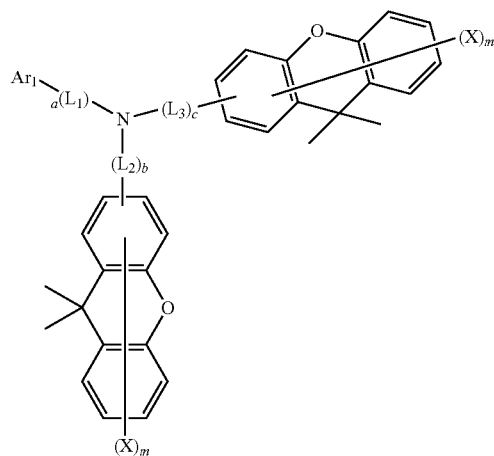

[Chemical Formula 1-3]

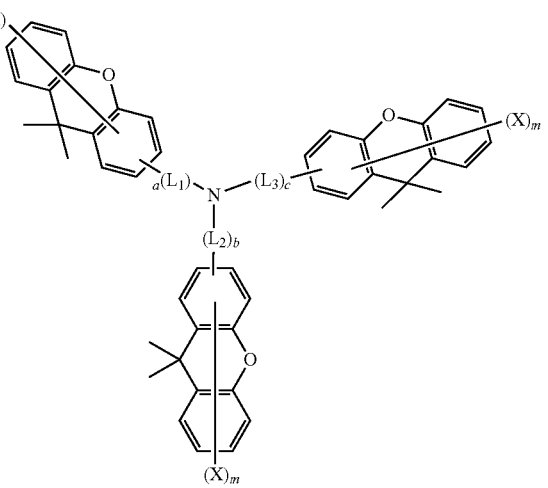

wherein each of $Ar_1$, $Ar_2$, $L_1$ through $L_3$, X, a through c and m is the same as defined in [Chemical Formula 1].

4. The organic electroluminescent compound according to claim 1, wherein the compound represented by [Chemical Formula 1] is selected from a group consisting of compounds represented by [Chemical Formula 2] through [Chemical Formula 120]:

[Chemical Formula 2]
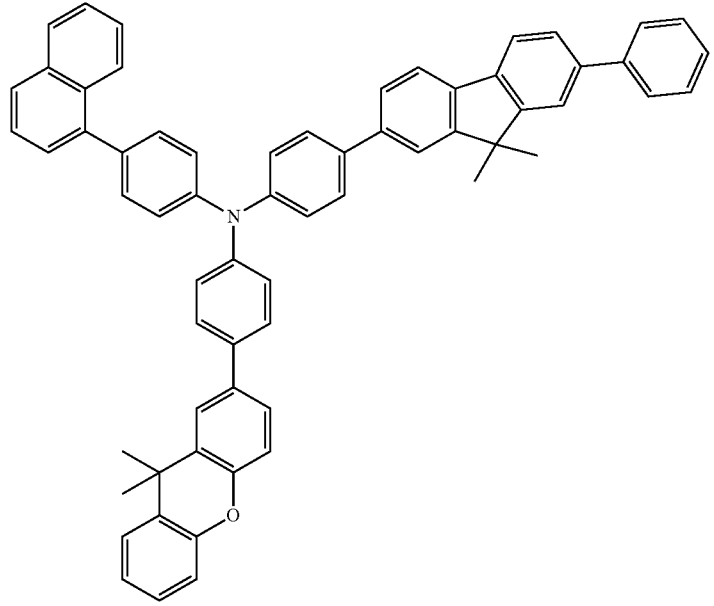
[Chemical Formula 3]
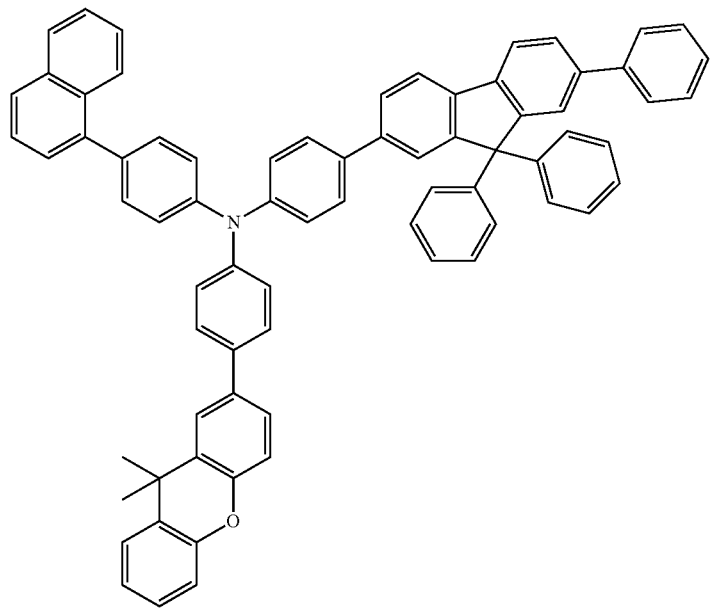

[Chemical Formula 4]
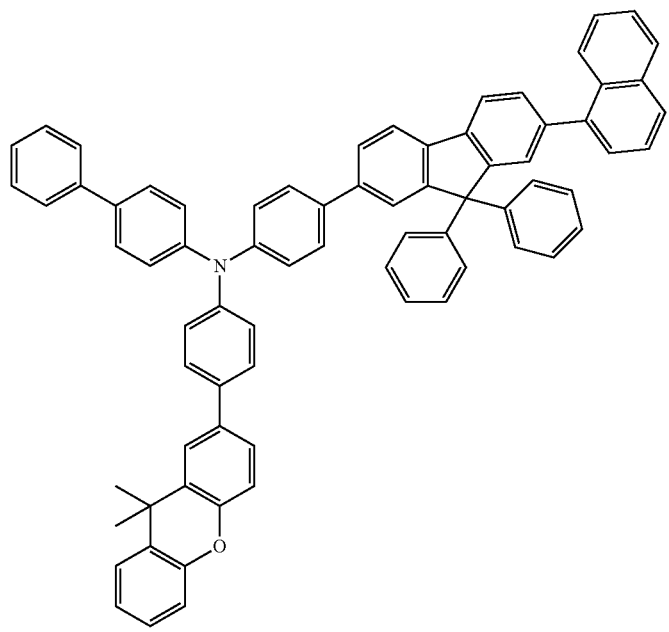
[Chemical Formula 5]
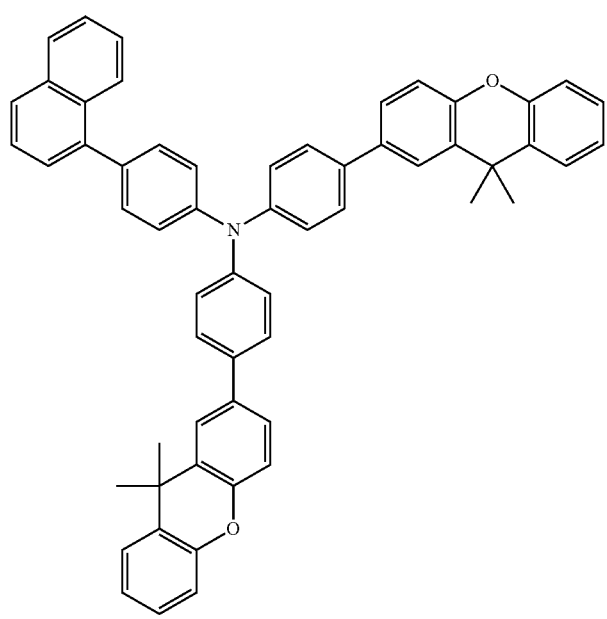

-continued
[Chemical Formula 6]
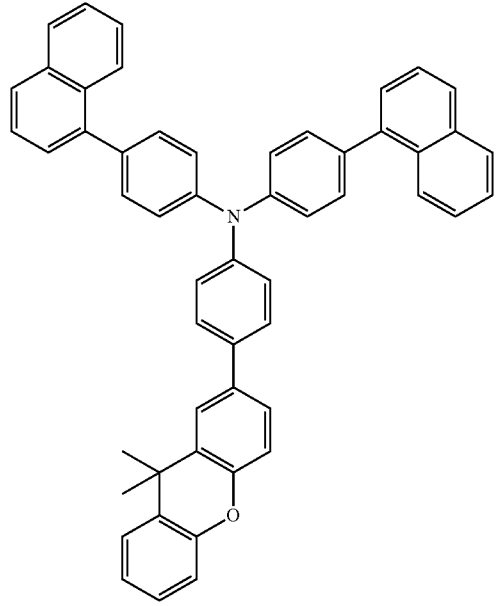
[Chemical Formula 7]
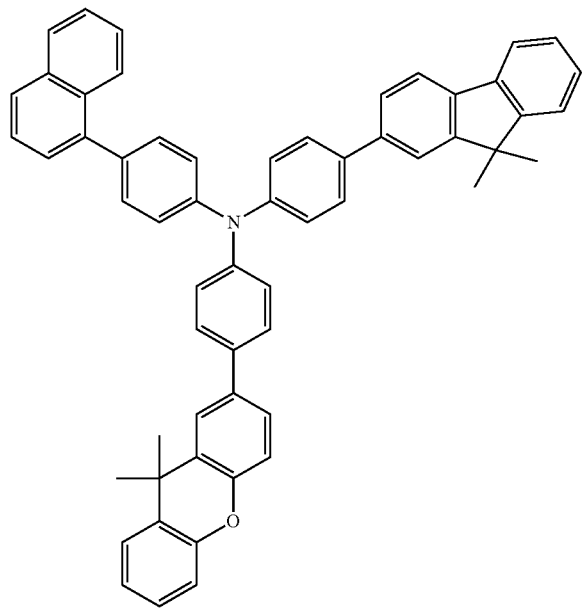

[Chemical Formula 8]
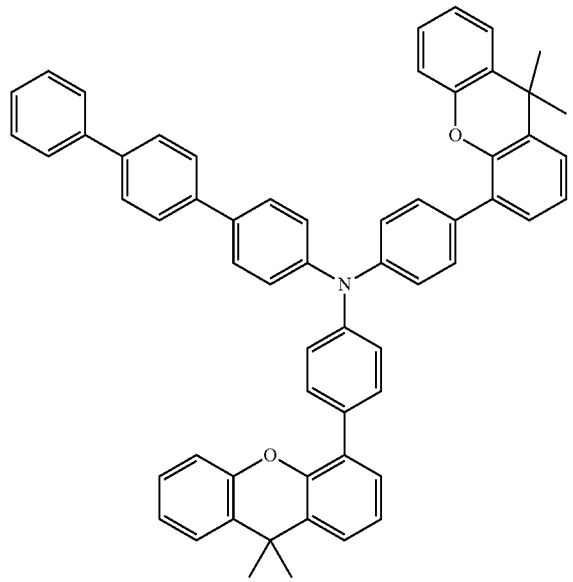
[Chemical Formula 9]
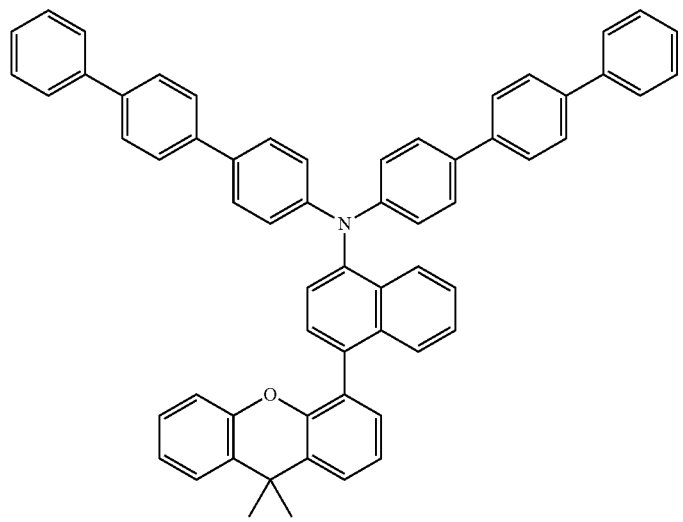
[Chemical Formula 10]
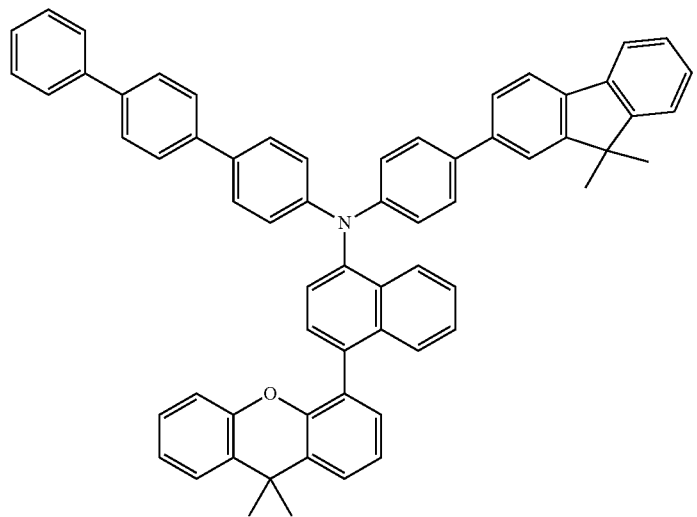

[Chemical Formula 11]
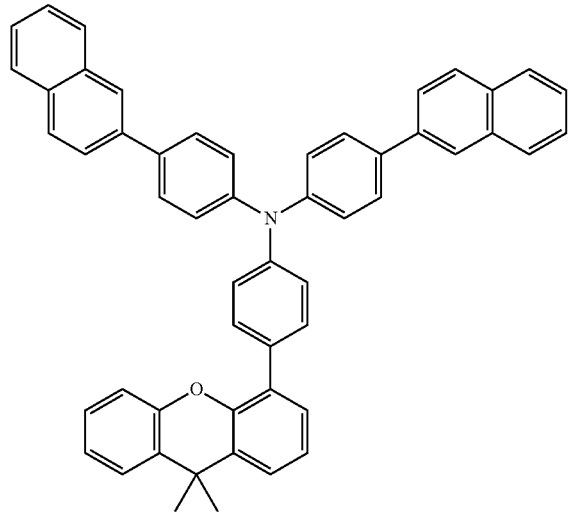
[Chemical Formula 12]
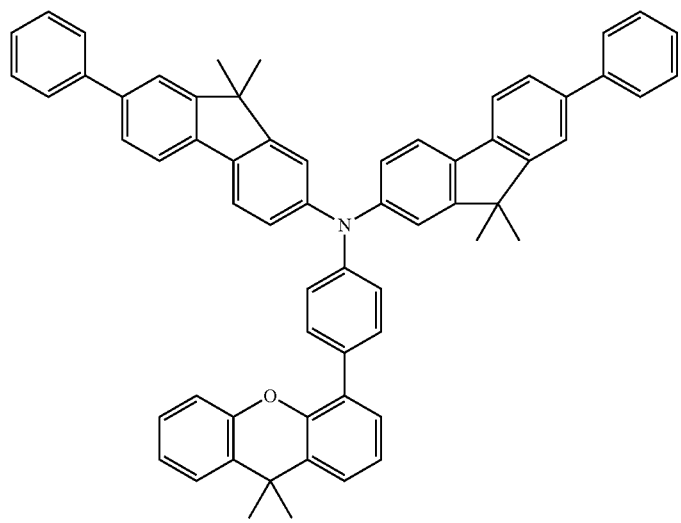
[Chemical Formula 13]
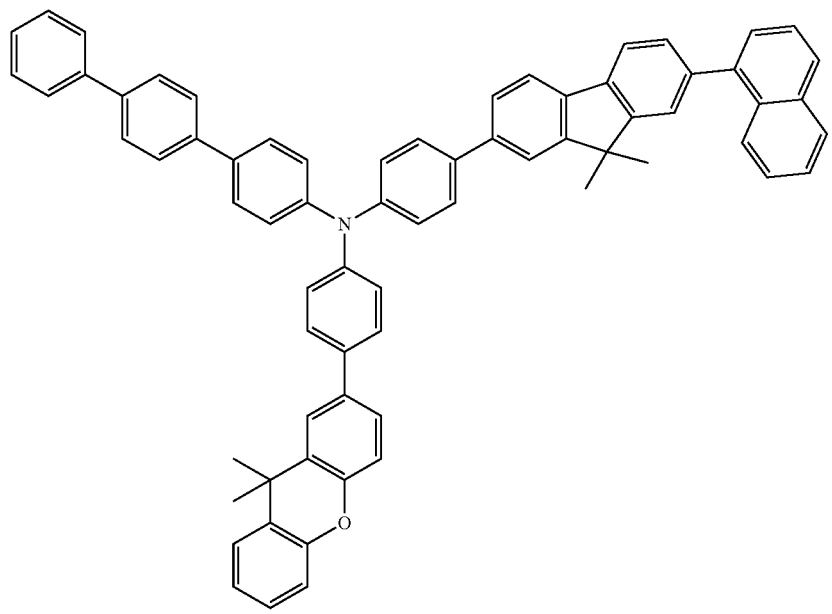

[Chemical Formula 14]
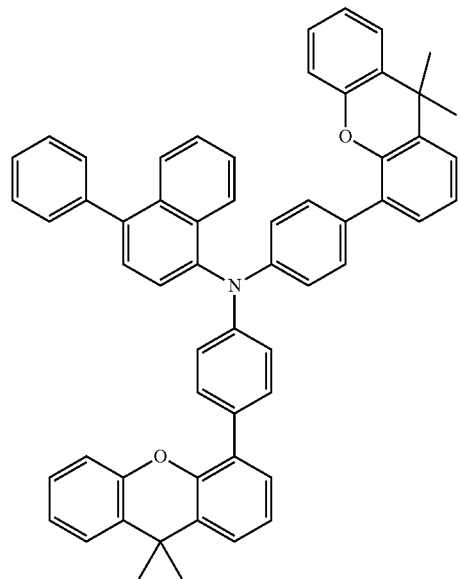
[Chemical Formula 15]
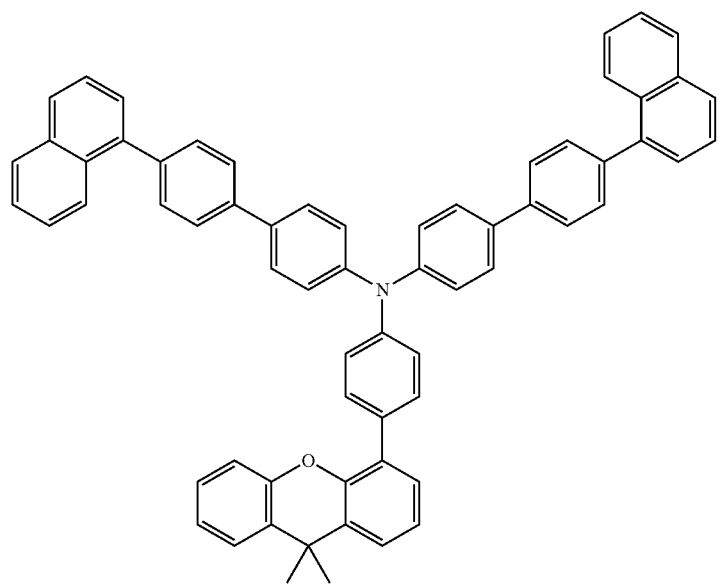

[Chemical Formula 16]
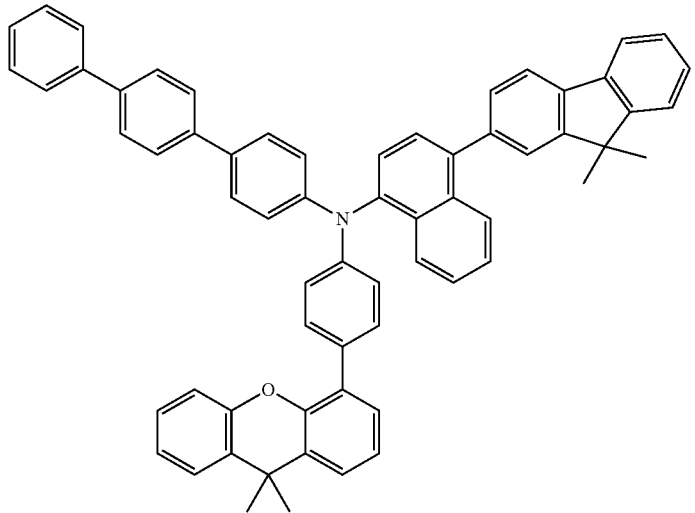
[Chemical Formula 17]
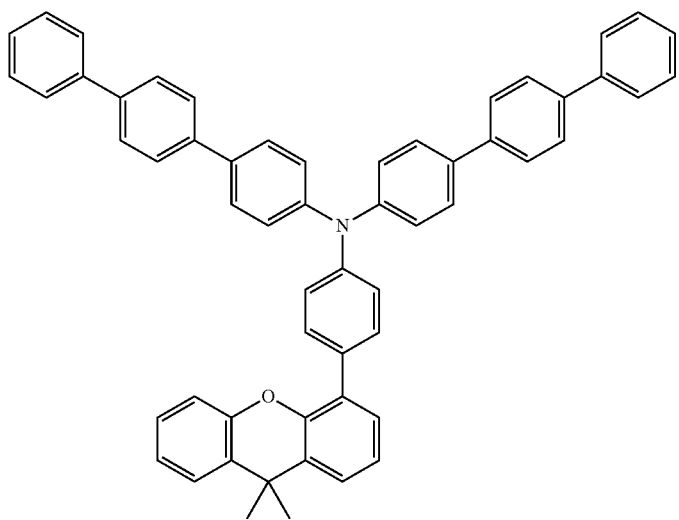
[Chemical Formula 18]
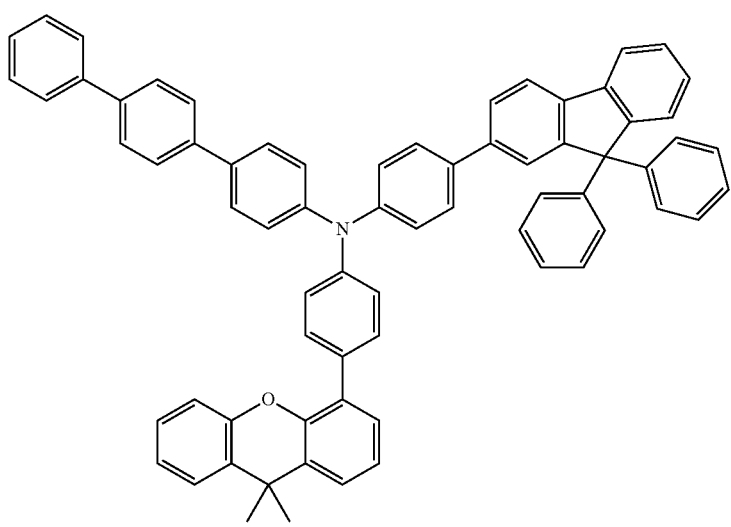

[Chemical Formula 19]
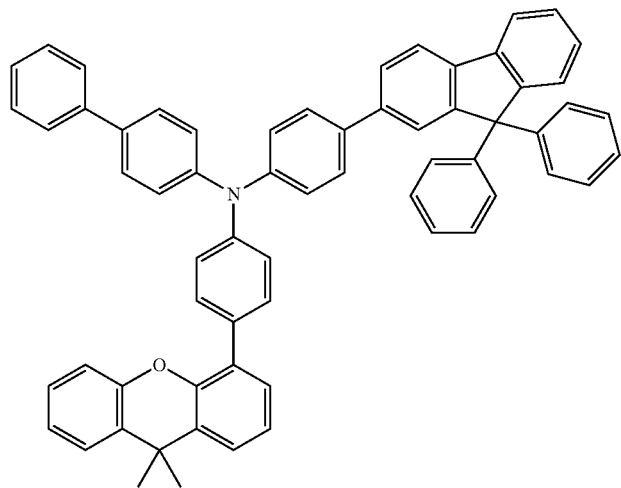
[Chemical Formula 20]
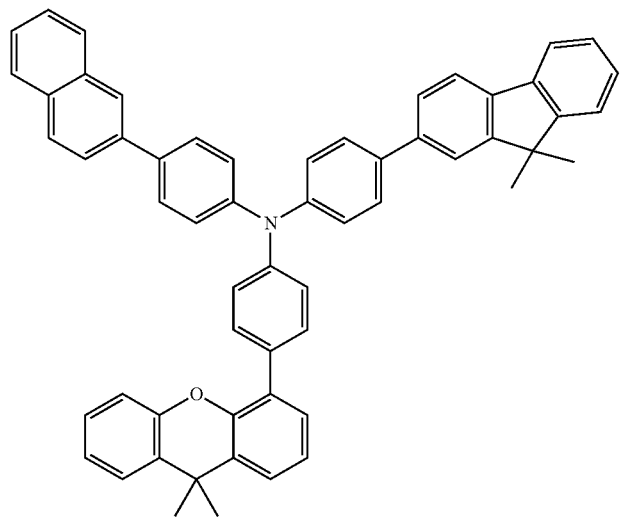

[Chemical Formula 21]
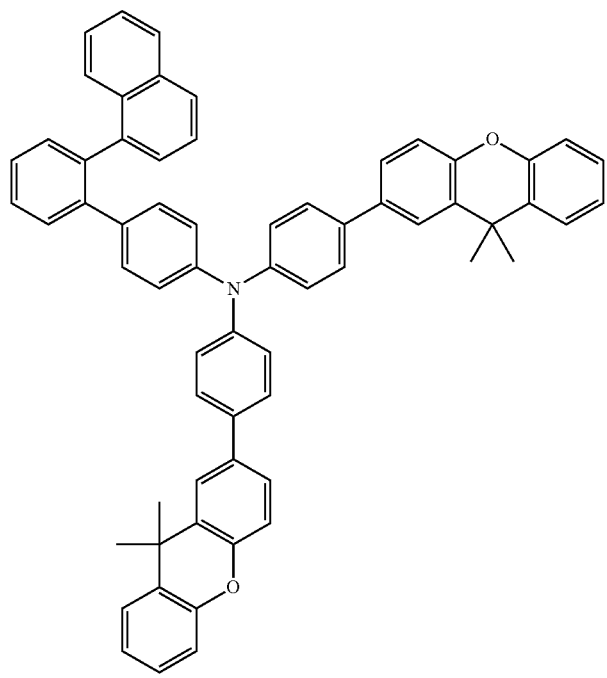
[Chemical Formula 22]
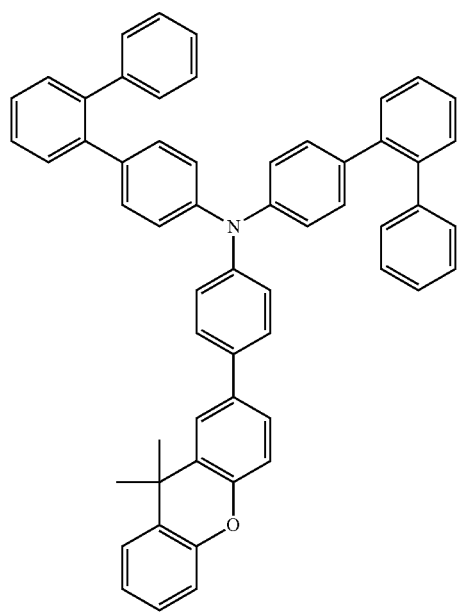

[Chemical Formula 23]
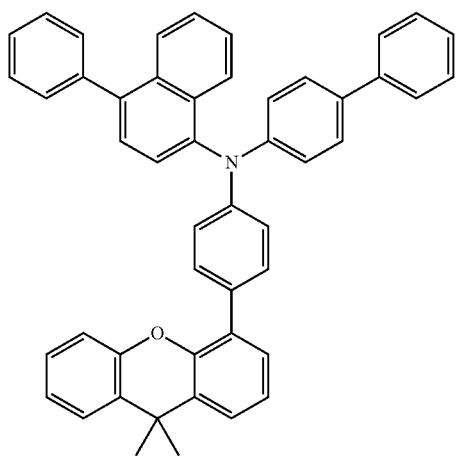
[Chemical Formula 24]
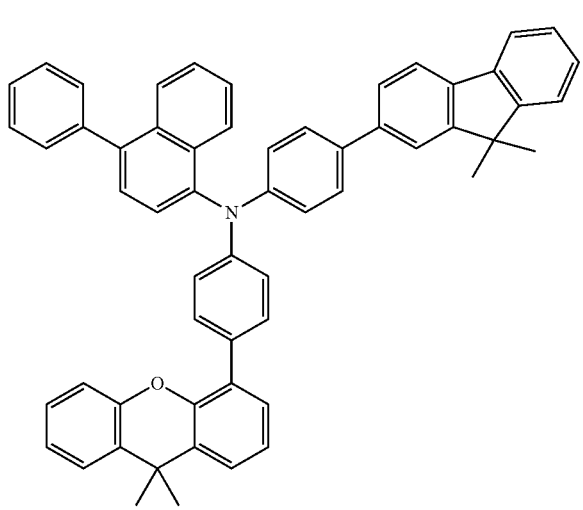
[Chemical Formula 25]
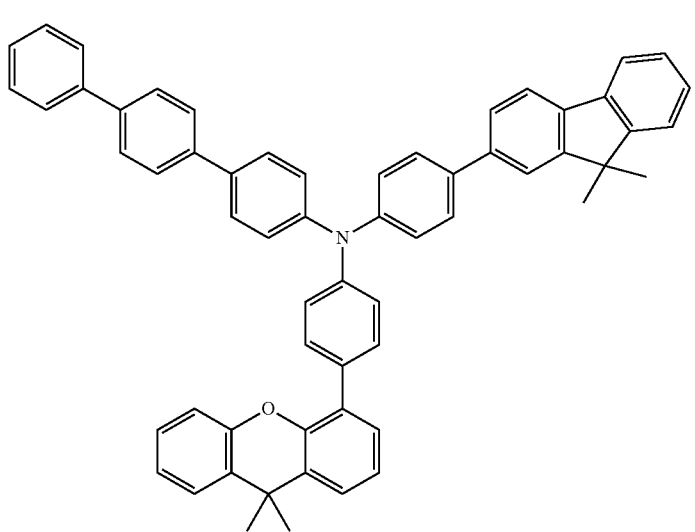

[Chemical Formula 26]
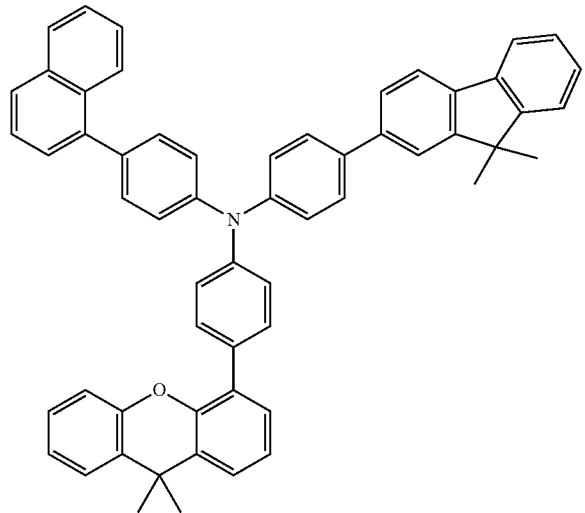
[Chemical Formula 27]
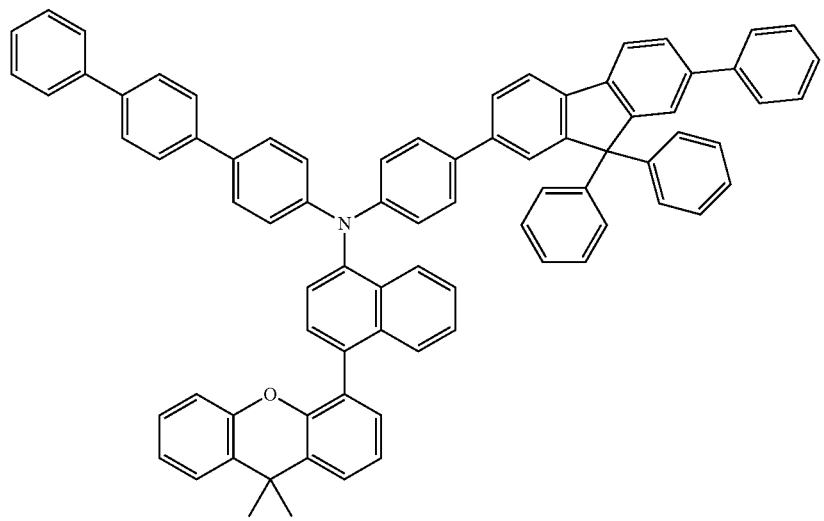
[Chemical Formula 28]
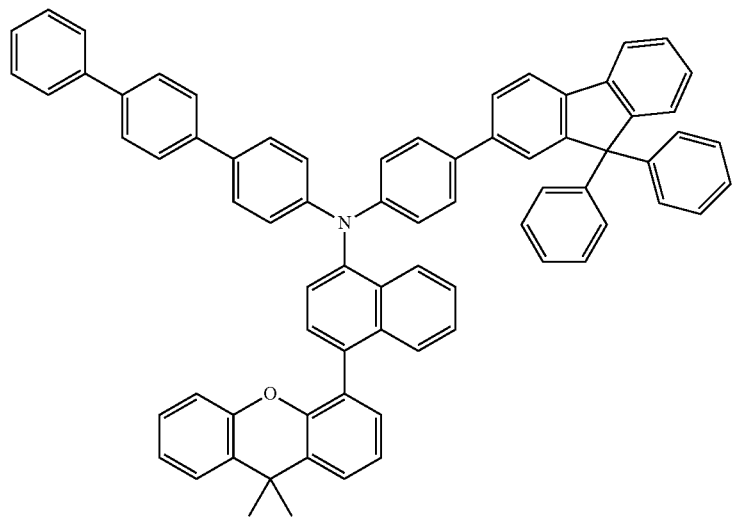

[Chemical Formula 29]
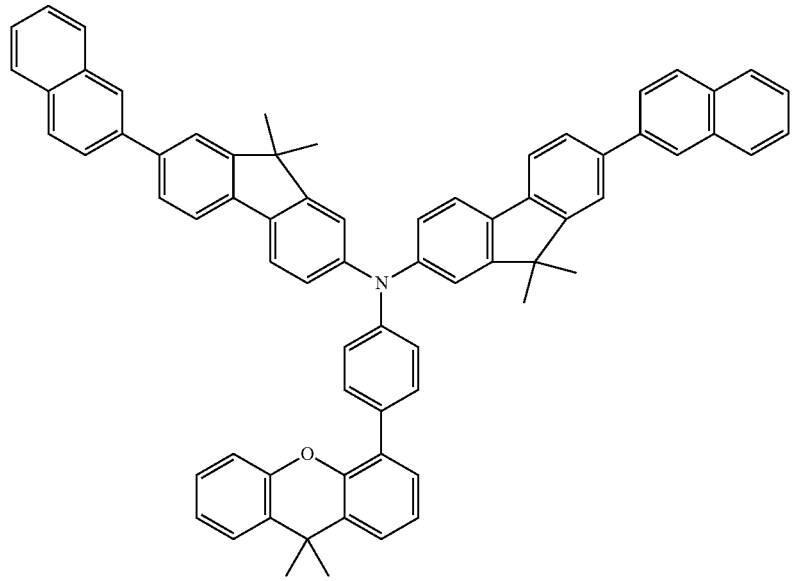
[Chemical Formula 30]
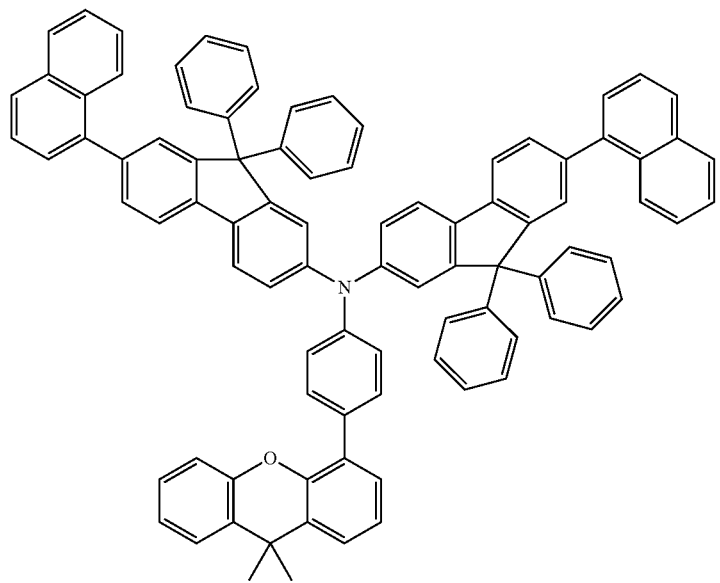

[Chemical Formula 31]
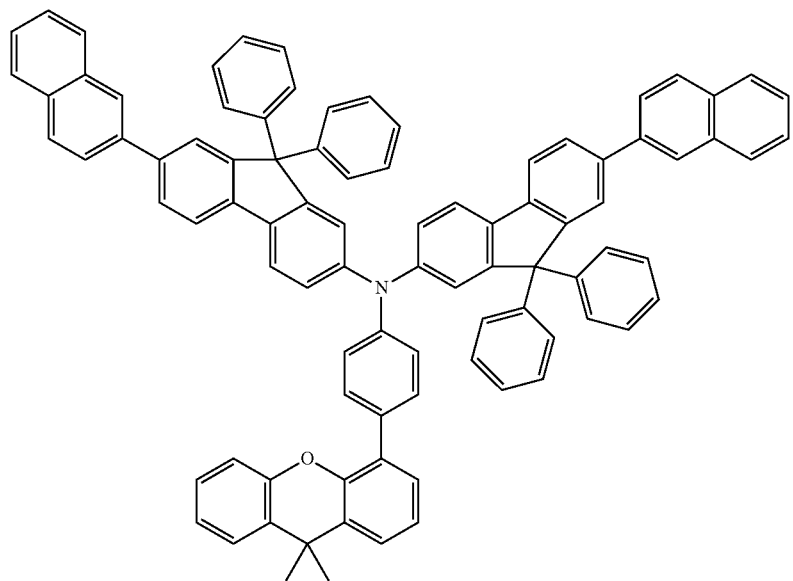
[Chemical Formula 32]
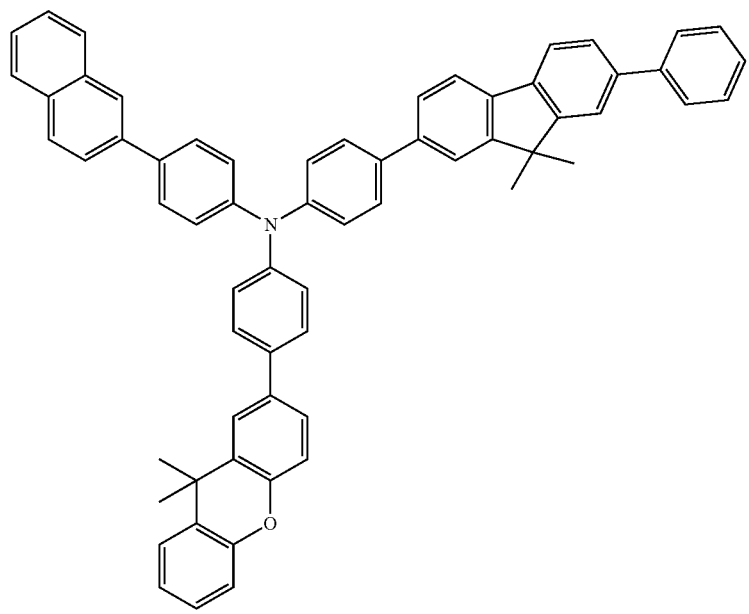

[Chemical Formula 33]
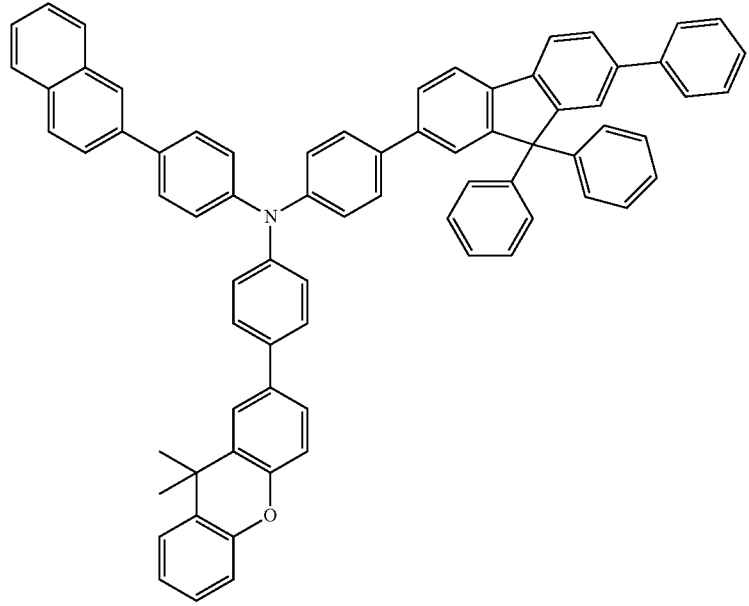
[Chemical Formula 34]
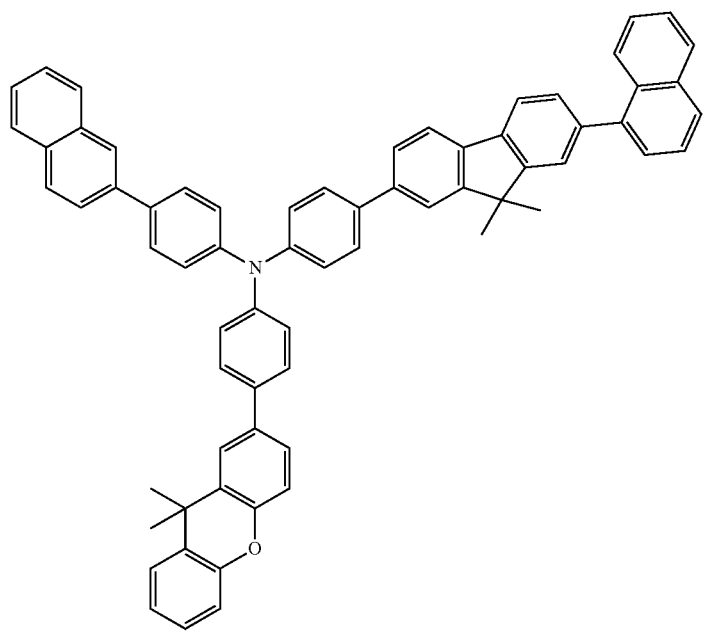

[Chemical Formula 35]
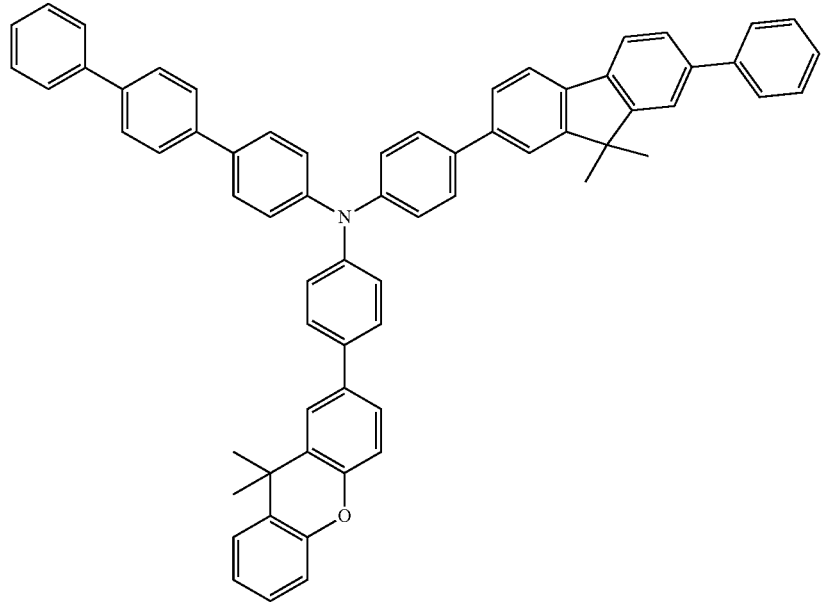
[Chemical Formula 36]
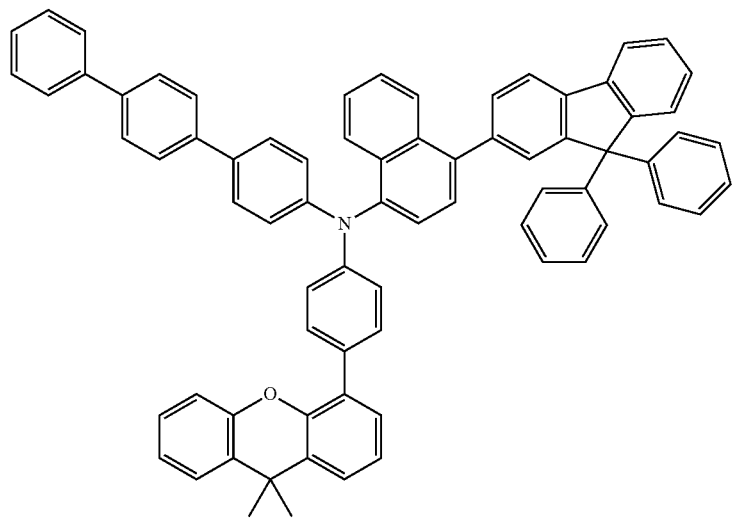
[Chemical Formula 37]
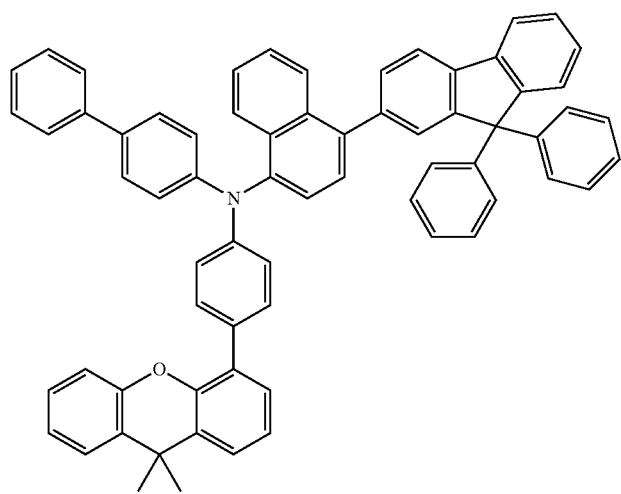

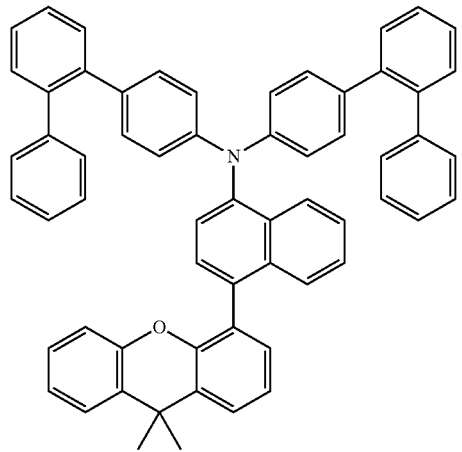
[Chemical Formula 38]
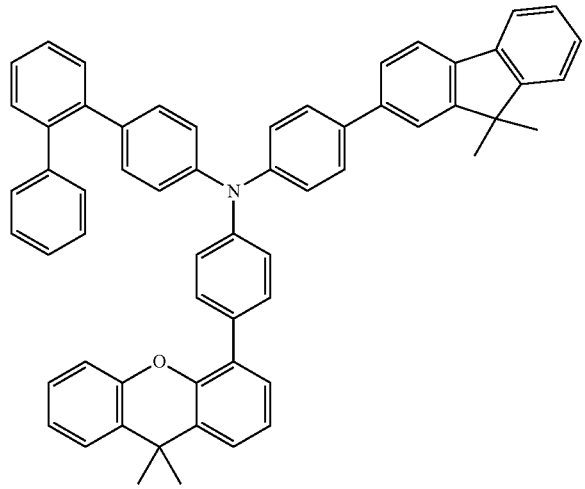
[Chemical Formula 39]
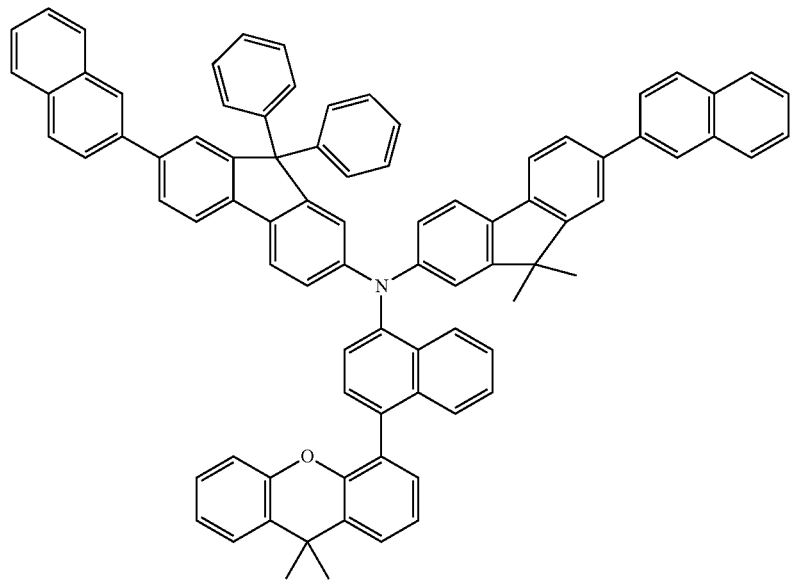
[Chemical Formula 40]

[Chemical Formula 41]
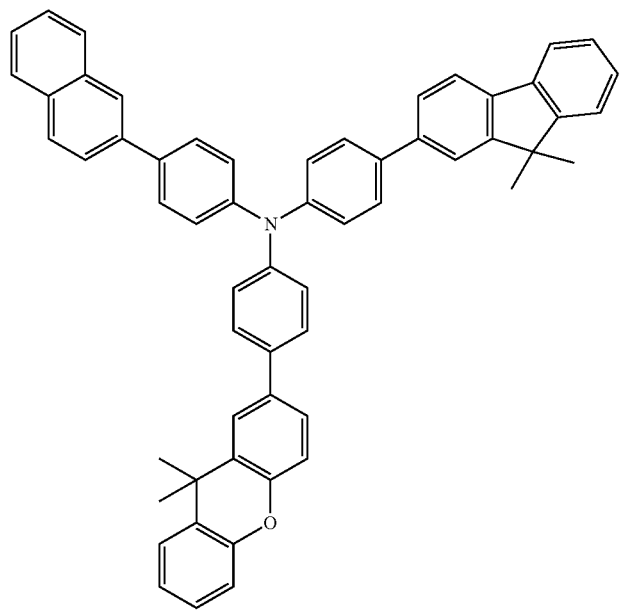
[Chemical Formula 42]
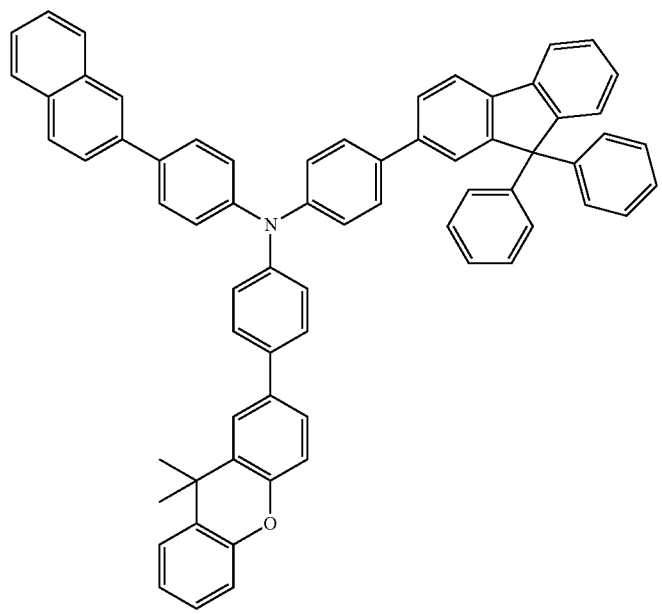

[Chemical Formula 43]
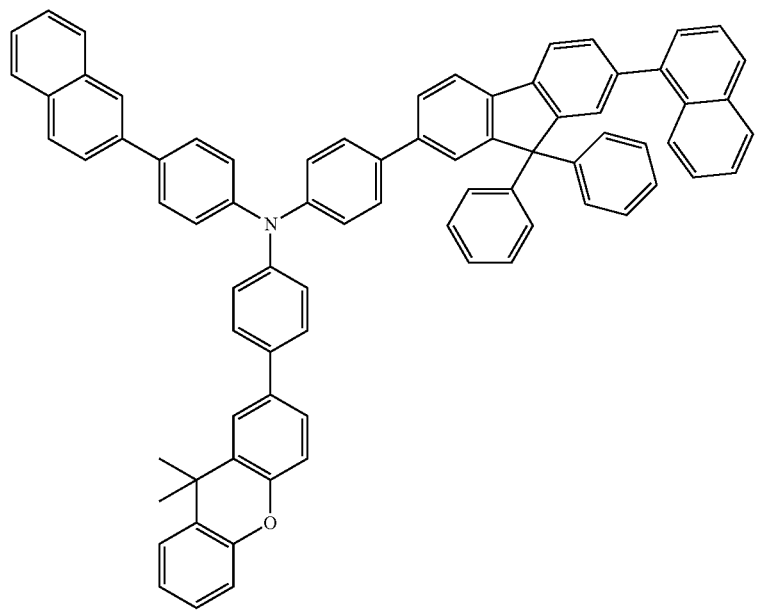
[Chemical Formula 44]
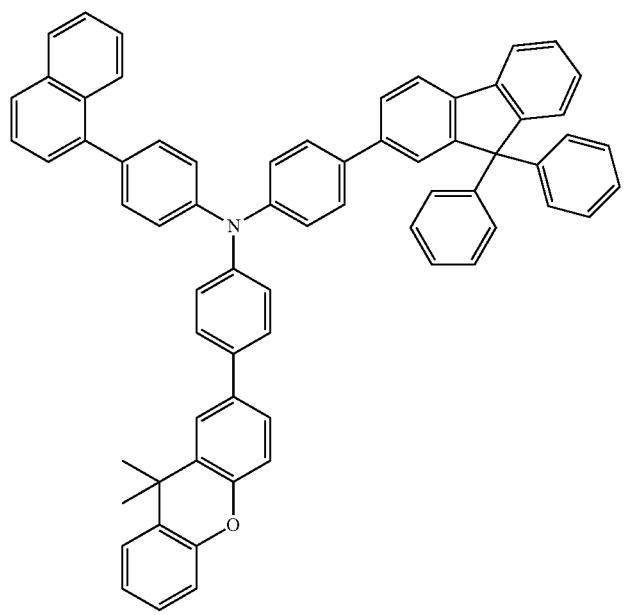

[Chemical Formula 45]
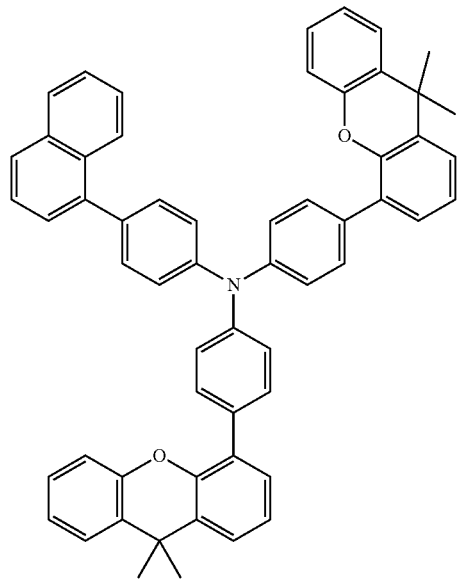
[Chemical Formula 46]
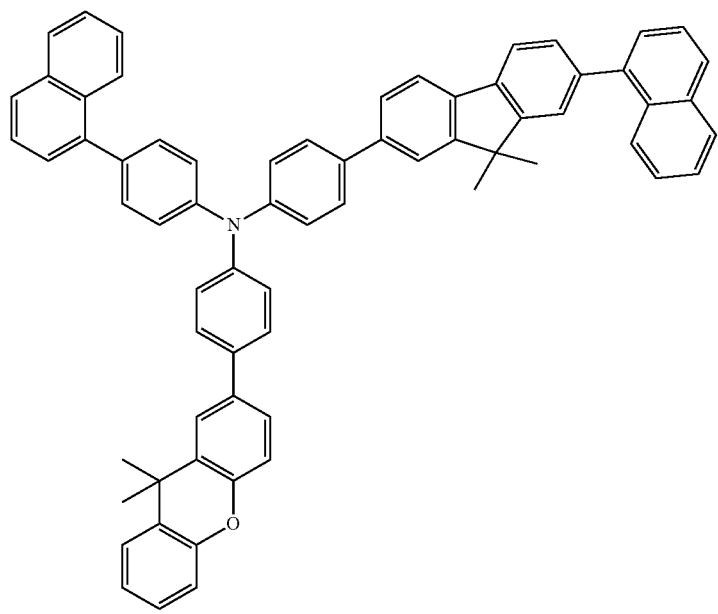

-continued
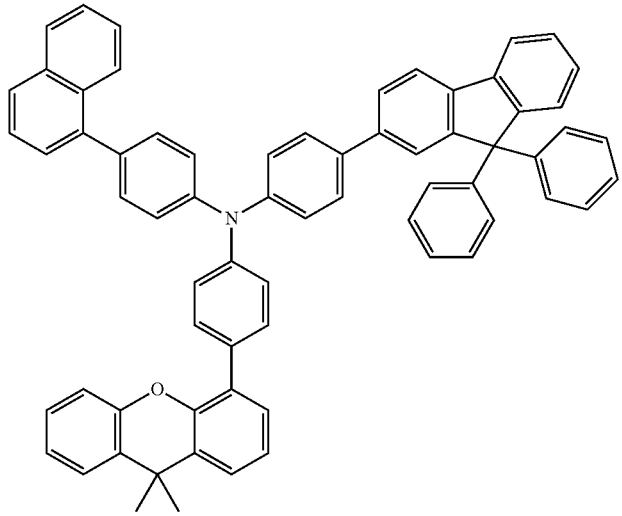
[Chemical Formula 47]
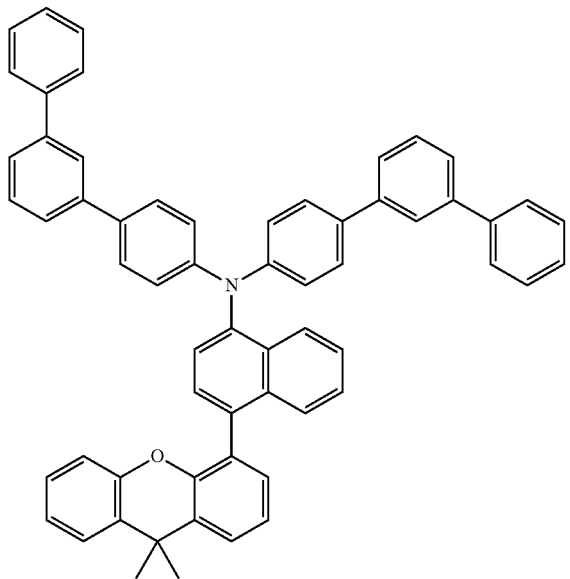
[Chemical Formula 48]
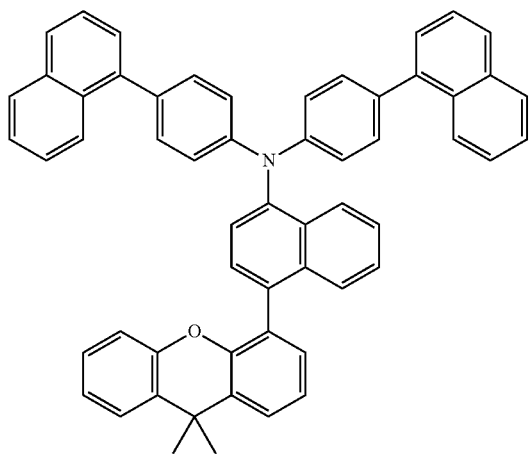
[Chemical Formula 49]

[Chemical Formula 50]
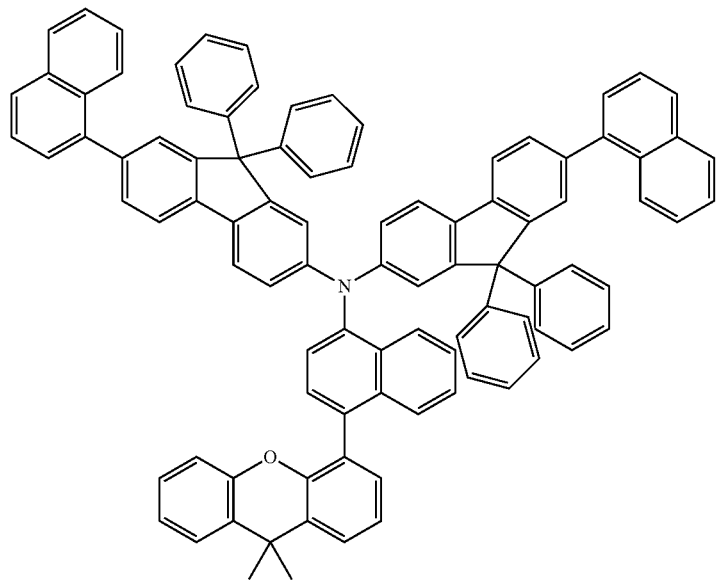
[Chemical Formula 51]
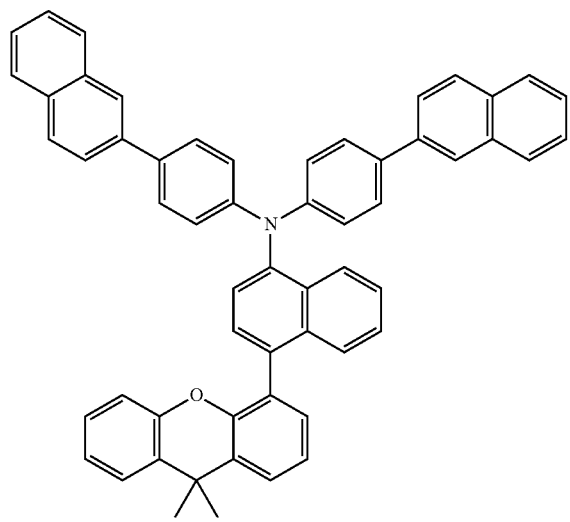

[Chemical Formula 52]
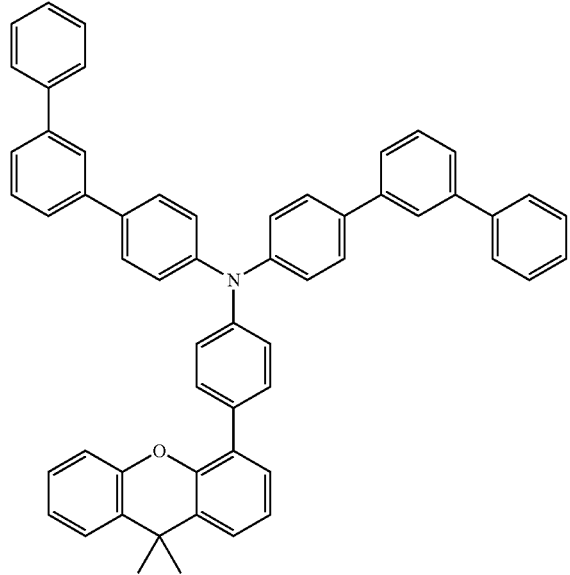
[Chemical Formula 53]
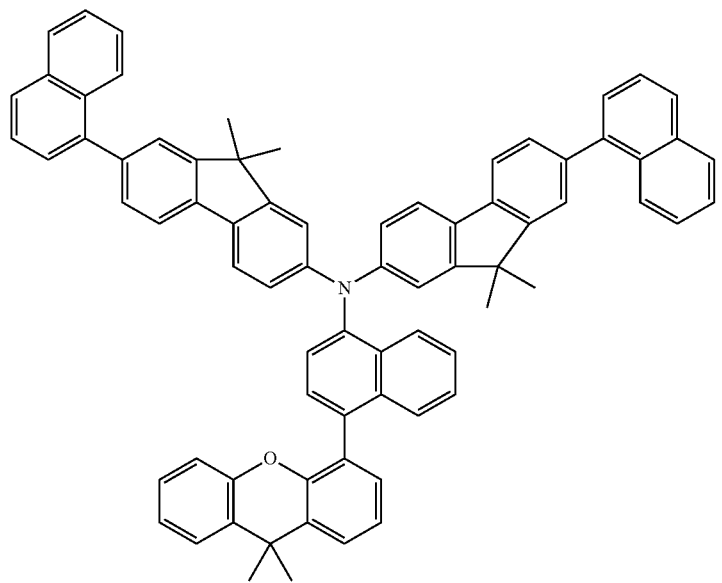

-continued
[Chemical Formula 54]
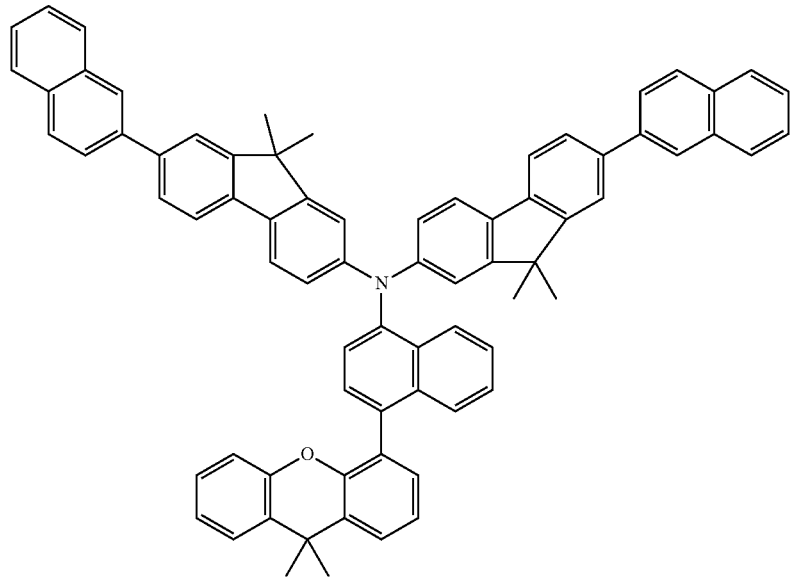
[Chemical Formula 55]
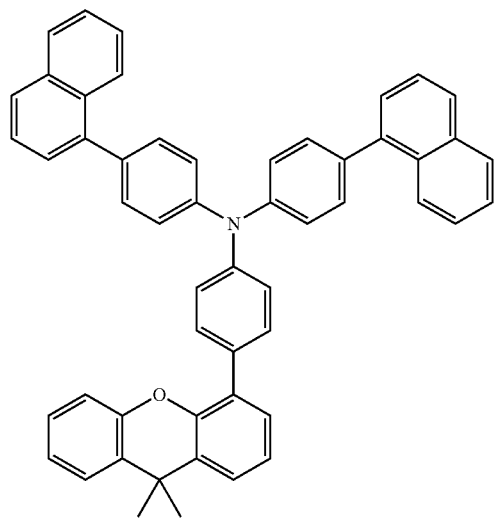

-continued
[Chemical Formula 56]
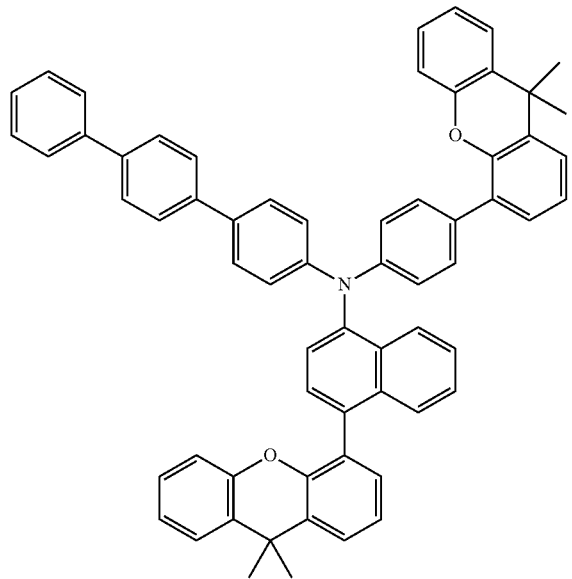
[Chemical Formula 57]
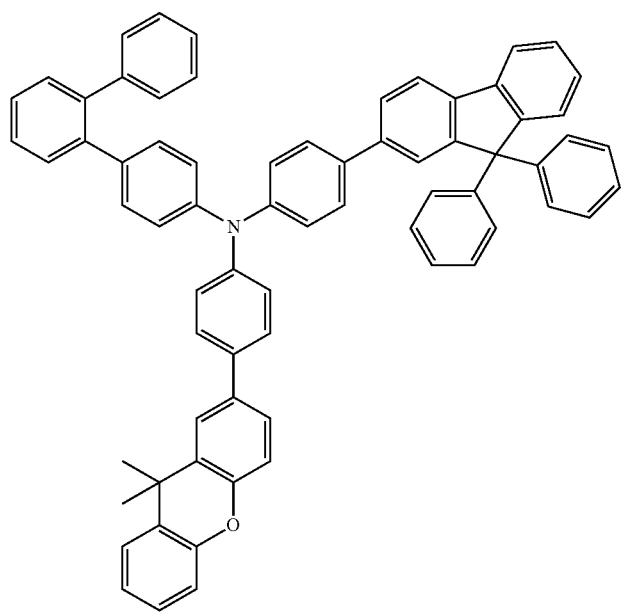

[Chemical Formula 58]
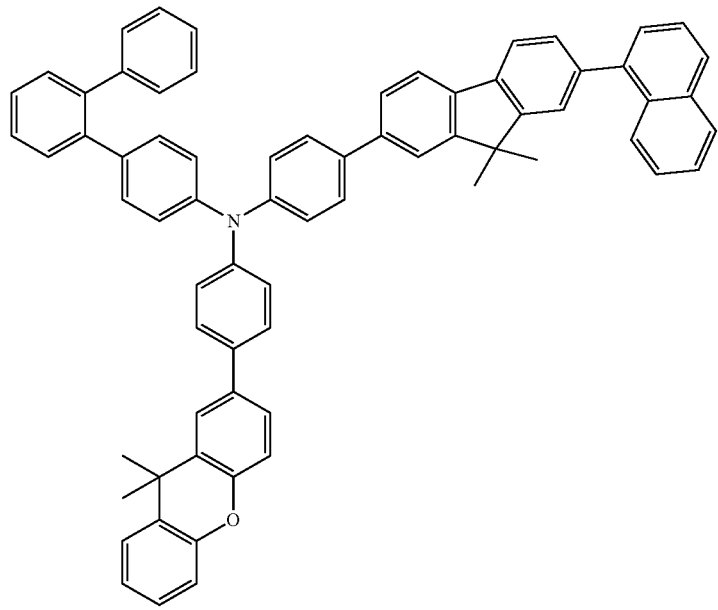
[Chemical Formula 59]
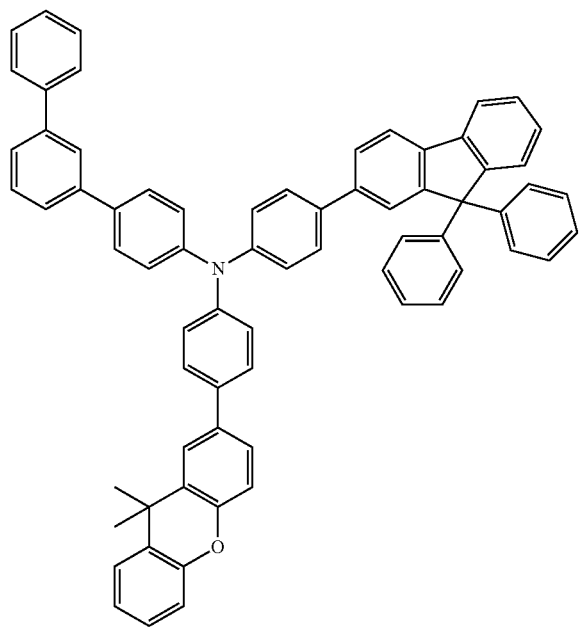

[Chemical Formula 60]
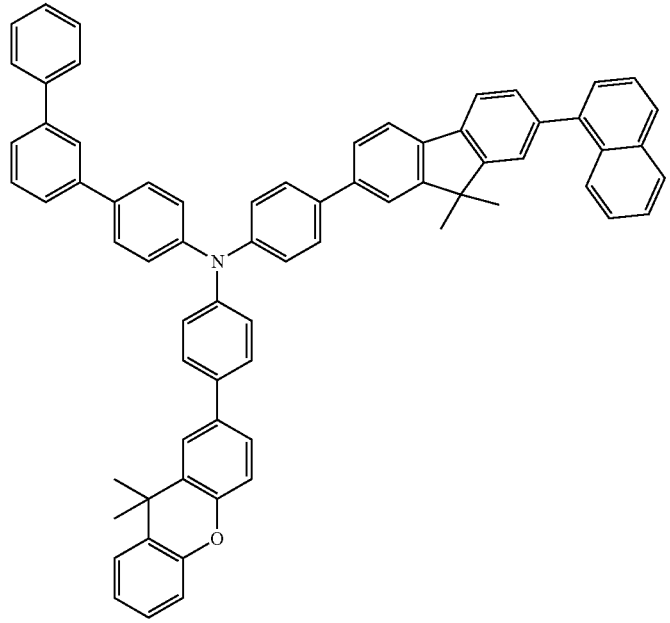
[Chemical Formula 61]
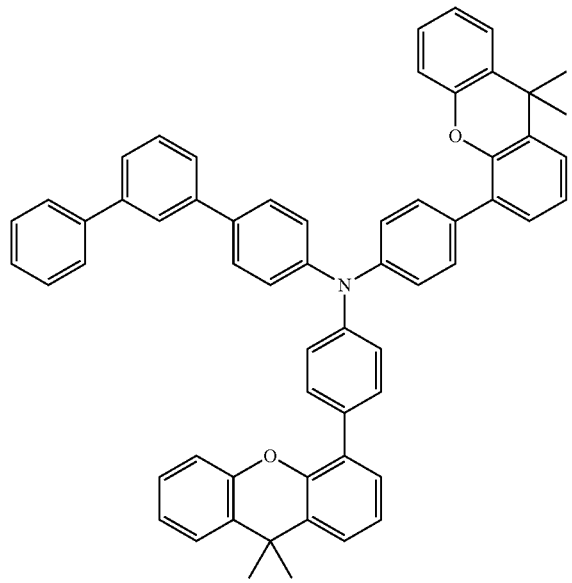

-continued
[Chemical Formula 62]
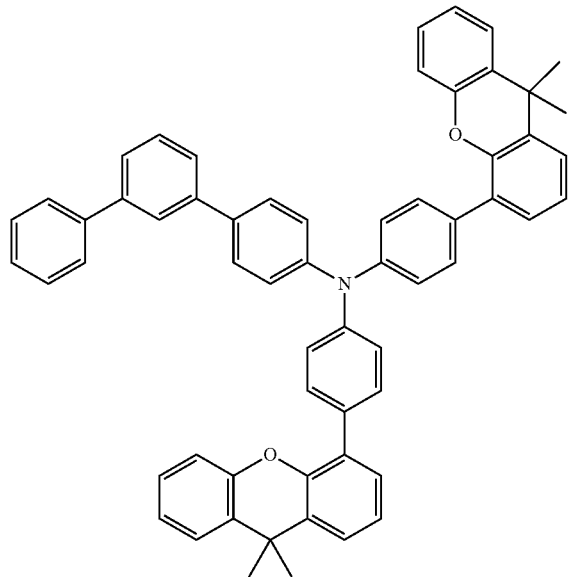
[Chemical Formula 63]
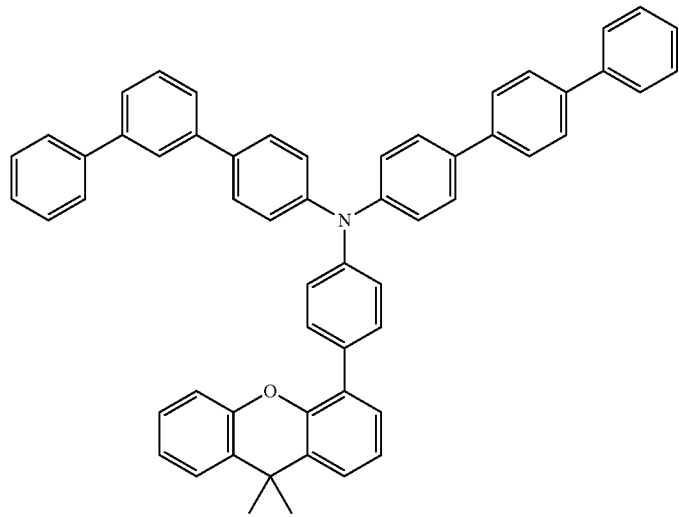
[Chemical Formula 64]
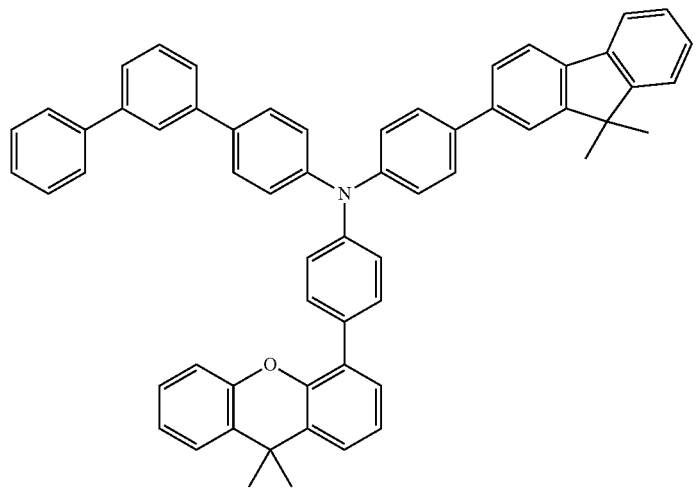

-continued
[Chemical Formula 65]
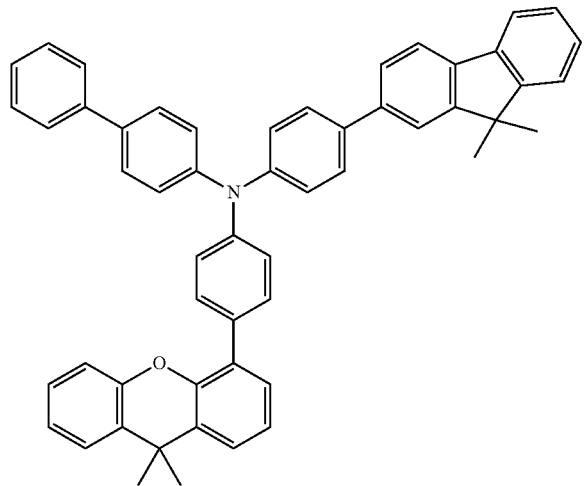
[Chemical Formula 66]
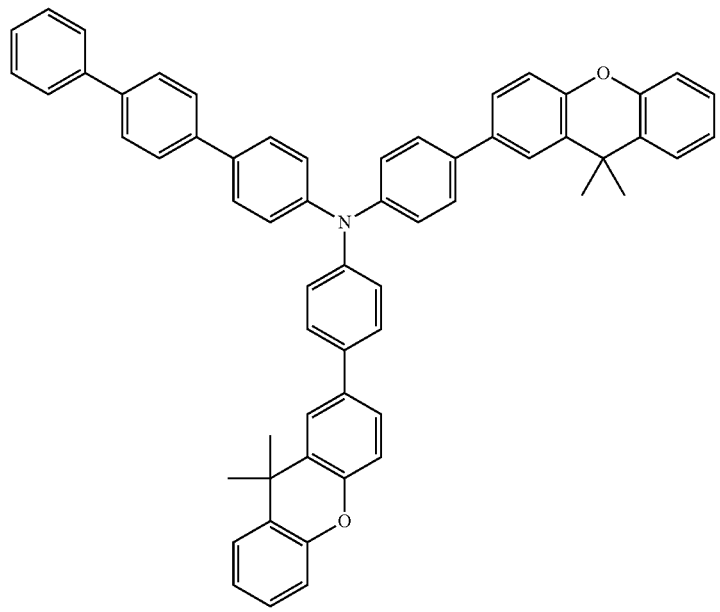

[Chemical Formula 67]
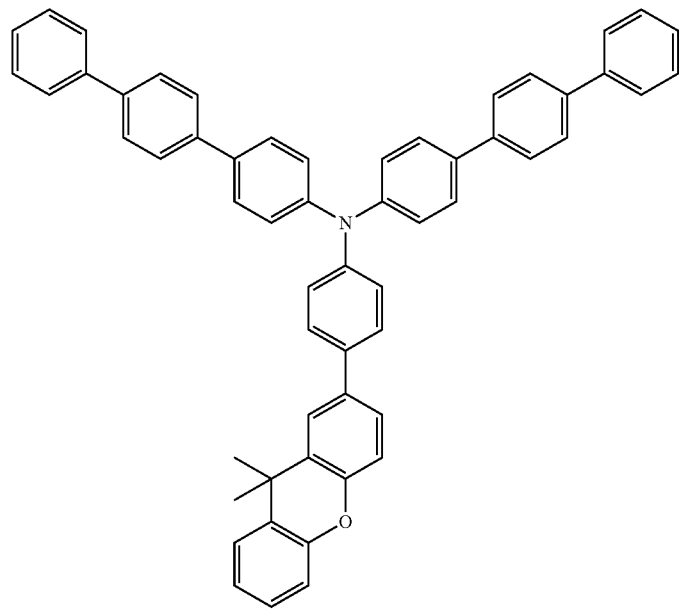
[Chemical Formula 68]
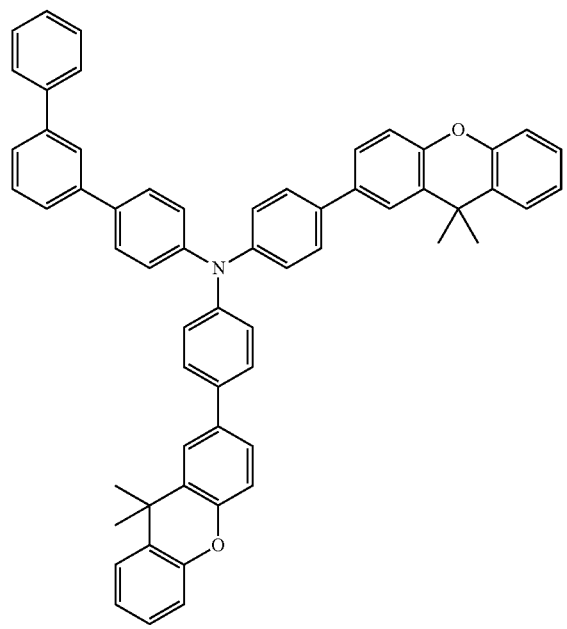

[Chemical Formula 69]
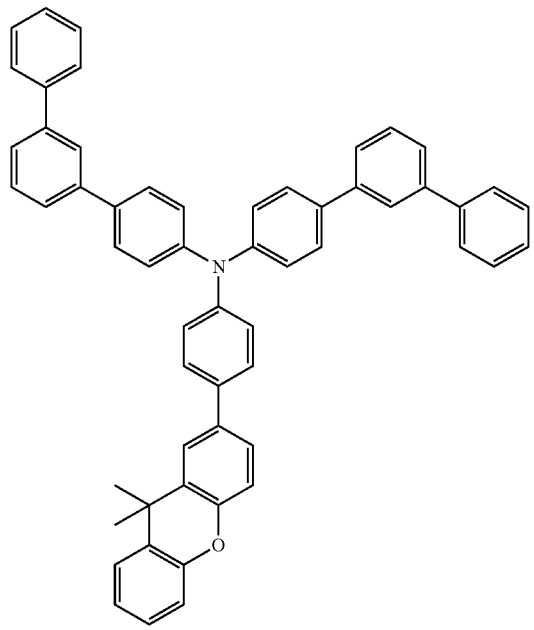
[Chemical Formula 70]
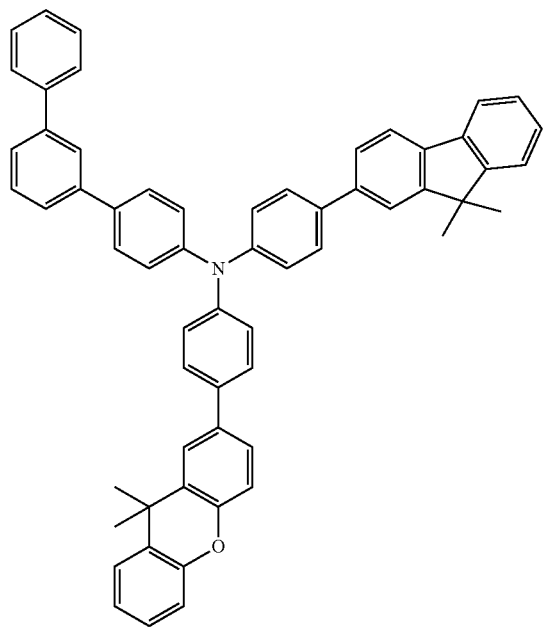

-continued
[Chemical Formula 71]
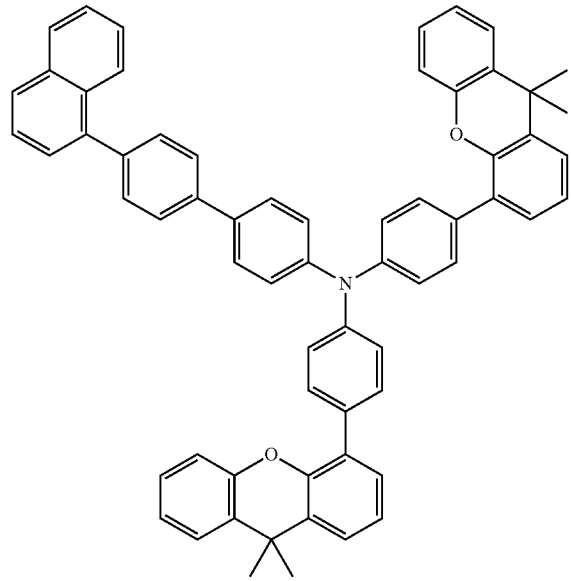
[Chemical Formula 72]
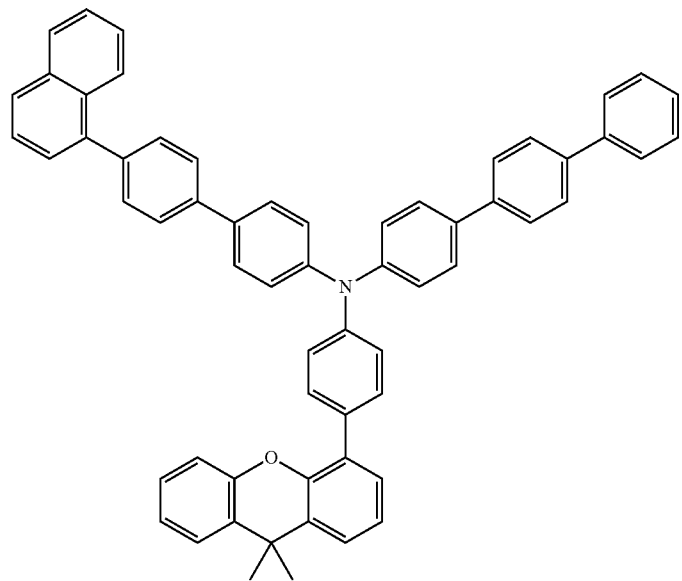

[Chemical Formula 73]
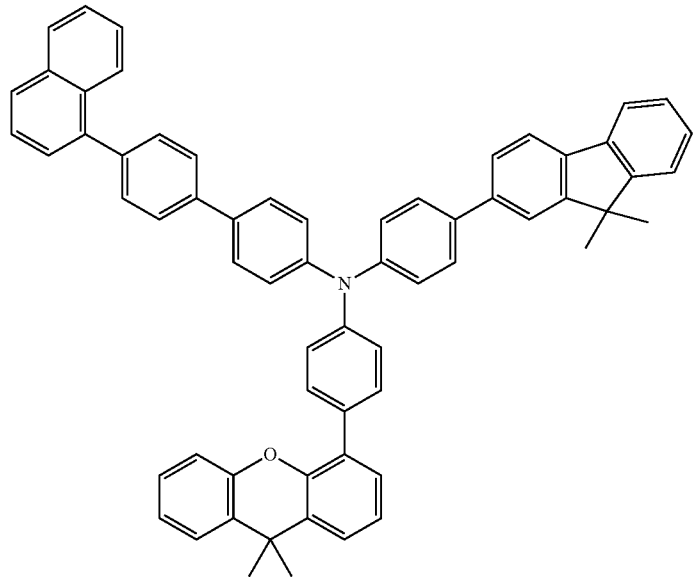
[Chemical Formula 74]
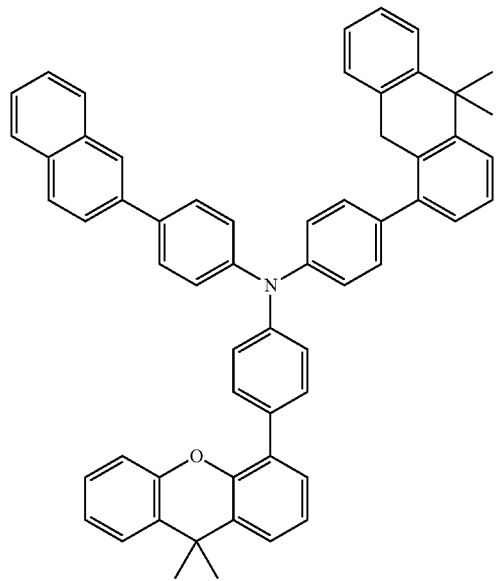

[Chemical Formula 75]
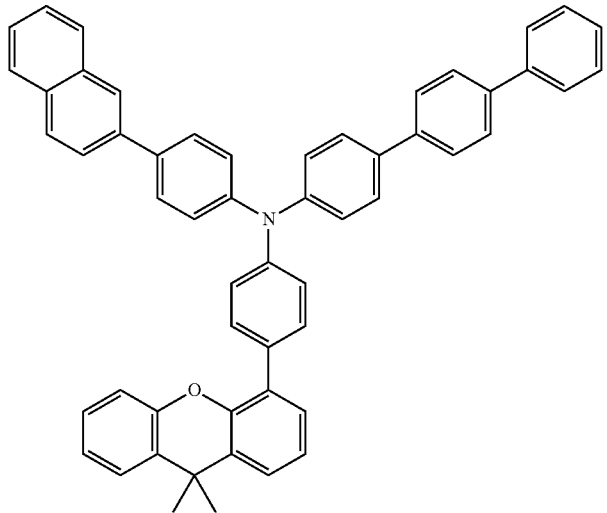
[Chemical Formula 76]
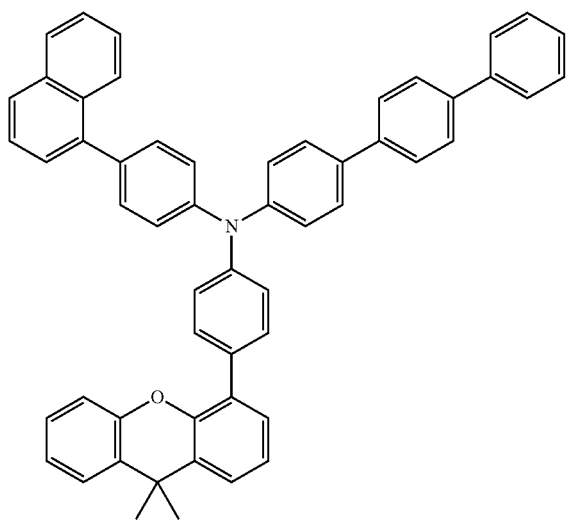
[Chemical Formula 77]
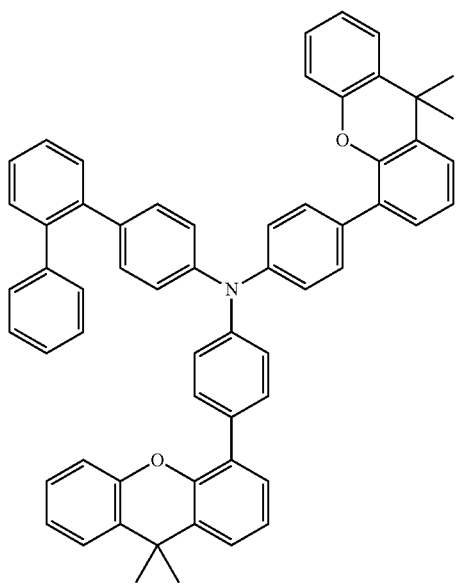

-continued
[Chemical Formula 78]
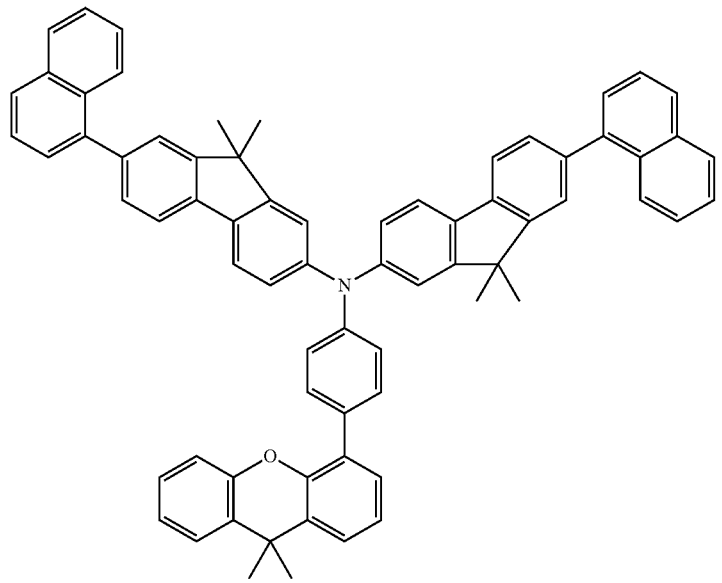
[Chemical Formula 79]
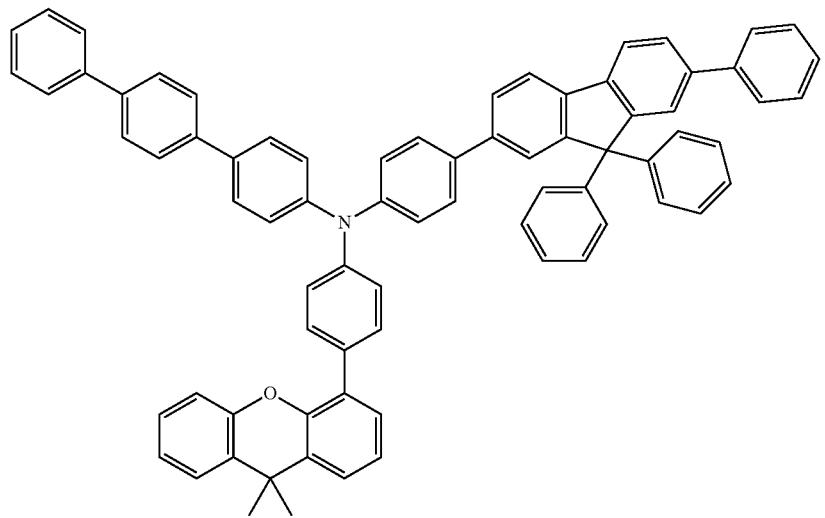
[Chemical Formula 80]
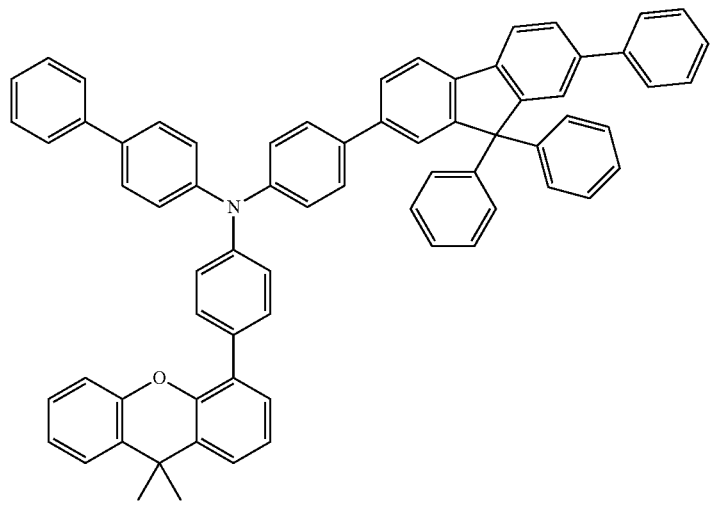

[Chemical Formula 81]
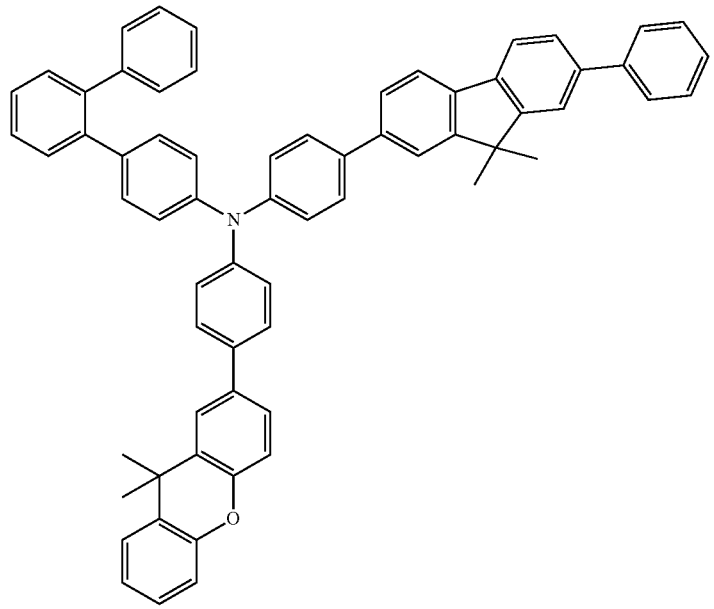
[Chemical Formula 82]
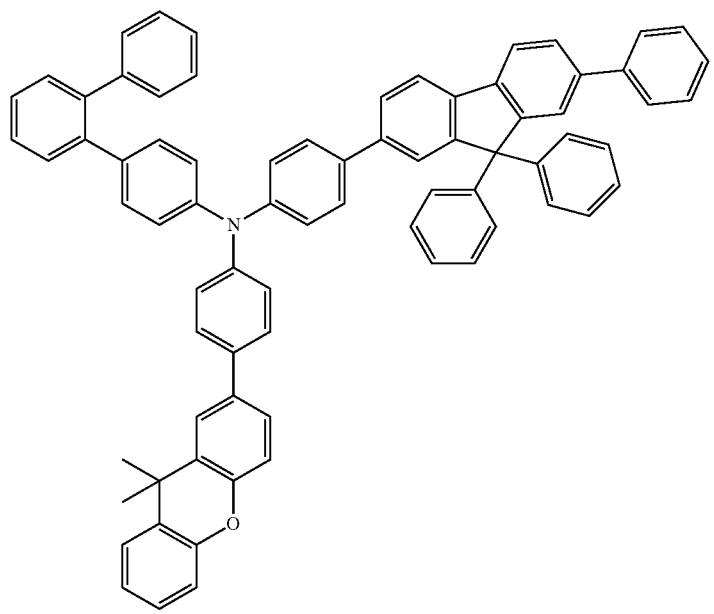

[Chemical Formula 83]
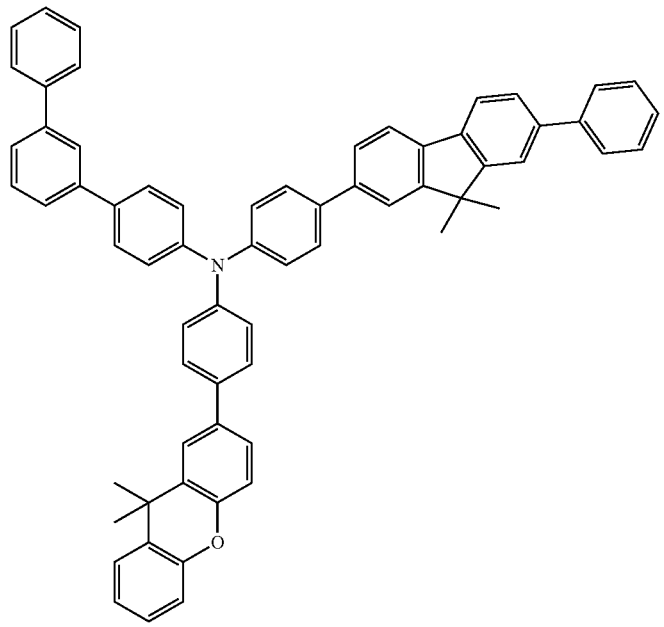
[Chemical Formula 84]
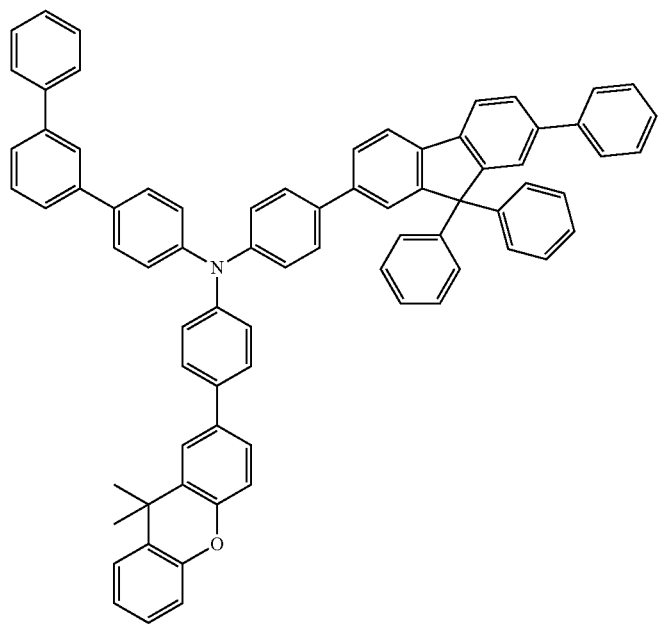

-continued
[Chemical Formula 85]
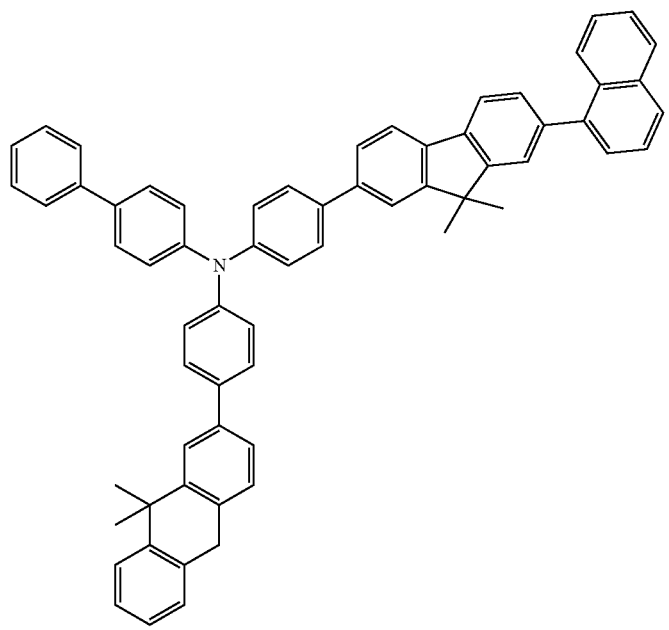
[Chemical Formula 86]
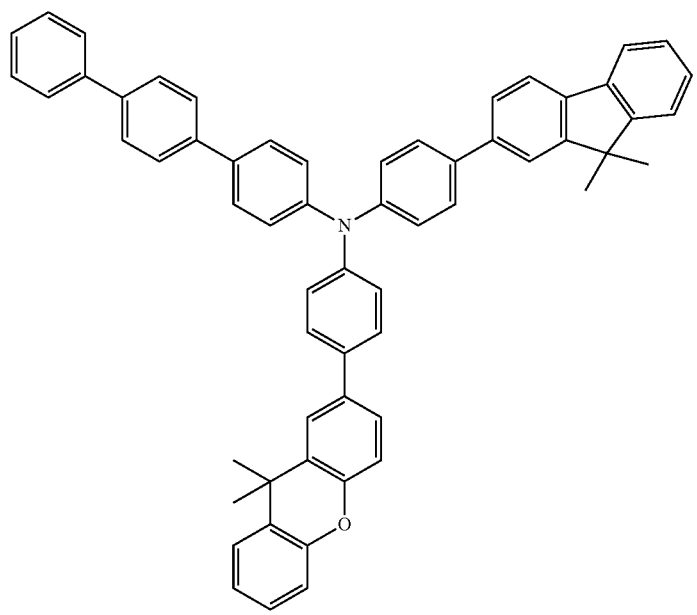

[Chemical Formula 87]
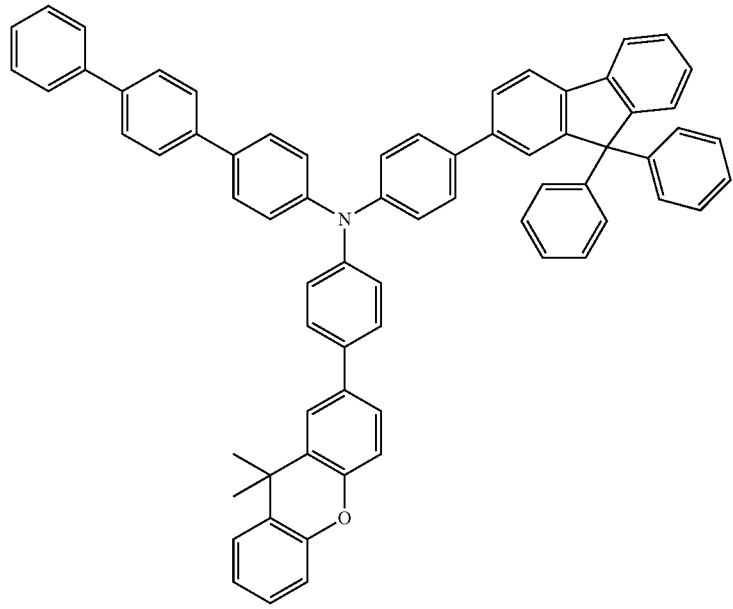
[Chemical Formula 88]
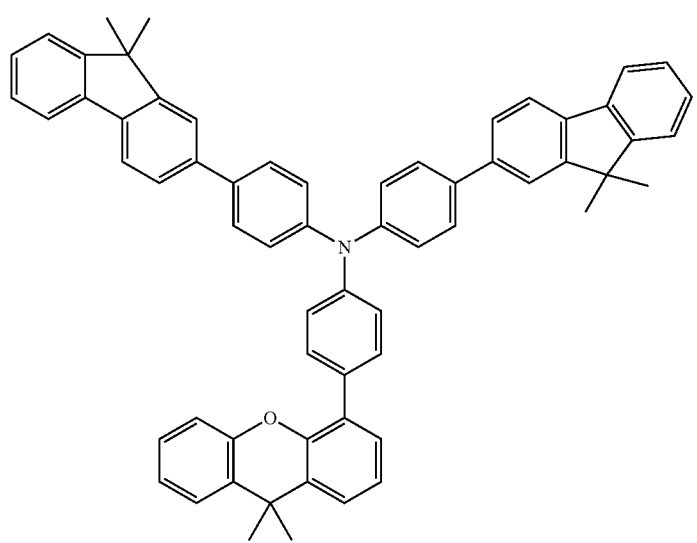

-continued
[Chemical Formula 89]
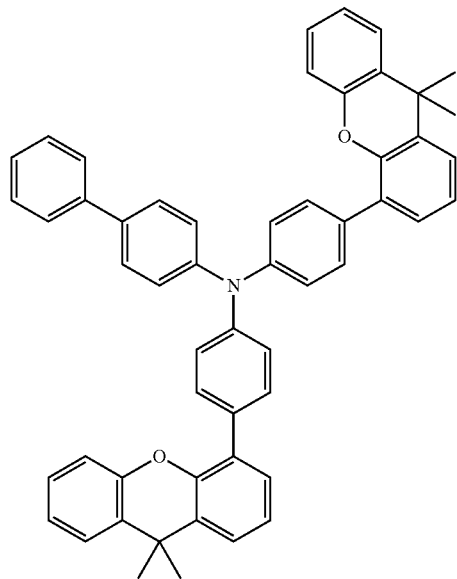
[Chemical Formula 90]
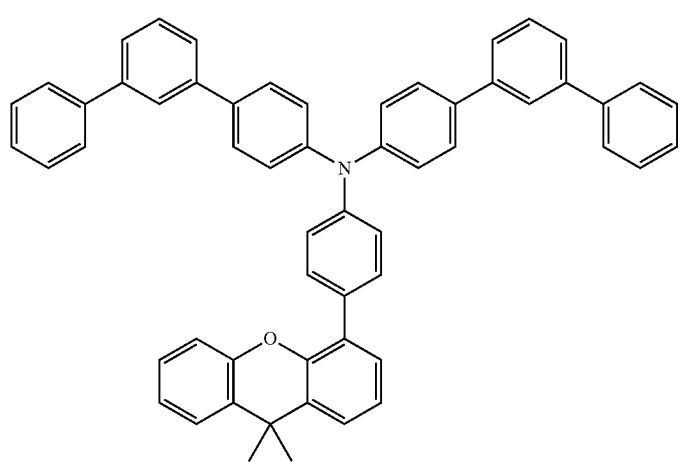
[Chemical Formula 91]
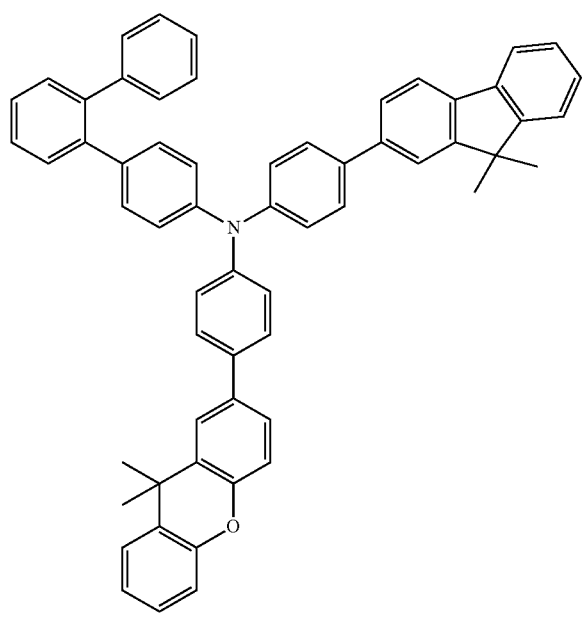

[Chemical Formula 92]
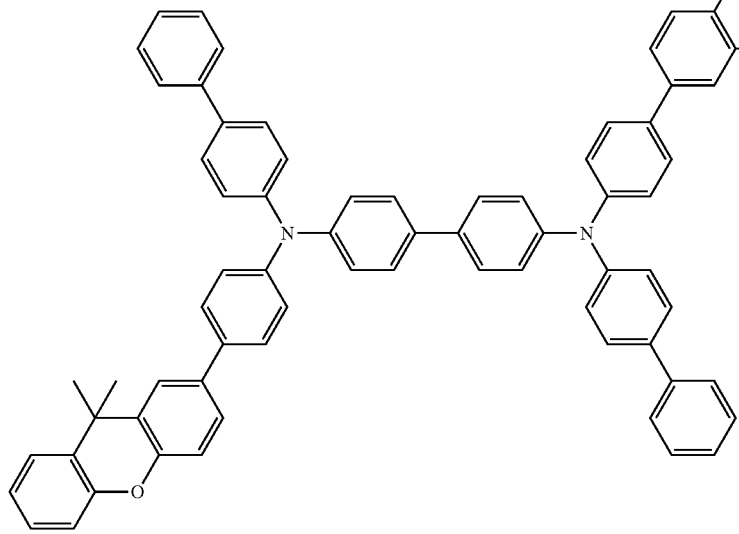
[Chemical Formula 93]
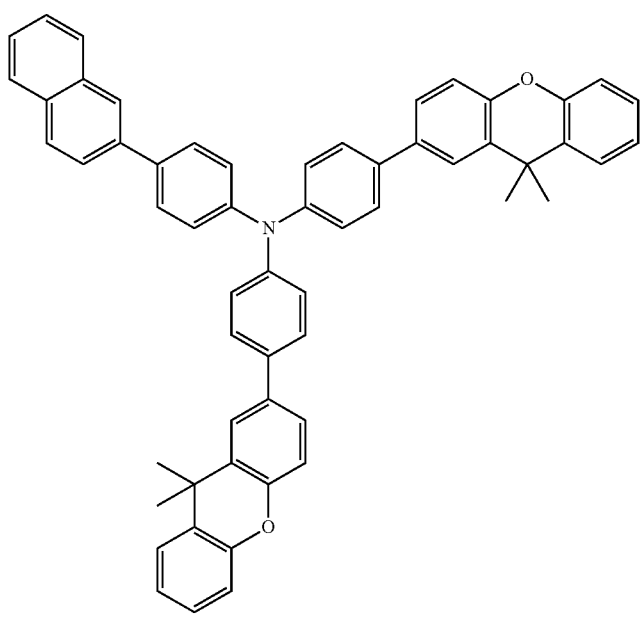

[Chemical Formula 94]
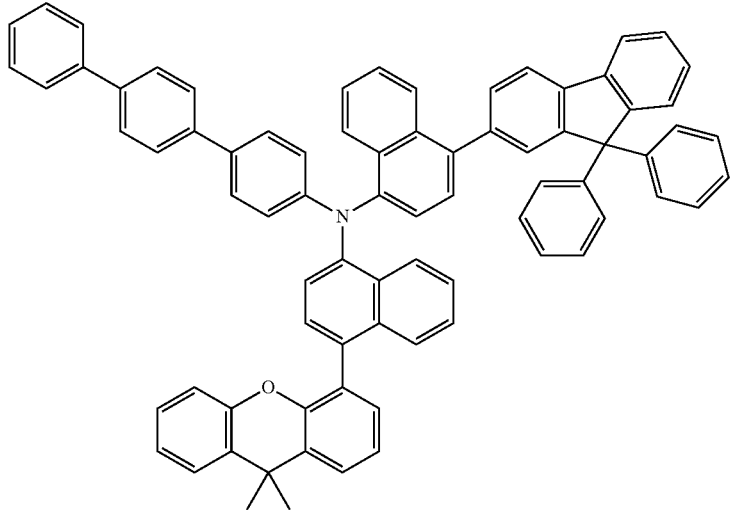
[Chemical Formula 95]
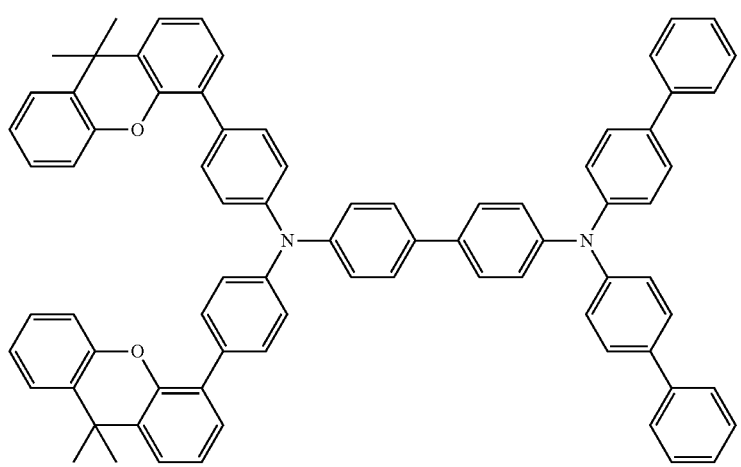
[Chemical Formula 96]
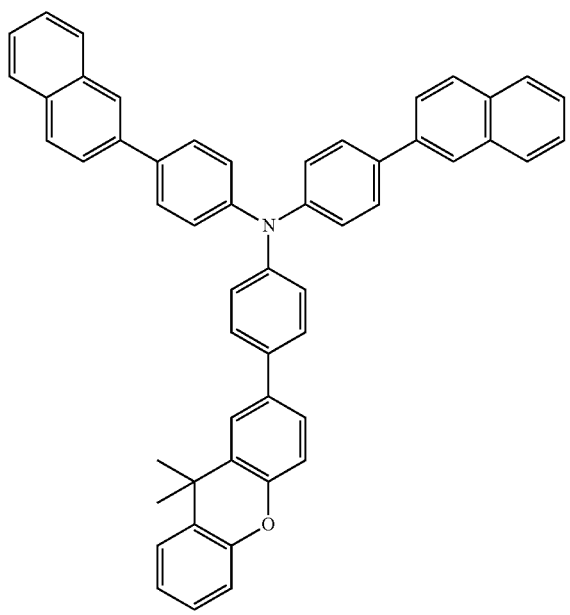

[Chemical Formula 97]
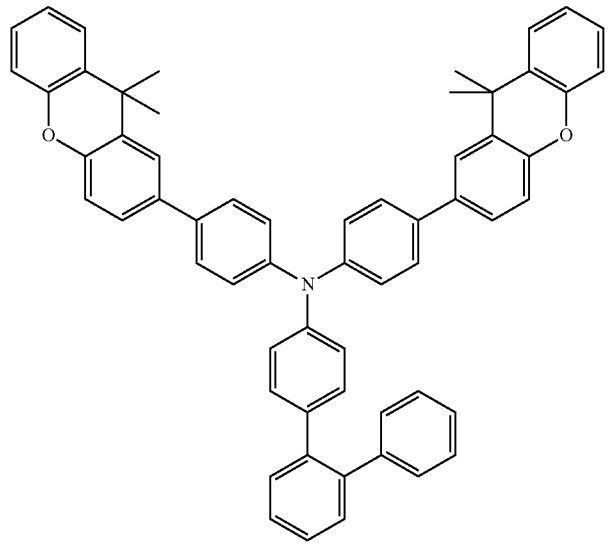
[Chemical Formula 98]
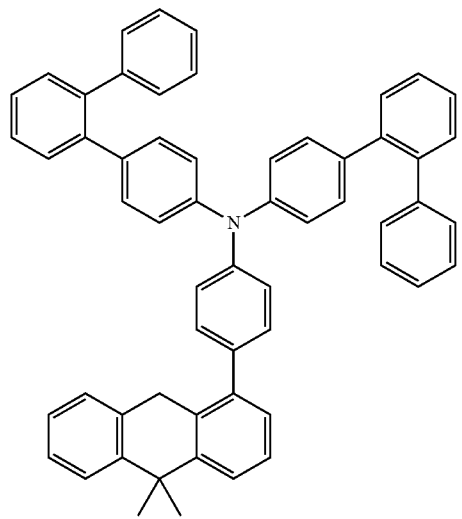

[Chemical Formula 99]
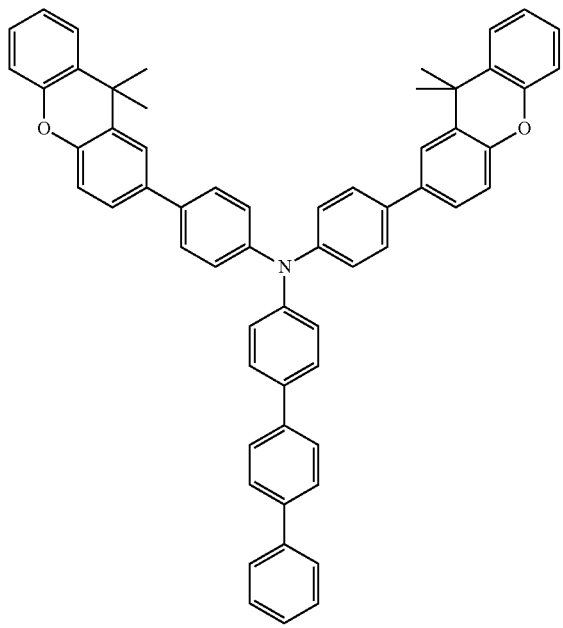
[Chemical Formula 100]
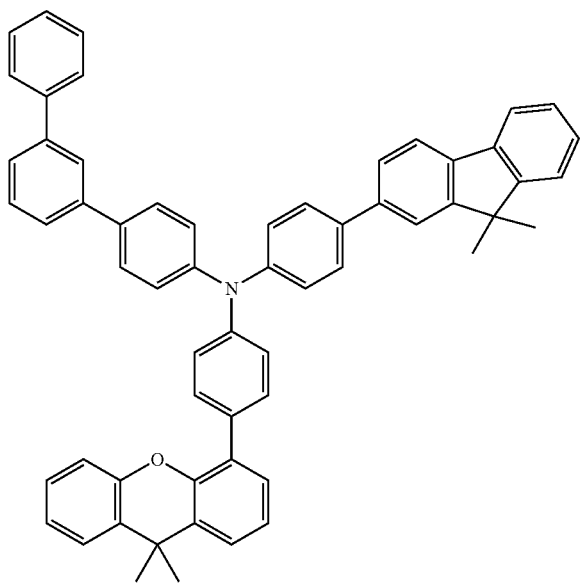
[Chemical Formula 101]
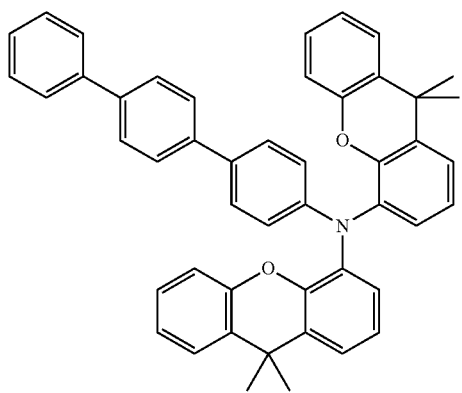

[Chemical Formula 102]
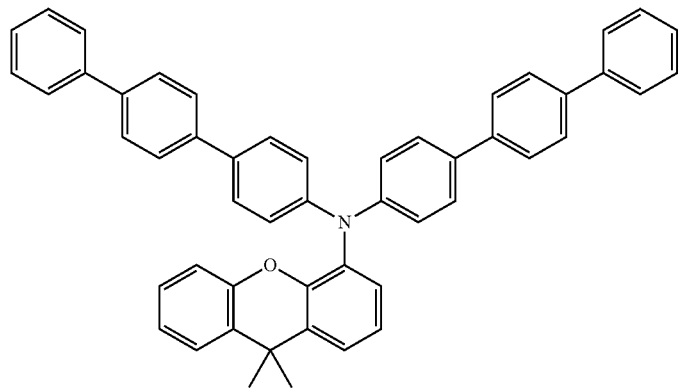
[Chemical Formula 103]
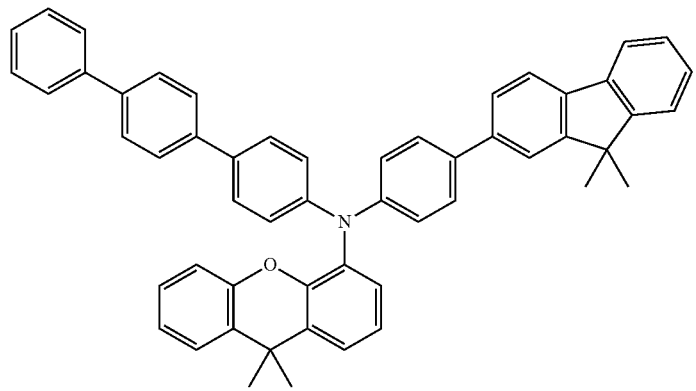
[Chemical Formula 104]
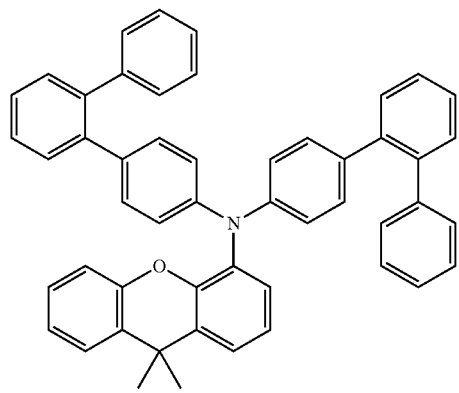

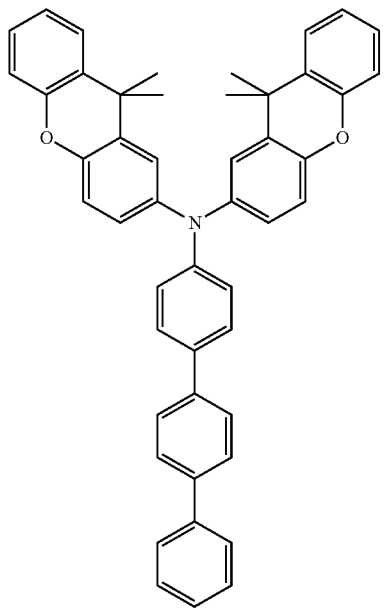
[Chemical Formula 105]
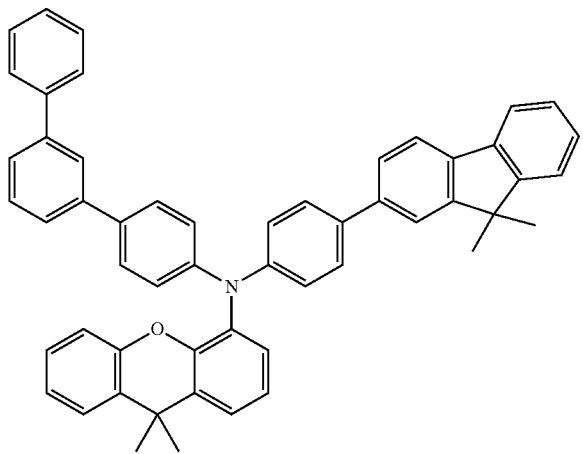
[Chemical Formula 106]
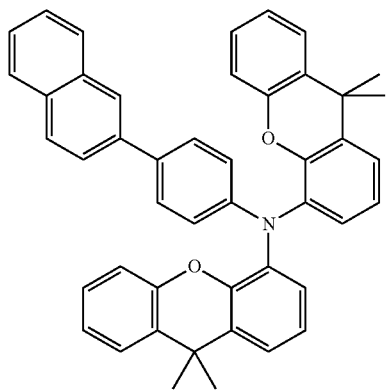
[Chemical Formula 107]

[Chemical Formula 108]
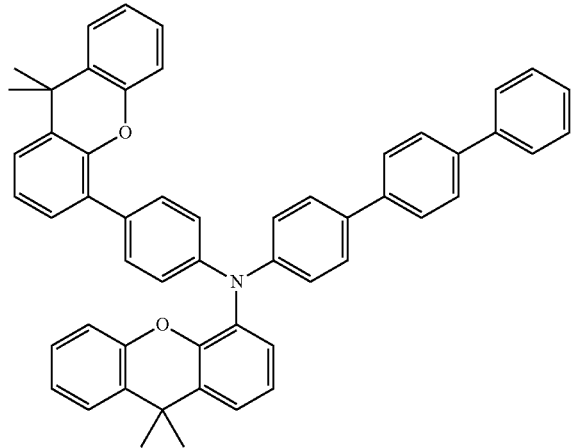
[Chemical Formula 109]
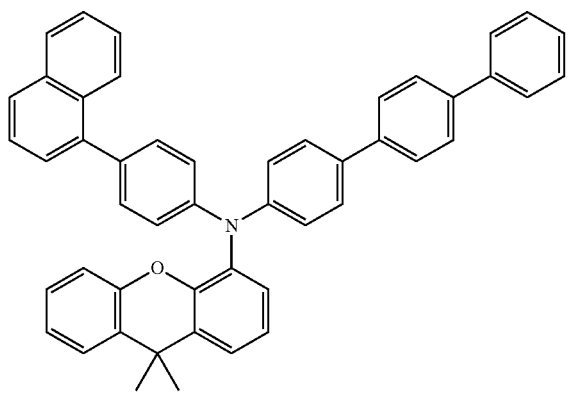
[Chemical Formula 110]
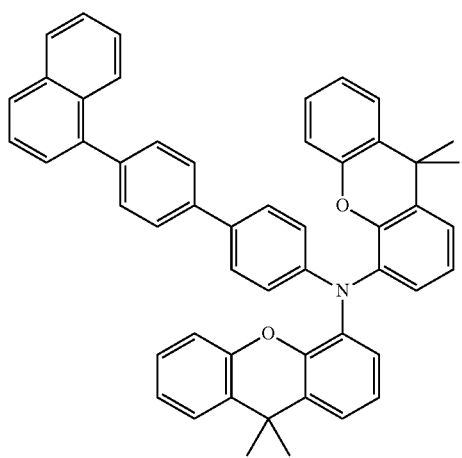

-continued
[Chemical Formula 111]
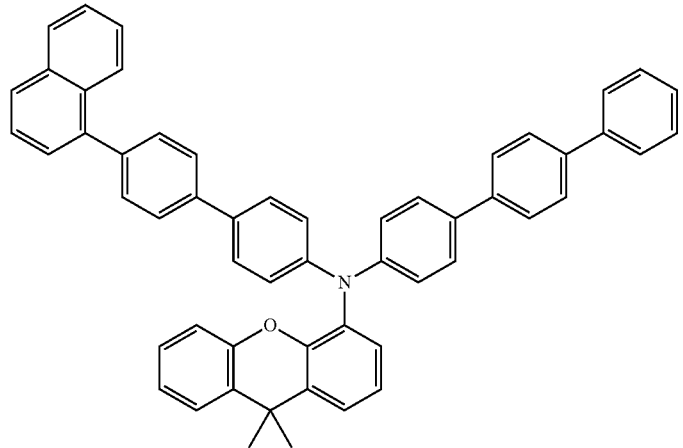
[Chemical Formula 112]
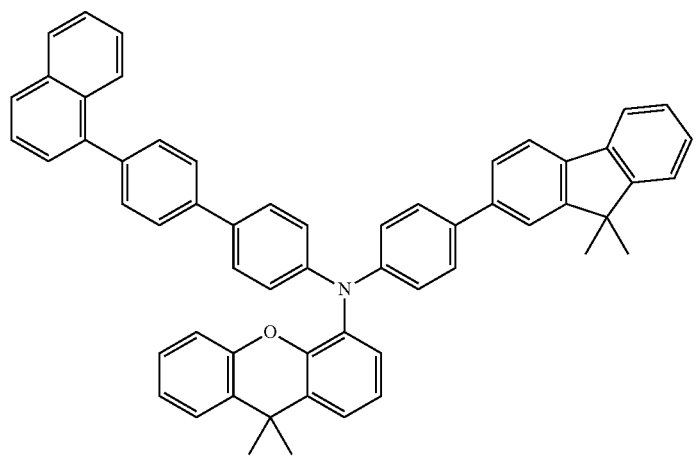
[Chemical Formula 113]
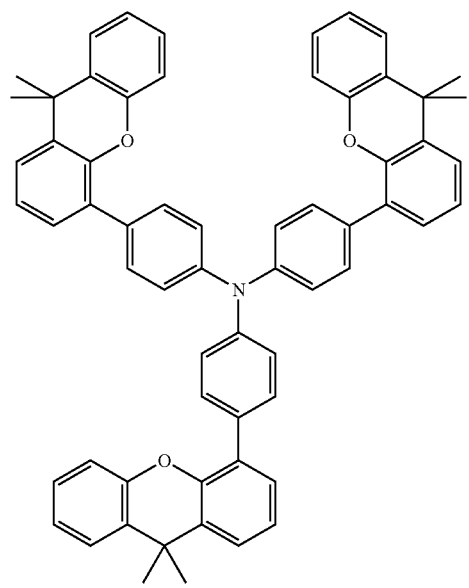

[Chemical Formula 114]
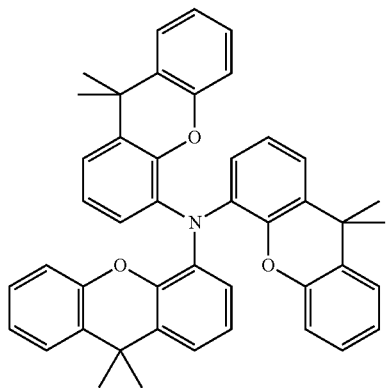
[Chemical Formula 115]
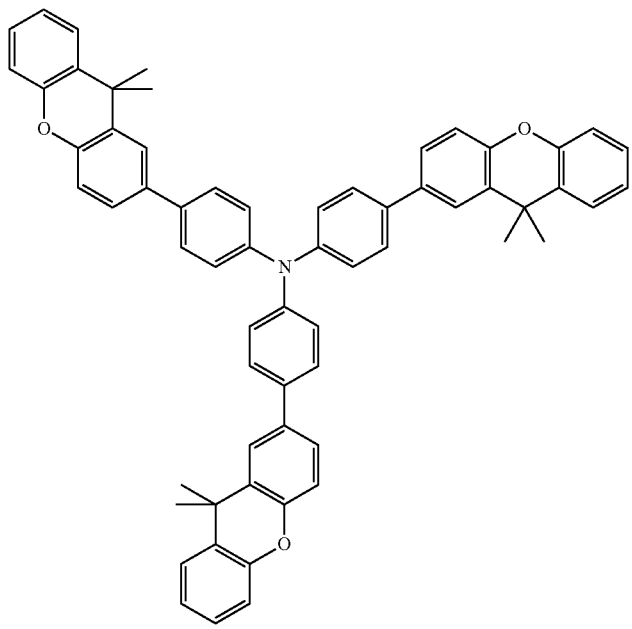
[Chemical Formula 116]
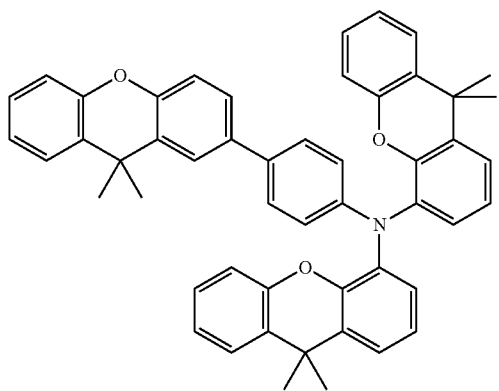

[Chemical Formula 117]
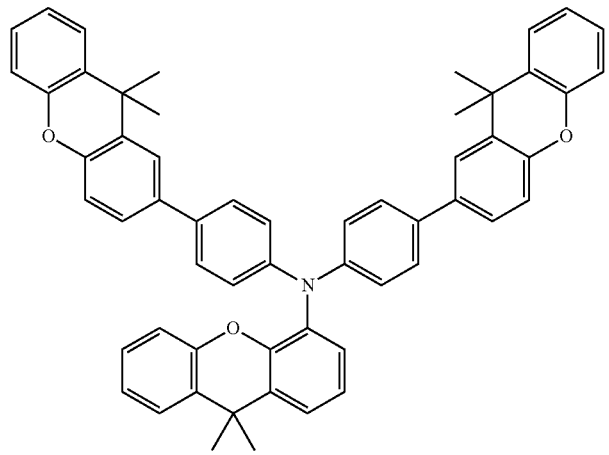
[Chemical Formula 118]
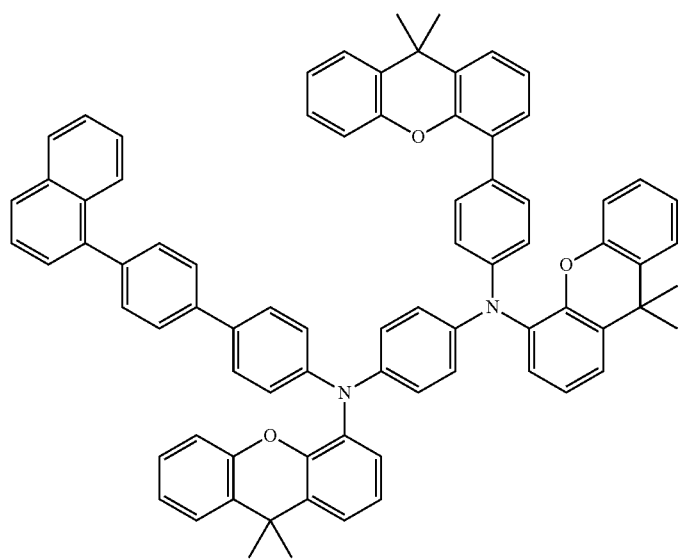
[Chemical Formula 119]
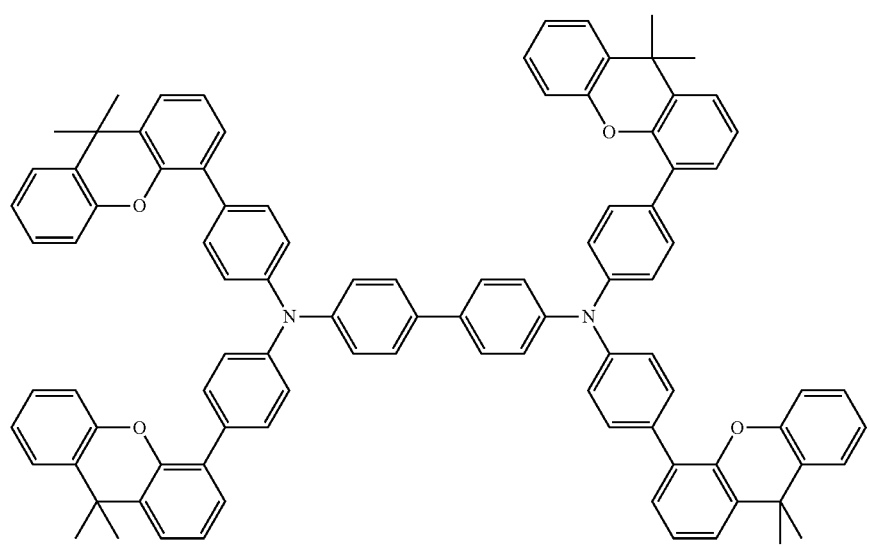

-continued

[Chemical Formula 120]

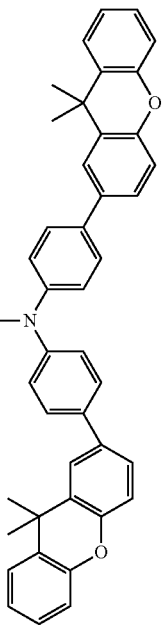

5. An organic electroluminescent device comprising: a first electrode; a second electrode; and an organic layer disposed between the first electrode and the second electrode,
    wherein the organic layer comprises at least one of the organic electroluminescent compounds according to claim 1.

6. The organic electroluminescent device according to claim 5, wherein the organic layer comprises a single layer or a plurality of layers comprising an electroluminescent layer, the organic layer further comprises a hole transport layer, and the hole transport layer comprises at least one of the organic electroluminescent compounds.

7. The organic electroluminescent device according to claim 5, wherein the organic layer comprises at least one layer selected from a hole injection layer, a hole transport layer, an electroluminescent layer, an electron transport layer and an electron injection layer.

8. The organic electroluminescent device according to claim 6, wherein the electroluminescent layer comprises at least one host compound and at least one dopant compound.

9. The organic electroluminescent device according to claim 5, wherein the organic electroluminescent device emits white light by further comprising an organic electroluminescent layer emitting blue, red or green light.

* * * * *